US012748116B2

(12) United States Patent
Hahn et al.

(10) Patent No.: US 12,748,116 B2
(45) Date of Patent: Sep. 29, 2026

(54) REAGENT FOR MASS SPECTROMETRY

(71) Applicant: Roche Diagnostics Operations, Inc., Indianapolis, IN (US)

(72) Inventors: Robert Hahn, Munich (DE); Dieter Heindl, Munich (DE); Hans-Peter Josel, Weilheim (DE); Uwe Kobold, Weilheim (DE); Hannes Kuchelmeister, Munich (DE); Simon Loibl, Wolfratshausen (DE); Heribert Maerz, Paehl (DE); Giuseppe Prencipe, Penzberg (DE); Martin Rempt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 643 days.

(21) Appl. No.: 17/991,366

(22) Filed: Nov. 21, 2022

(65) Prior Publication Data

US 2023/0160904 A1 May 25, 2023

Related U.S. Application Data

(63) Continuation of application No. PCT/EP2021/063288, filed on May 19, 2021.

(30) Foreign Application Priority Data

May 20, 2020 (EP) .................................... 20175802

(51) Int. Cl.
*G01N 33/68* (2006.01)
*C07C 243/34* (2006.01)
(Continued)

(52) U.S. Cl.
CPC ....... *G01N 33/6848* (2013.01); *C07C 243/34* (2013.01); *C07D 213/55* (2013.01);
(Continued)

(58) Field of Classification Search
None
See application file for complete search history.

(56) References Cited

U.S. PATENT DOCUMENTS 7,276,378 B2 10/2007 Myerson
10,281,468 B2 5/2019 Purkayastha et al.
(Continued)

FOREIGN PATENT DOCUMENTS

JP 2009175139 A 8/2009
WO 2011091436 A1 7/2011
(Continued)

OTHER PUBLICATIONS

Lavrynenko, O. et al. Girard derivatization for LC-MS/MS profiling of endogenous ecdysteroids in Drosophila, Journal of Lipid Research vol. 54, 2013, 2265-2272 (Year: 2013).*
(Continued)

*Primary Examiner* — Xiaoyun R Xu
(74) *Attorney, Agent, or Firm* — Taft Stettinius & Hollister LLP

(57) ABSTRACT

The present invention relates to compounds which are suitable to be used in mass spectrometry as well as methods of mass spectrometric determination of analyte molecules using said compounds.

8 Claims, 13 Drawing Sheets

(51) Int. Cl.
*C07D 213/55* (2006.01)
*C07D 213/56* (2006.01)
*C07D 213/74* (2006.01)
*C07D 401/04* (2006.01)

(52) U.S. Cl.
CPC ......... *C07D 213/56* (2013.01); *C07D 213/74* (2013.01); *C07D 401/04* (2013.01); *G01N 2560/00* (2013.01)

(56) References Cited

U.S. PATENT DOCUMENTS

| | | | |
|---|---|---|---|
| 2004/0157344 | A1 | 8/2004 | Wang et al. |
| 2004/0248203 | A1 | 12/2004 | Dratz et al. |

FOREIGN PATENT DOCUMENTS

| | | | |
|---|---|---|---|
| WO | 2013177293 | A1 | 11/2013 |
| WO | 2019048450 | A1 | 3/2019 |
| WO | 2021233997 | A1 | 11/2021 |

OTHER PUBLICATIONS

Al-Dulaymi, M. et al., Tandem mass spectrometric analysis of novel peptide-modified gemini surfactants used as gene delivery vectors, Journal of Mass Spectrometry, 2017, pp. 353-366, vol. 52.
Al-Dulaymi, Mays et al., The development of simple flow injection analysis tandem mass spectrometric methods for the cutaneous determination of peptide-modified cationic gemini surfactants used as gene delivery vectors, Journal of Pharmaceutical and Biomedical Analysis, 2018, pp. 536-547, vol. 159.
Ban, Hitoshi et al., Tyrosine Bioconjugation through Aqueous Ene-Type Reactions: A Click-Like Reaction for Tyrosine, Journal of the American Chemical Society, 2010, pp. 1523-1525, vol. 132.
Beaudry, Francis et al., Development of a rapid and sensitive LC-ESI/MS/MS assay for the quantification of propofol using a simple off-line dansyl chloride derivatization reaction to enhance signal intensity, Journal of Pharmaceutical and Biomedical Analysis, 2005, pp. 411-417, vol. 39.
Frey, Alexander J. et al., Validation of highly sensitive simultaneous targeted and untargeted analysis of keto-steroids by Girard p. derivatization and stable isotope dilution-liquid chromatography-high resolution mass spectrometry, Steroids, 2016, pp. 60-66, vol. 116.
Higashi, Tatsuya et al., Chemical derivatization for enhancing sensitivity during LC/ESI-MS/MS quantification of steroids in biological samples: a review, Journal of Steroid Biochemistry & Molecular Biology, 2016, pp. 57-69, vol. 162.
Higashi, Tatsuya et al., Isotope-coded ESI-enhancing derivatization reagents for differential analysis, quantification and profiling of metabolites in biological samples by LC/MS: A review, Journal of Pharmaceutical and Biomedical Analysis, 2016, pp. 181-193, vol. 130.
Hong, Haizheng et al., Derivatization with Girard Reagent T Combined with LC-MS/MS for the Sensitive Detection of 5-Formyl-2'-deoxyuridine in Cellular DNA, Analytical Chemistry, 2007, pp. 322-326, vol. 79.
Lou, Xianwen et al., Fragmentation of organic ions bearing fixed multiple charges observed in MALDI MS, Journal of Mass Spectrometry, 2018, pp. 39-47, vol. 53.
Mohammed-Saeid, Waleed et al., Mass spectrometric analysis of amino acid/di-peptide modified gemini surfactants used as gene delivery agents: Establishment of a universal mass spectrometric fingerprint, International Journal of Mass Spectrometry, 2012, pp. 182-191, vol. 309.
Otsuka, Hideyuka et al., Definitive Evidence for Inhibition of Calix(6)arene Ring Inversion Obtained from a 1,3-Xylenyl-Bridged Chiral Calix[6]arene, Journal of the American Chemical Society, 1996, pp. 4271-4275, vol. 118.
Rahimoff, René et al., 5-Formyl- and 5-Carboxydeoxycytidines Do Not Cause Accumulation of Harmful Repair Intermediates in Stem Cells, Journal of the American Chemical Society, 2017, pp. 10359-10364, vol. 139.
Shek, P. Y. Iris et al., Fragmentations of Protonated Arginine, Lysine and Their Methylated Derivatives: Concomitant Losses of Carbon Monoxide or Carbon Dioxide and an Amine, Journal of Physical Chemistry A, 2006, pp. 8282-8296, vol. 110, No. 27.
Star-Weinstock, Michal et al., LC-ESI-MS/MS Analysis of Testosterone at Sub-Picogram Levels Using a Novel Derivatization Reagent, Analytical Chemistry, 2012, pp. 9310-9317, vol. 84.
Jin, Wei et al., The determination of gemini surfactants used as gene delivery agents in cellular matrix using validated tandem mass spectrometric method, Journal of Pharmaceutical and Biomedical Analysis, 2019, pp. 164-172, vol. 164.
Zhang, Longhe et al., Syntheses of quaternary ammonium-containing, trithiocarbonate RAFT agents and hemi- telechelic cationomers, Polymer Chemistry, 2014, pp. 1180-1190, vol. 4, Abstract only.
Alley, William, RapiFluor-MS labeled glycan analysis for biotherapeutic proteins, 28th International Carbohydrate Symposium, 2016, Abstract only.
International Search Report; European Patent Office; International Application No. PCT/EP2021/063288; Jul. 12, 2021; 5 pages.
Written Opinion of the International Searching Authority: European Patent Office; International Application No. PCT/EP2021/063288; Jul. 12, 2021; 7 pages.

* cited by examiner

Fig. 4E

| Conc. (ng/mL) | 1. Injektion | 2. Injektion | 3. Injektion |
|---|---|---|---|
| 0 | 1 | 0 | 1 |
| 0.0001 | 1 | 1 | 0 |
| 0.00025 | 2 | 2 | 0 |
| 0.0005 | 5 | 4 | 3 |
| 0.0010 | 6 | 5 | 6 |
| 0.0025 | 24 | 27 | 25 |
| 0.005 | 55 | 48 | 47 |
| 0.0100 | 94 | 84 | 91 |
| 0.0250 | 266 | 267 | 294 |
| 0.0500 | 566 | 590 | 578 |

| | |
|---|---|
| xNG [ng/mL] | 0.00041 |
| xEG [ng/mL] | 0.00083 |
| xBG [ng/mL] | 0.00148 |

Rating based on a LOD enhancement factor

REAGENT FOR MASS SPECTROMETRY

CROSS-REFERENCE TO RELATED APPLICATIONS

This application is a continuation of International PCT Application No. PCT/EP2021/063288 filed on May 19, 2021, which claims priority to European Patent Application No. 20175802.6 filed on May 20, 2020, the contents of each application are incorporated herein by reference in their entireties.

FIELD OF THE INVENTION

The present invention relates to compounds, compositions comprising said compounds, kits comprising said compositions and/or compounds and a complex which are suitable to be used in mass spectrometry. Further, the present invention relates to a method of mass spectrometric determination of analytes using said compounds.

BACKGROUND OF THE INVENTION

Mass spectrometry (MS) is a widely used technique for the qualitative and quantitative analysis of chemical substances ranging from small molecules to macromolecules. In general, it is a very sensitive and specific method, allowing even for the analysis of complex biological, e.g. environmental or clinical samples. However, for several analytes, especially if analysed from complex biological matrices such as serum, sensitivity of the measurement remains an issue.

Often MS is combined with chromatographic techniques, particularly gas and liquid chromatography such as e.g. HPLC. Here, the analysed molecule (analyte) of interest is separated chromatographically and is individually subjected to mass spectrometric analysis (Higashi et al. (2016) J. of Pharmaceutical and Biomedical Analysis 130 p; 181-190).

There is, however, still a need of increasing the sensitivity of MS analysis methods, particularly for the analysis of analytes that have a low abundance or when only little materials (such as biopsy tissues) are available.

In the art, several derivatization reagents (compounds) are known which aim to improve the sensitivity of the measurement for these analytes. Amongst others, reagents comprising charged units and neutral loss units which are combined in a single functional unit (e.g. WO 2011/091436 A1). Other reagents comprising separate units are structurally relatively large which effects the general workflow of sample preparation and the MS measurement (Rahimoff et al. (2017) J. Am. Chem. Soc. 139(30), p. 10359-10364). Known derivatization reagents are for example dansylchloride, RapiFluor-MS (RFMS), Cookson-type reagents, Amplifex Diene, Amplifex Keto, Girard T, Girard P and Pyridinyl amine (Hong and Wang, Anal Chem., 2007, 79(1): 322-326; Frey et al., Steroids, 2016 December, 116:60-66; Francis et al., Journal of Pharmaceutical and Biomedical Analysis, 2005, 39(3-4), 411-417; Alley William, 28th International Carbohydrate Symposium, New Orleans, LA, United States, July 17-21 (2016), ICS-209). Others describe the way to install a permanent charge (positive or negative) onto the analyte of interest which makes it capable to being already ionized and therefore circumvent the ionization step within an ion source which is mostly the part where analyte losses occur. All of these bear disadvantages due to often insufficient labeling efficiencies, generation of structural isomers due to coupling chemistry, non-optimal ionization efficiencies, disadvantages for chromatographic separation after coupling, non-optima fragmentation behaviour due to many fragmentation pathways and need for high collision energies.

There is thus an urgent need in the art for a derivatization reagents which allows for a sensitive detection of analytes from complex biological matrices as well as exhibiting a chemical structure which does not negatively influence the MS measurement workflow. This is of particular importance in a random-access, high-throughput MS set up, wherein several different analytes exhibiting different chemical properties have to be measured in a short amount of time.

The present invention relates to a novel reagents/compounds which allows for a sensitive determination of analyte molecules such as steroids, proteins, and other types of analytes, in biological samples. The reagent is designed in a modular manner to allow the individual adaption for specific needs arising in the measurement of certain analytes or for specific workflow adaptations.

It is an object of the present invention to provide a compound, a kit and a composition each of these comprises said compound for efficiently detection of an analyte by mass spectrometry. Furthermore, an object of the present invention is to provide a complex and a method for mass spectrometric determination of an analyte.

This object is or these objects are solved by the subject matter of the independent claims. Further embodiments are subjected to the dependent claims.

SUMMARY OF THE INVENTION

In the following, the present invention relates to the following aspects:

In a first aspect, the present invention relates to a compound for quantitative detection of an analyte using mass spectrometric determination, wherein said compound comprises a permanent charge, in particular a permanent net charge, wherein said compound is capable of covalently binding to the analyte, wherein said compound has a mass m1 and a net charge z1, wherein the compound is capable of forming at least one daughter ion having a mass $m2<m1$ and a net charge $z2<z1$ after fragmentation by mass spectrometric determination, wherein $m1/z1<m2/z2$.

In a second aspect, the present invention relates to a composition comprising the compound of the first aspect of the present invention.

In a third aspect, the present invention relates to a kit comprising the compound of the first aspect of the present invention or the composition of the second aspect of the present invention.

In a fourth aspect, the present invention relates to a complex for quantitative detection of an analyte using mass spectrometric determination, wherein the complex is formed by the analyte and a compound, which are covalently linked to each other, wherein the complex comprises a permanent charge, in particular a permanent net charge, wherein said complex has a mass m3 and a net charge z3, wherein the complex is capable of forming at least one daughter ion having a mass $m4<m3$ and a net charge $z4<z3$ after fragmentation by mass spectrometric determination, wherein $m3/z3<m4/z4$.

In a fifth aspect, the present invention relates to a use of the compound of the first aspect of the present invention for mass spectrometric determination of the analyte.

In a sixth aspect, the present invention relates to a method for mass spectrometric determination of an analyte comprising the steps of:

(a) reacting the analyte with the compound of the first aspect of the present invention, whereby a complex of the fourth aspect of the present invention is formed, (b) subjected the complex from step (a) to a mass spectrometric analysis.

LIST OF FIGURES

Figure 4A:
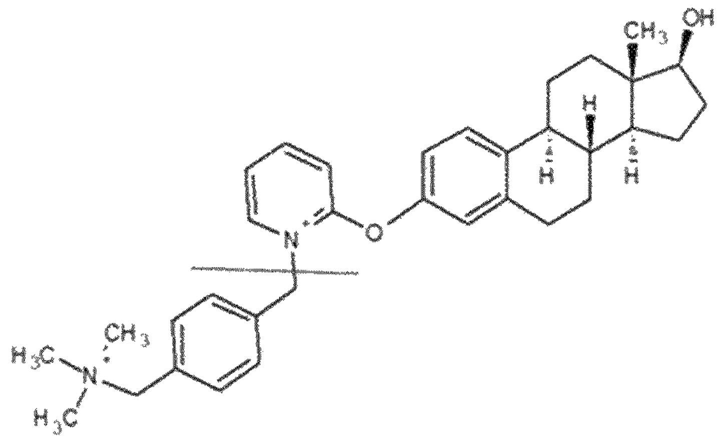
Figure 4B:
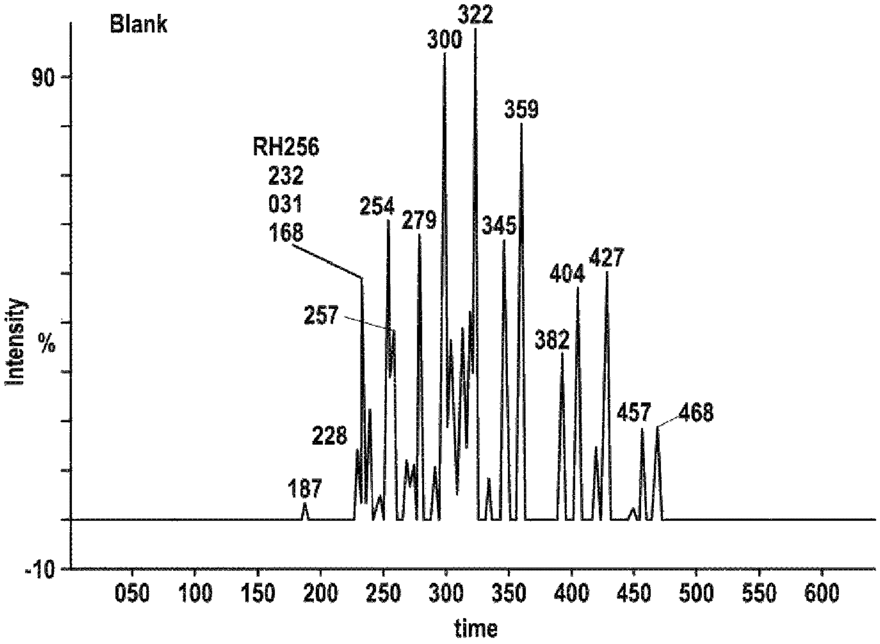
Figure 4C:
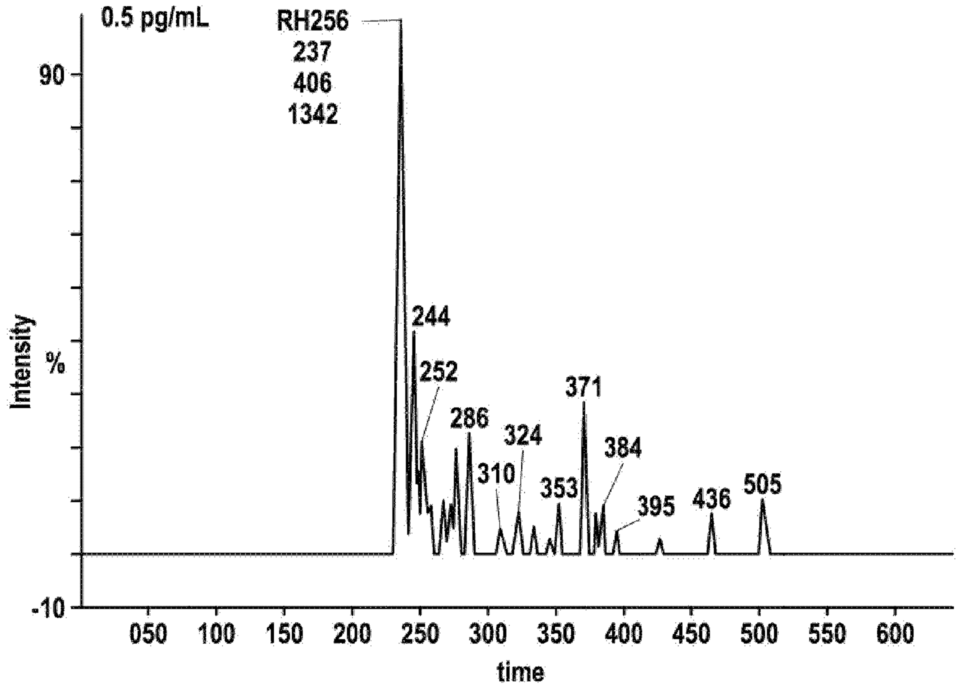
Figure 4D:
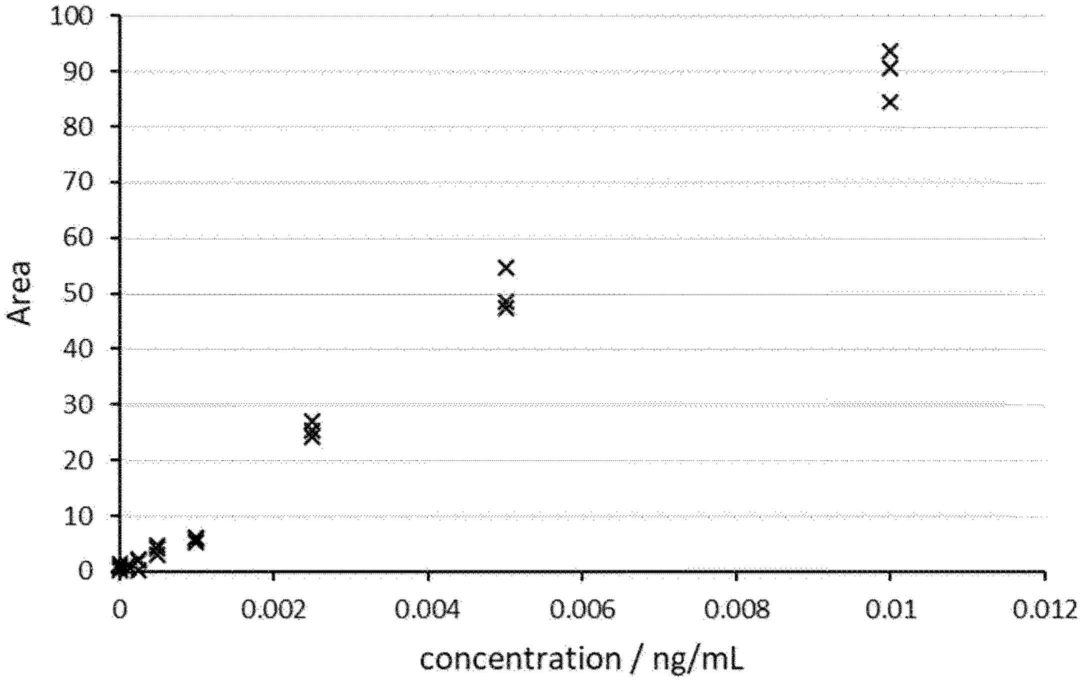

FIG. 4A to FIG. 4E show the lower limits of quantification (LLOQ) of a complex, comprising a labeled two times charged estradiol. FIG. 4A shows the structure of the complex (Estradiol conjugated with Label 6). FIG. 4B shows the MS blank chromatogram at the respective mass transition (intensity in % versus retention time) FIG. 4C shows chromatogram at the respective mass transition (intensity in % versus retention time) of Estradiol conjugated with Label 6 (related 0.5 pg/ml estradiol). FIG. 4D shows the calibration curve of Estradiol conjugated with Label 6 in the concentration range of 0-0.01 ng/ml with respect to estradiol. FIG. 4E shows the data of the calibration curve ranging from Ong/ml to 0.05 ng/ml of Estradiol conjugated with Label 6 with respect to estradiol. The absolute area of three individual injections are shown and the respective detection limits according to DIN 32645 are reported. NG means detection limit, EG the detection limit with 95% correctness, BG means limit of quantification (LOQ). Native estradiol LLOQ for the best mode/setup is appr. 5 ng/ml.

Figure 5A:
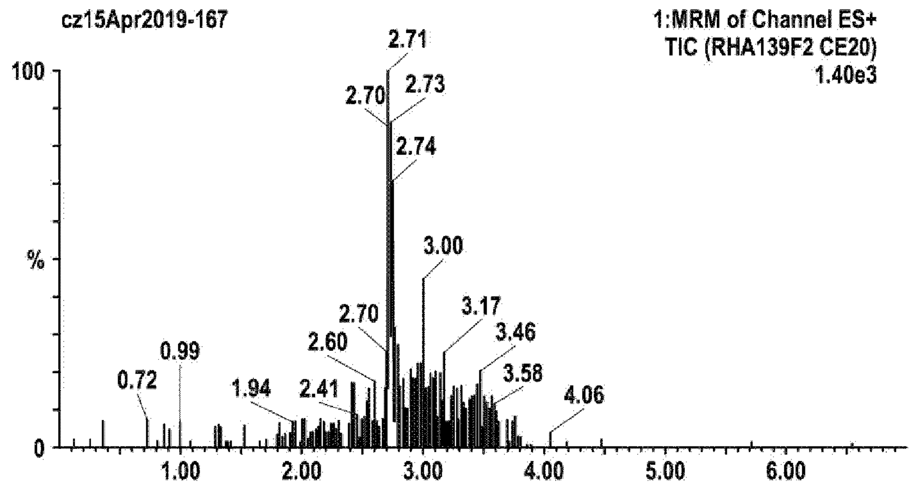
Figure 5B:
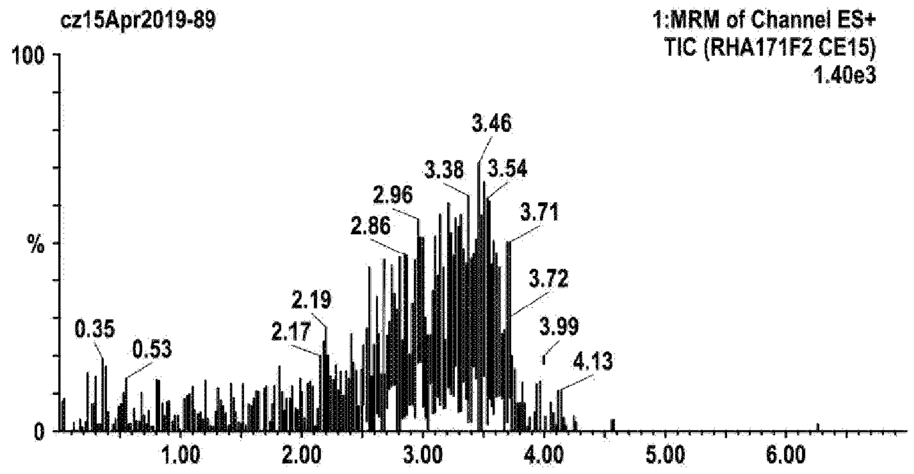
Figure 5C:
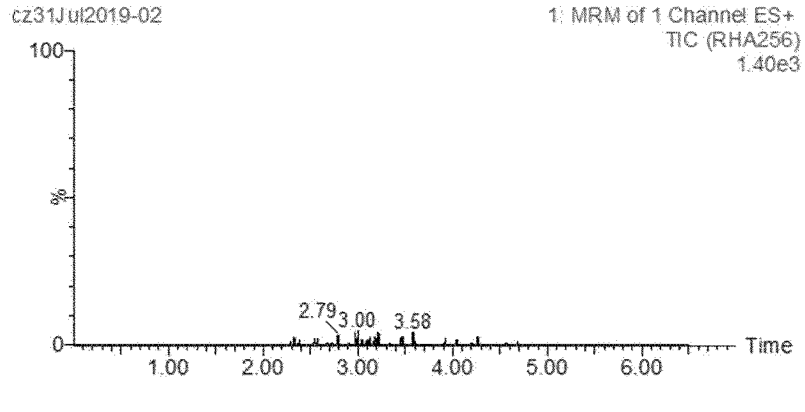

FIG. 5A to FIG. 5C show the illustration of a MS chromatogram of a blank injection and the respective mass transitions for (intensity in % versus retention time of three embodiments) RHA139F2, RHA171F2 and Estradiol conjugated with Label 6 respectively.

Figure 6:
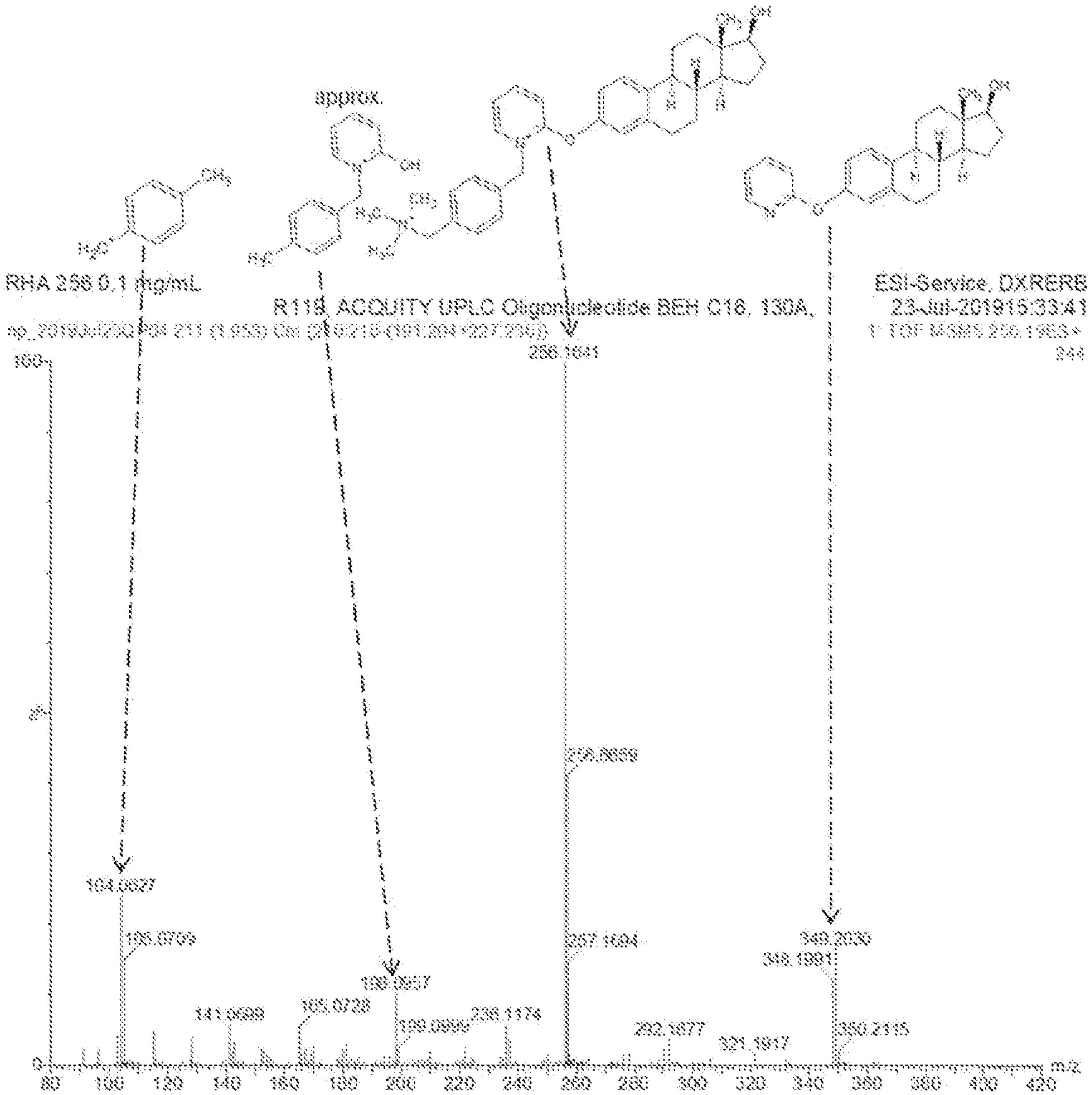

FIG. 6 shows the illustration of a MS spectrum (intensity in % versus m/z) of a two times positive charged complex comprising estradiol or fragments thereof as the binding analyte and Estradiol conjugated with Label 6 or fragments thereof as the binding compound according to the present invention.

Figure 7:
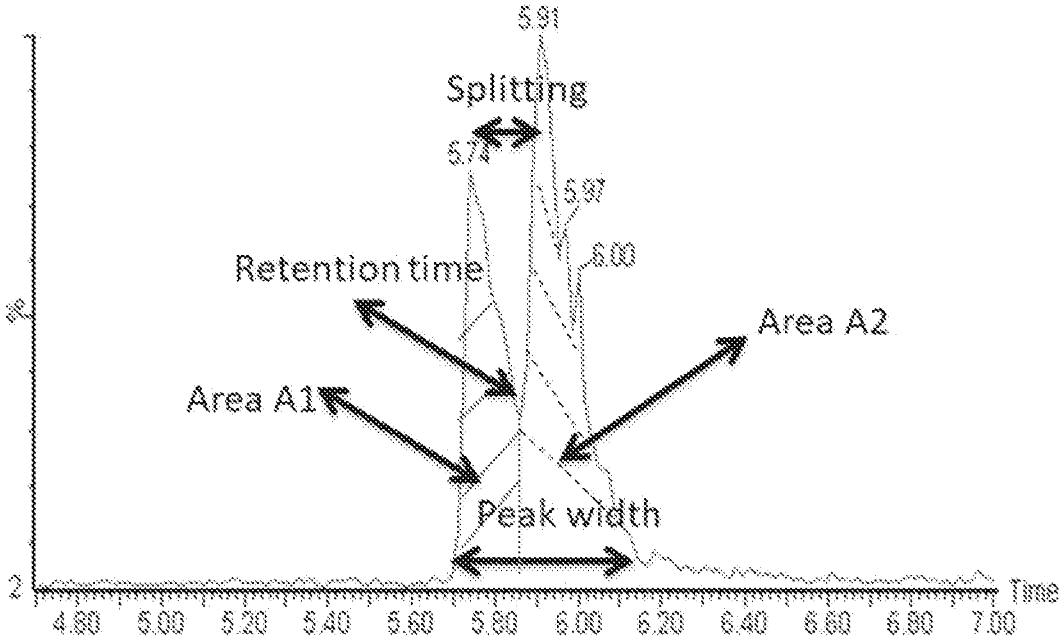

FIG. 7 shows the schematic illustration of peak "splitting": It describes the capability of the chromatographic system to separate the different isomers resulting from the derivatization reaction of the analyte molecule from each other.

Figure 8:
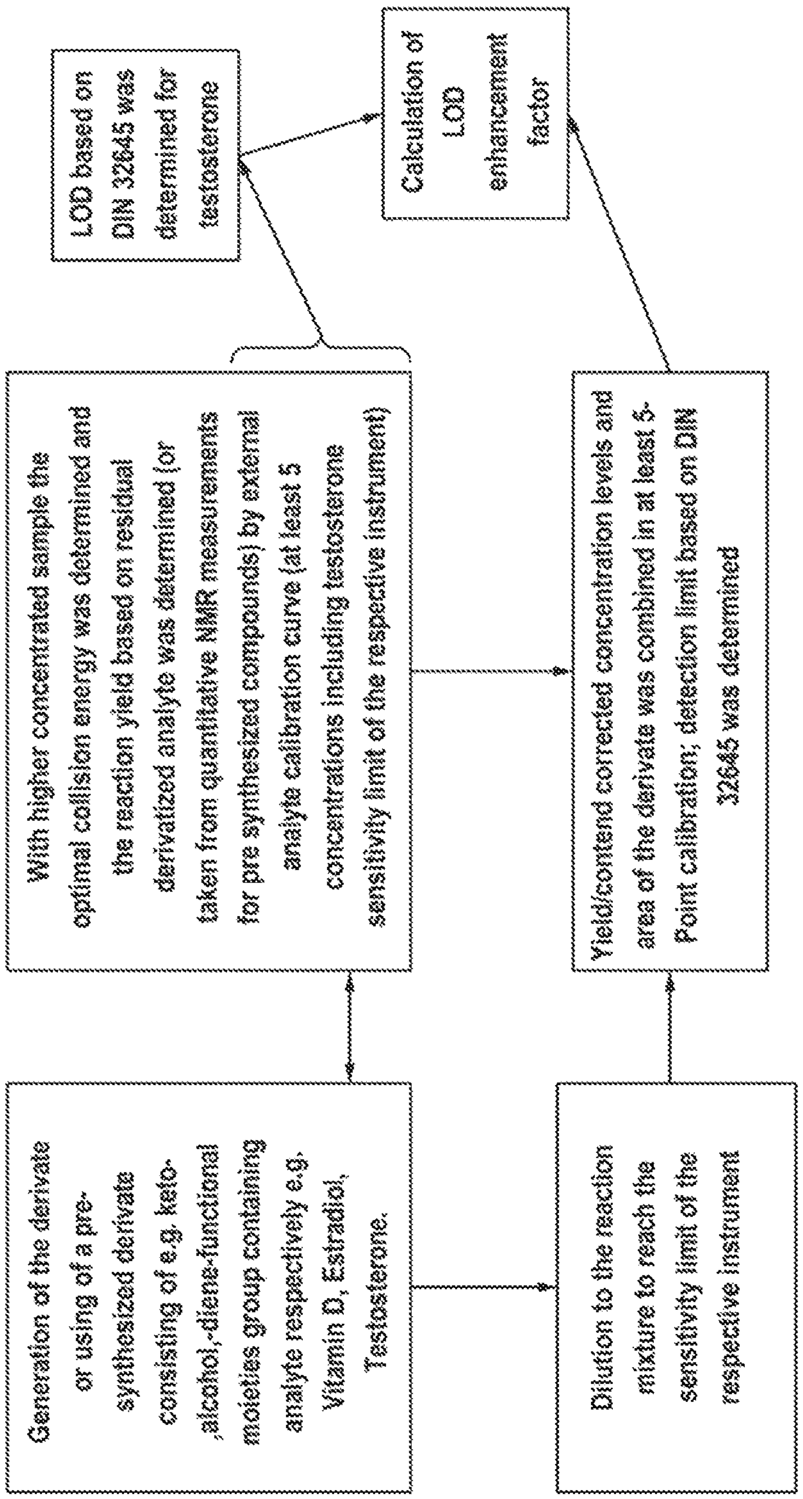

FIG. 8 shows schematic representation of the workflow determining the Enhancement Factor in comparison to underivatized analyte.

Figure 9A:
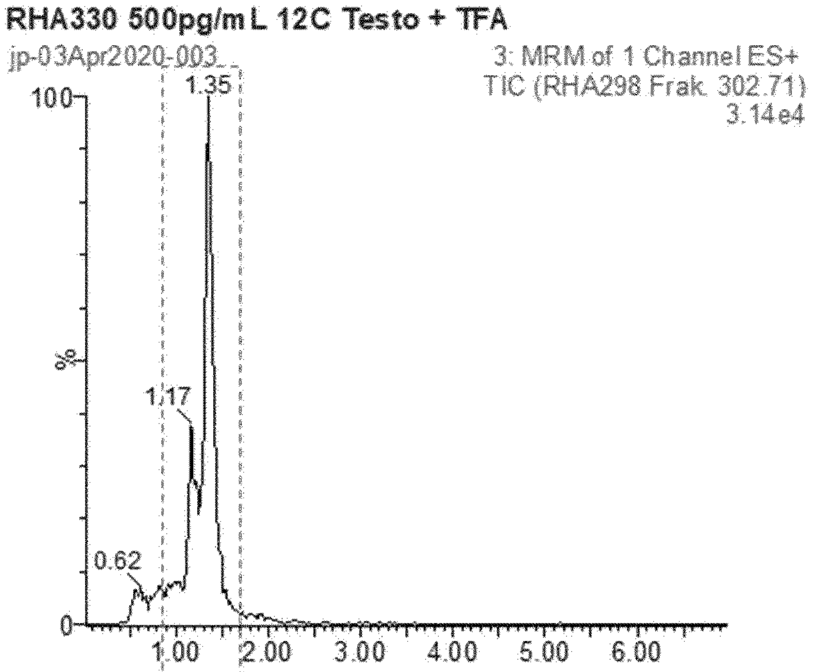
Figure 9B:
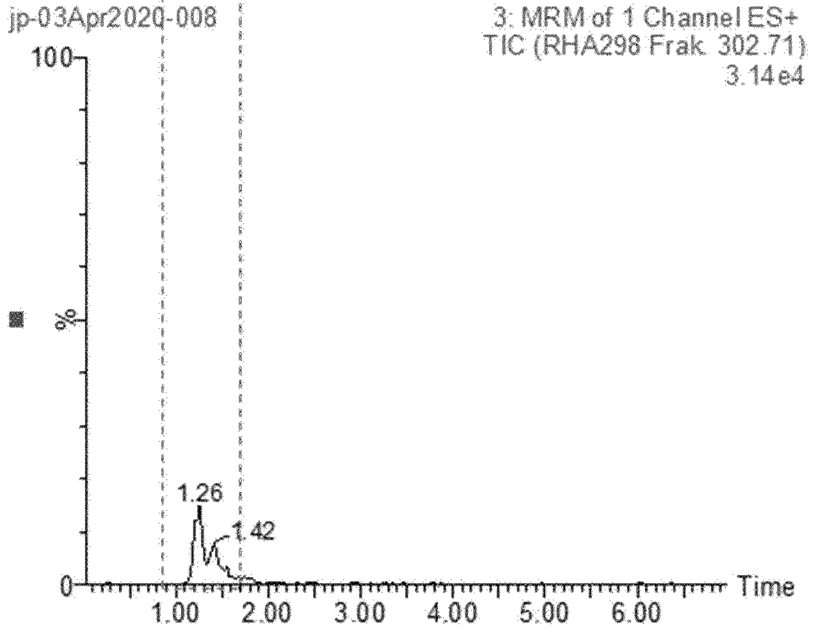

FIG. 9A and FIG. 9B show the signal quenching effect by TFA on doubly charged compounds/derivatives or complex thereof.

FIG. 10A to FIG. 10D show MS spectra (intensity in % versus m/z) of fragmentation patterns of the compound and/or complex.

Figure 11:
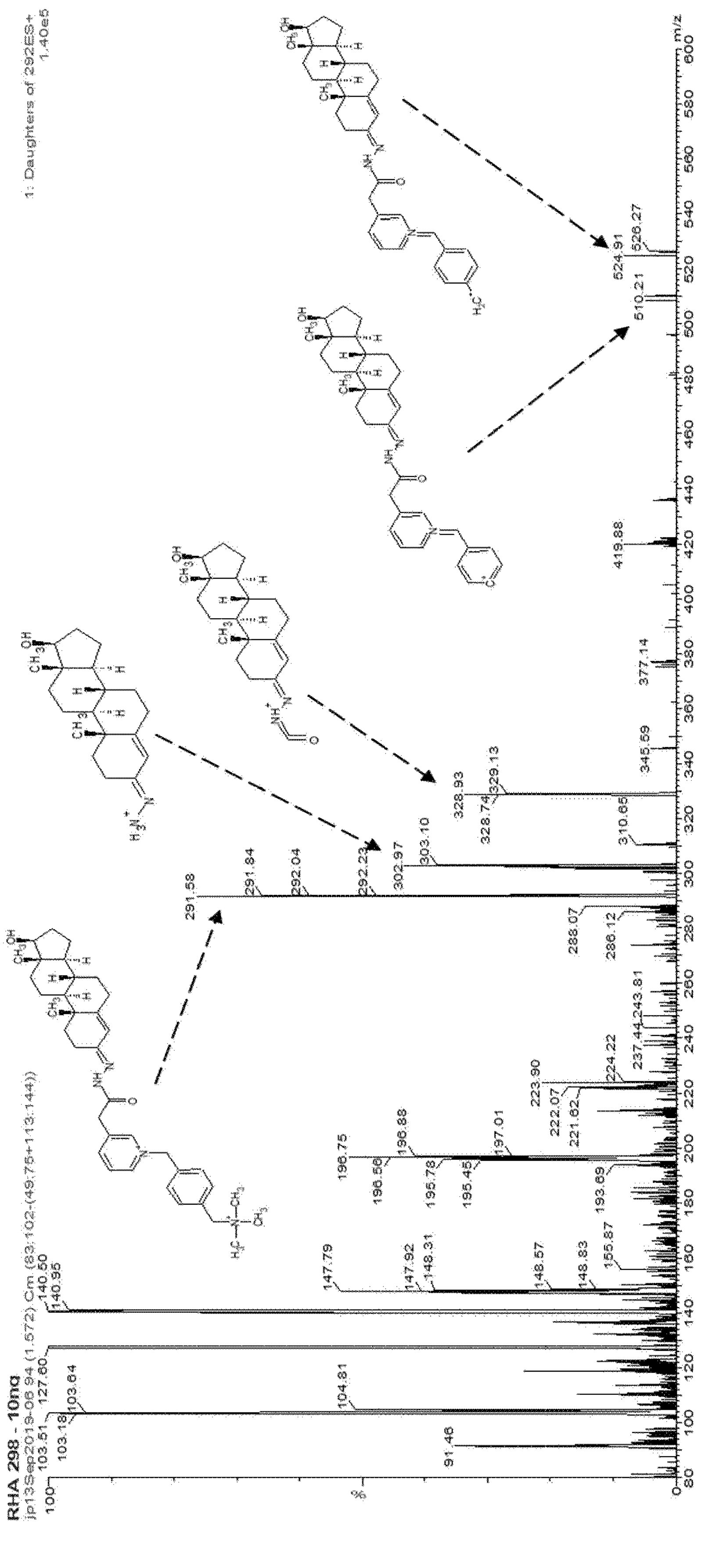

FIG. 11 shows MS spectra (intensity in % versus m/z) of fragmentation patterns of the compound and/or complex.

DETAILED DESCRIPTION OF THE INVENTION

Before the present invention is described in detail below, it is to be understood that this invention is not limited to the particular embodiments and examples described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

In the context of the present invention, the term "compound" refers to a chemical substance having a specific chemical structure. Said compound may comprise one or more reactive groups. Each reactive group may fulfil a different functionality, or two or more reactive groups may fulfil the same function. Reactive groups include but are not limited to reactive units, charged units, and neutral loss units. In the context of the present invention, the term "binding compound" refers to the said compound, which is bonded to the analyte. In principle, the compound and the binding compound can be identical. The compound and the binding compound can be substantially identical. Substantially identical can mean that both compounds have an identical chemical structure with the exception that they differ from each other by the structure of the reactive unit K and/or the structure of the coupling group Q. Preferably, the compound is capable of forming a binding to the analyte, but is not yet bounded to the analyte. The binding compound is bounded to the analyte.

The term "Mass Spectrometry" ("Mass Spec" or "MS") or "mass spectrometric determination" or "mass spectrometric analysis" relates to an analytical technology used to identify compounds by their mass. MS is a methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net charge equal to one or more units. Negative ions are those having a net negative charge of one or more units, while positive ions are those having a net positive charge of one or more units. The MS method may be performed either in "negative ion mode", wherein negative ions are generated and detected, or in "positive ion mode" wherein positive ions are generated and detected. "After fragmentation by mass spectrometric determination" can mean that e.g. the compound, composition or complex passed through a mass spectrometer and were fragmented.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Most sample workflows in MS further include sample preparation and/or enrichment steps, wherein e.g. the analyte(s) of interest are separated from the matrix using e.g. gas or liquid chromatography. Typically, for the mass spectrometric measurement, the following three steps are performed:

1. a sample comprising an analyte of interest is ionized, usually by complex formation with cations, often by protonation to cations. Ionization source include but are not limited to electrospray ionization (ESI) and atmospheric pressure chemical ionization (APCI).
2. the ions are sorted and separated according to their mass and charge. High-field asymmetric-waveform ion-mobility spectrometry (FAIMS) may be used as ion filter.
3. the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated Ni gas may be used to improve removal of solvent. The gas-phase ionization in APCI can be more effective than ESI for analyzing less-polar entity.

"High-field asymmetric-waveform ion-mobility spectrometry (FAIMS)" is an atmospheric pressure ion mobility technique that separates gas-phase ions by their behavior in strong and weak electric fields.

"Multiple reaction mode" or "MRM" is a detection mode for a MS instrument in which a precursor ion and one or more fragment ions are selectively detected.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the term "analyte", "analyte molecule", or "analyte(s) of interest" are used interchangeably referring the chemical species to be analysed via mass spectrometry. Chemical species suitable to be analysed via mass spectrometry, i.e. analytes, can be any kind of molecule present in a living organism, include but are not limited to nucleic acid (e.g. DNA, mRNA, miRNA, rRNA etc.), amino acids, peptides, proteins (e.g. cell surface receptor, cytosolic protein etc.), metabolite or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxin, etc.) or a metabolite of such a substance. Such analyte may serve as a biomarker. In the context of present invention, the term "biomarker" refers to a substance within a biological system that is used as an indicator of a biological state of said system. In the context of the present invention, the term "binding analyte" refers to the said analyte, which is bonded to the compound for forming a complex. In principle, the analyte and the binding analyte can be identical. The analyte and the binding analyte can be substantially identical. Substantially identical can mean that both analytes have an identical chemical structure with the exception that they differ from each other by the structure of the functional group. Preferably, the analyte is capable of forming a binding to the compound, but is not yet bounded to the compound. The binding analyte is bounded to the compound.

The term "permanent charge" or "permanent charged" is used in the context of the present disclosure that the charge, e.g. a positive or negative charge, of a unit is not readily reversible, for example, via flushing, dilution, filtration, and the like. In particular, this means in the context, that the permanent charge is not in equilibrium with their non permanent charge. Permanent charges are formed by covalent bond formation, which are stable even under high- and low pH environments (e.g. positive charge pH>12 and for negative charges pH<1). Therefore, the respective permanent charged molecule is either a strong base or a strong acid. For a positive charge z=1 permanent charges exhibit pKs values of pKs>12 while for negative charges z=−1 pKs<1. A permanent charge may be the result, for example, of covalently bonding. A reversible charge (a non-permanent charge) may be the result in contrast to a permanent charge, for example, of an electrostatic interaction. The compound of the present invention has a net charge z1, in particular before fragmentation. After fragmentation the compound can be splitted or cleaved into at least one daughter ion. The daughter ion has a net charge z2, which is smaller than the net charge z1 (z2<z1). The complex of the invention has a net charge z3, in particular before fragmentation. After fragmentation, the complex can be splitted or cleaved into at least one daughter ion having a net charge z4, which is smaller than the net charge z3 (z4<z3). At least one daughter ion can mean in this context that one daughter ion or more are formed after fragmentation. The one daughter ion and the other daughter ions differentiate from each other at least by their mass, charge or structure. In the context of the disclosure, by comparison the net charge z2 of the daughter ion and the net charge z1 of the compound, the absolute value of the net charges are crucial. For example, if the compound has a double negative net charge z1 (z1=−2) and the daughter ion has one negative net charge z2 (z2=−1), then the net charge z2 is smaller than the net charge z1 (z2<z1), because the absolute value of the net charge z1 (z1=2) is more than the absolute value of the net charge z2 (z2=1). By comparison the net charges z1 and z2, the absolute values of the net charges are compared instead of the total values.

In the context of the disclosure, the term "permanent charge" or "permanent net charge" does not include pseudo-molecular ion, for example, $[M^{+}H]^{+}$ or $[M^{-}H]^{-}$ or $[M+Na^{+}]^{+}$ or $[M+Cl^{-}]^{-}$ etc.

The term "permanent net charge" or "net charged" is used in the context of the present disclosure that the permanent net charge is the total permanent charge an ion or molecule has. Permanent net charge can be calculated as follows: number of protons−number of electrons=permanent net charge. A permanent net charge can be seen as a covalent combination of atoms which forms by bond rearrangements a charged moiety in the molecule (e.g. quaternary nitrogen, tetramethylammonium) while a net charge can also exist by addition or the abstraction of atoms e.g. hydrogen to result in a pseudomolecular ion consisting of $[M^{+}H]^{+}$ or $[M^{-}H]^{-}$. For Example, if the compound has two permanent positive charges and one permanent negative charge, then the permanent net charge is +1 (2*(+1)+(−1)=(+1)).

The term "said compound is capable of covalently binding to the analyte" means that the compound is suitable to bind to the analyte. The binding between the compound and the analyte is covalent.

The term "quantitative detection of an analyte using mass spectrometric determination" means that the quantity of the analyte of interest is measured or determined by mass spectrometry.

The term "mass", for example, m1, m2, m3, m4 or mx with x >4, represents the atomic mass, in particular the unified atomic mass. The unit of the unified atomic mass is u. In the biomedical field Dalton [Da] instead of the unified atomic mass [u] can be used. The Dalton is not an SI unit. The dalton is equivalent to unified atomic mass in that there is no conversion factor between these units. A "mass spectrum" is the two-dimensional representation of signal intensity (ordinate) versus m/z (abscissa). The position of a peak, as signals are usually called, reflects the m/z of an ion that has been created from the compound, analyte or combinations thereof (complex) within the ion source. The intensity of this peak correlates to the abundance of that ion. Often but not necessarily, the peak at highest m/z results from the detection of the intact ionized molecule, the molecular ion, $M^{+}$. The molecular ion peak is usually accompanied by several peaks at lower or higher m/z caused by fragmentation of the compound, analyte or complex to yield fragment ions. Consequently, the respective peaks in the mass spectrum may be referred to as fragment ion peaks or daughter ion peaks. m/z is dimensionless by definition.

The term "fragmentation" can mean that the compound, analyte and/or complex is dissociated and form ions, e.g. at least one daughter ion, by passing the compound, analyte and/or complex in the ionization chamber of a mass spectrometer. The fragments cause a unique pattern in the mass spectrum. The term "fragmentation" can refer to the dissociation of a single molecule into two or more separate molecules. As used herein, the term fragmentation refers to a specific fragmentation event, wherein the breaking point in the parent molecule at which the fragmentation event takes place is well defined, and wherein the two or more daughter molecules resulting from the fragmentation event are well characterised. It is well-known to the skilled person how to determine the breaking point of a parent molecule as well as the two or more resulting daughter molecules. The resulting daughter molecules may be stable or may dissociate in subsequent fragmentation events. Exemplified, in case a parent molecule undergoing fragmentation comprises a N-benzylpyridinium unit, the skilled person is able to determine based on the overall structure of the molecule whether the pyridinium unit will fragment to release an benzyl entity or would be released completely from the parent molecule, i.e the resulting daughter molecules would either be an benzyl molecule and a parent molecule lacking of benzyl. Fragmentation may occur via collision-induced dissociation (CID), electron-capture dissociation (ECD), electron-transfer dissociation (ETD), negative electron-transfer dissociation (NETD), electron-detachment dissociation (EDD), photodissociation, particularly infrared multiphoton dissociation (IRMPD) and blackbody infrared radiative dissociation (BIRD), surface-induced dissociation (SID), Higher-energy C-trap dissociation (HCD), charge remote fragmentation.

The term "m1/z1<m2/z2" means that the mass-to-charge ratio of the compound (m1/z1) is smaller than the mass-to-charge ratio of at least one or exact one daughter ion of the compound (m2/z2).

The term "m3/z3<m4/z4" means that the mass-to-charge ratio of the complex (m3/z3) is smaller than the mass-to-charge ratio of at least one or exact one daughter ion of the complex (m4/z4).

The term "limit of detection" or "LOD" is the lowest concentration of an analyte that the bioanalytical procedure can reliably differentiate the analyte from background noise.

The term "signal-to-noise ratio" or S/N describes the uncertainty of an intensity measurement and provides a quantitative measure of a signal's quality by quantifying the ratio of the intensity of a signal relative to noise.

Analytes may be present in a sample of interest, e.g. a biological or clinical sample. The term "sample" or "sample of interest" are used interchangeably herein, referring to a part or piece of a tissue, organ or individual, typically being smaller than such tissue, organ or individual, intended to represent the whole of the tissue, organ or individual.

Upon analysis a sample provides information about the tissue status or the health or diseased status of an organ or individual. Examples of samples include but are not limited to fluid samples such as blood, serum, plasma, synovial fluid, spinal fluid, urine, saliva, and lymphatic fluid, or solid samples such as dried blood spots and tissue extracts. Further examples of samples are cell cultures or tissue cultures.

A "covalent bond" or "covalently linked" or "covalently bonded" is at least one chemical bond that involves the sharing of electron pairs between atoms or molecules, e.g. between the compound and the analyte.

The terms "unit" and "moiety" can be used interchangeable, e.g. Mc Lafferty fragmentation moiety and McLafferty fragmentation unit can be used interchangeable.

Numerical values, e.g. 1, 2, 3, 4, 5 or 6, for the charges, e.g. z1, z2, z3, z4 or zx with x >4, are absolute values of the charges. For example, net charge z1=2 can mean that the net charge z1 is +2 or the net charge is −2. Preferably, the charges in this case are positive numerical values, e.g. 2=+2.

The terms "compound" and "label" can be used interchangeable.

The term "more fragments" in the term "compound is capable of forming further daughter ions, each of the further daughter ions comprises a fragment of the compound or more fragments of the compound" means that the compound comprises one fragment or more than one fragment, which are different from each other or can be different from each other. In particular, the further daughter ions differentiate from each other at least by their mass, charge or structure.

In the context of the present disclosure, the sample may be derived from an "individual" or "subject". Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be pre-treated in a sample- and/or analyte specific manner. In the context of the present disclosure, the term "pre-treatment" refers to any measures required to allow for the subsequent analysis of a desired analyte via Mass Spectrometry. Pre-treatment measures typically include but are not limited to the elution of solid samples (e.g. elution of dried blood spots), addition of hemolyzing reagent (HR) to whole blood samples, and the addition of enzymatic reagents to urine samples. Also the addition of internal standards (ISTD) is considered as pre-treatment of the sample.

The term "hemolysis reagent" (HR) refers to reagents which lyse cells present in a sample, in the context of this invention hemolysis reagents in particular refer to reagents which lyse the cell present in a blood sample including but not limited to the erythrocytes present in whole blood samples. A well known hemolysis reagent is water ($H_2O$). Further examples of hemolysis reagents include but are not limited to deionized water, liquids with high osmolarity (e.g. 8M urea), ionic liquids, and different detergents.

Typically, an "internal standard" (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer.

Typically, but not necessarily, the ISTD is an isotopically labeled variant (comprising e.g. $^{2}H$, $^{13}C$, or $^{15}N$ etc. label) of the analyte of interest.

In addition to the pre-treatment, the sample may also be subjected to one or more enrichment steps. In the context of the present disclosure, the term "first enrichment process" or "first enrichment workflow" refers to an enrichment process which occurs subsequent to the pre-treatment of the sample and provides a sample comprising an enriched analyte relative to the initial sample. The first enrichment workflow may comprise chemical precipitation (e.g. using acetonitrile) or the use of a solid phase. Suitable solid phases include but are not limited to Solid Phase Extraction (SPE) cartridges, and beads. Beads may be non-magnetic, magnetic, or paramagnetic. Beads may be coated differently to be specific for the analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores.

In the context of the present disclosure the term "second enrichment process" or "second enrichment workflow" refers to an enrichment process which occurs subsequent to the pre-treatment and the first enrichment process of the sample and provides a sample comprising an enriched analyte relative to the initial sample and the sample after the first enrichment process.

The term "chromatography" refers to a process in which a chemical mixture carried by a liquid or gas is separated into components as a result of differential distribution of the chemical entities as they flow around or over a stationary liquid or solid phase.

The term "liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) is termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18 (octadecylsilyl) as the stationary phase) is termed reversed phase liquid chromatography (RPLC). Micro LC refers to a HPLC method using a column having a narrow inner column diameter, typically below 1 mm, e.g. about 0.5 mm. "Ultra high performance liquid chromatography" or "UHPLC" refers to a HPLC method using a pressure of 120 MPa (17,405 lbf/in2), or about 1200 atmospheres. Rapid LC refers to an LC method using a column having an inner diameter as mentioned above, with a short length <2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time <1 min.

Further well-known LC mode include hydrophilic interaction chromatography (HILIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

The term "reactive unit" refers to a unit able to react with another molecule, i.e. which is able to form covalent bond with another molecule, such as an analyte of interest.

Typically, such covalent bond is formed with a chemical group present in the other molecule. Accordingly, upon chemical reaction, the reactive unit of the compound forms a covalent bond with a suitable chemical group present in the analyte molecule. As this chemical group present in the analyte molecule, fulfils the function of reacting with the reactive unit of the compound, the chemical group present in the analyte molecule is also referred to as the "functional group" of the analyte. The formation of the covalent bond occurs in each case in a chemical reaction, wherein the new covalent bond is formed between atoms of the reactive group and the functional groups of the analyte. It is well known to the person skilled in the art that in forming the covalent bond between the reactive group and the functional groups of the analyte, atoms are lost during this chemical reaction.

In the context of the present disclosure, the term "complex" refers to the product produced by the reaction of a compound with an analyte molecule. This reaction leads to the formation of a covalent bond between the compound and the analyte. Accordingly, the term complex refers to the covalently bound reaction product formed by the reaction of the compound with the analyte molecule.

A "kit" is any manufacture (e.g., a package or container) comprising at least one reagent, e.g., a medicament for treatment of a disorder, or a probe for specifically detecting a biomarker gene or protein of the invention. The kit is preferably promoted, distributed, or sold as a unit for performing the methods of the present invention. Typically, a kit may further comprise carrier means being compartmentalized to receive in close confinement one or more container means such as vials, tubes, and the like. In particular, each of the container means comprises one of the separate elements to be used in the method of the first aspect. Kits may further comprise one or more other reagents including but not limited to reaction catalyst. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

Embodiments

In a first aspect, the present invention relates to compounds or at least one compound for quantitative detection of an analyte using mass spectrometric determination, wherein said compound comprises a permanent charge, in particular a permanent net charge, wherein said compound is capable of covalently binding to the analyte, wherein said compound has a mass m1 and a net charge z1, wherein the compound is capable of forming at least one daughter ion having a mass m2<m1 and a net charge z2<z1 after fragmentation by mass spectrometric determination, wherein m1/z1<m2/z2.

The inventors surprisingly found that the here described reagents (compounds) capabling to install multiple permanent charges (either x-times positive charges, y-times negative charges or a (x-y)-times positive and negative charges as net charge) show a fragmentation behavior to one or multiple fragments and bear information for the part of the labeling and the part for the analyte molecule ion after fragmentation. Thus the MS signal enhancement of the analyte results which is, e.g. important for low abundant analytes.

For example, with a two-times permanently charged molecule/compound the m/z value is half of a one-time permanently charged ion (analyte molecule before labeling) of the same analyte. If this multiple times permanently charged molecule, e.g. two-time permanently charged compound, fragments into different-time permanently charged molecules, the fragmentation pathways for the label information goes from higher m/z value precursor to a lower m/z value of the label information as well as from a lower m/z value precursor to a higher m/z value analytic ion (see FIG. 1 and FIG. 6).

By installing a permanently charged label, fragmentation behavior of the molecule is alternated in comparison to the native molecule. After fragmentation of the analyte-label molecule within an MSMS process the permanent charge stays either on the analyte molecule part or the label part. Therefore the quantifying ion to be measured with high intensities can either have molecular information or label information after fragmentation process. To obtain molecular information of the labeled structure a further ion isolation process of the resulted fragment need to be performed which makes the need for an MS3 instrument and which is further lowering the overall sensitivity of the respective scan. The concept of qualifier and quantifier ion described herein cannot be performed if only one permanent charge is installed in the complex or compound because after fragmentation process the resulting ion can either be the label information ion or the analyte information containing ion.

In embodiments of the first aspect of the present invention, the compound for quantitative detection of an analyte using mass spectrometric determination comprises a permanent charge, in particular a permanent net charge, wherein said compound is capable of covalently binding to the analyte, wherein said compound has a mass m1 and a net charge z1, wherein the compound forms at least one daughter ion having a mass m2<m1 and a net charge z2<z1 after fragmentation by mass spectrometric determination, wherein m1/z1<m2/z2.

In embodiments of the first aspect and/or sixth aspect of the present invention, the fragmentation is a one-step process. This can mean that the compound is fragmented into at least one daughter ion directly, without an intermediate step of rearrangements or pseudomolecular ion-species formation.

In embodiments of the first aspect of the present invention, the compound comprises at least two permanent charges, in particular at least two permanent net charges.

In embodiments of the first aspect of the present invention, m1/z1 is at least 60 or more. More than 60 can mean 61, 62, 63, 64, 65, 66, 67, 68, 69, 70, 71, 72, 73, 74 or 75, for example 66 for $C_7H_2ON_2^{2+}$. Alternatively or in addition to m1/z1 is at least 60, m2/z2 is at least 70 or more, for example 74 for $C_4H_{12}N^+$. More than 70 can mean 71, 72, 73, 74, 75, 76, 77, 78, 79 or 80. Additionally, each of m1/z1 and m2/z2 or both can be 1500 as a maximum, e.g. 1300, 1350, 1400, 1450 or 1500. In other words, m1/z1 and/or m2/z2 can be in the range of 60 to 1500 (borders included).

In embodiments of the first aspect of the present invention, the compound is free of a sulfoxide unit (SO). In particular, the compound is free of a sulfoxide unit (SO) to inhibit the neutral loss which enables a preferred fragmentation way from the double charged derivate to a single charged ion. Thus, the fragmentation path, e.g. from a double charged compound to a one time charged compound, is easier without a compound comprising no SO unit compared to a compound having a SO unit.

In embodiments of the first aspect of the present invention, z1 is an integer and is 2 or more than 2. In particular z1 is a positive integer. Positive Integer can mean a whole number and not a fraction, e.g. +2, +3, +4, +5. Alternatively, z1 is a negative integer, e.g. −2, −3, −4, −5. Positive integer, e.g. +2, +3, +4, +5, means in this context that the compound has a double positive net charge z1 in the case of +2 or a triple positive net charge z1 in the case of +3 and so on. Negative integer, e.g. −2, −3, −4, −5, means in this context that the compound has a double negative net charge z1 in the case of −2 or a triple negative net charge z1 in the case of −3 and so on.

This means in the context of the disclosure, by comparison the net charge z2 of the daughter ion and the net charge z1 of the compound, the absolute value of the net charges are crucial. For example, if the compound has a double negative net charge z1 (z1=−2) and the daughter ion has one negative net charge z2 (z2=−1), then the net charge z2 is smaller than the net charge z1 (z2<z1), because the absolute value of the net charge z1 (z1=2) is more than the absolute value of the net charge z2 (z2=1). By comparison the net charges z1 and z2, the absolute values of the net charges are compared instead of the total values.

In embodiments of the first aspect of the present invention, z1 is 2, 3, 4 or 5, preferably z1 is 2. In this context 2 can have the meaning as +2 (2=+2), 3 can have the meaning as +3, 4 can have the meaning as +4 and 5 can have the meaning as +5. Alternatively, in case the compound is negatively charged, 2 can have the meaning as −2 (2=−2), 3 can have the meaning as −3, 4 can have the meaning as −4 and 5 can have the meaning as −5.

In embodiments of the first aspect of the present invention, z2 is smaller than z1. In particular, z2=z1−1, preferably z2 is 1. In this context 1 has the same meaning as +1 or −1.

In embodiments of the first aspect of the present invention, each of z1 and z2 or both are permanently charges, in particular permanently net charges.

In embodiments of the first aspect of the present invention, each of z1 and z2 or both are permanently positive charges, in particular permanently net charges.

In embodiments of the first aspect of the present invention, each of z1 and z2 or both are permanently negative charges, in particular permanently net charges.

In embodiments of the first aspect of the present invention, the net charge z1 is the sum of x-times positive and y-times negative permanently charges of the compound.

In embodiments of the first aspect of the present invention, the net charge z2 is the sum of x-times positive and y-times negative permanently charges of the at least one daughter ion.

In embodiments of the first aspect of the present invention, the compound is capable of forming further daughter ions, which are different from the at least one daughter ion having a mass m2 and a net charge z2. The further daughter ions can be one or two or three or four or five or six or more than six daughter ions. Each of these daughter ions has a mass-to-noise m/z. The m/z values of the further daughter ions can be generally named as mx/zx value with x >4. For example, one further daughter ion has a m5/z5 value, two further daughter ions have m5/z5 and m6/z6 values, three further daughter ions have m5/z5, m6/z7 and m8/z8 values, etc.

In embodiments of the first aspect of the present invention, m/z of the further daughter ions is smaller than m1/z1. In other words, the positon of the peaks of the further daughter ions in the mass spectrum is located left of the peak having the m1/z1 value (parent ion). In contrast to that, the position of the peak of the at least one daughter ion having a m2/z2 value is located right of the parent ion peak. Parent ion peak can be also called base peak. Mostly, the intensity of the base peak is normalized to 100% relative intensity. The normalization can be done because the relative intensities are basically independent from the absolute ion abundances registered by the detector.

In embodiments of the first aspect of the present invention, the compound is capable of forming further daughter ions, each of the further daughter ions comprises a fragment or more fragments of the compound and each having a mx/zx value with x >4, wherein each of the mx/zx value of the further daughter ions is smaller than the m1/z1 value. In particular, the fragments of the compound differ from each other at least by their m/z value.

In embodiments of the first aspect of the present invention, the compound comprises at least three units Z1, Z2, Q and optional a further unit L1, wherein the units are covalently linked to each other, wherein:

Q is a reactive unit capable of forming a covalent bond with the analyte,

Z1 is a charged unit comprising at least one permanently charged moiety, in particular a permanently positive charged moiety or a permanently negative charged moiety, Z2 is a charged unit comprising at least one permanently charged moiety, in particular a permanently positive charged moiety or a permanently negative charged moiety, and L1 is a substituted or non-substituted linker, in particular a cleavable group via fragmentation, e.g. Mc Lafferty fragmentation moiety, Retro Diels Alder fragmentation moiety, benzylic or aliphatic, wherein the net charge of the compound is greater than 1.

In embodiments of the first aspect of the present invention, the compound comprises a reactive unit Q which is capable of reacting with an analyte molecule. The reactive unit Q is capable of reacting with an analyte molecule such that a covalent bond between the compound and the analyte molecule is formed. In embodiments of the first aspect of the present invention, the reactive unit Q forms a covalent bond with the compound. In particular, the covalent bond is formed between the reactive unit of compound and a functional group present in the analyte molecule.

Depending on the functional groups present in the analyte molecule to be determined, the skilled person will select an appropriate reactive unit Q for said compound. It is within common knowledge to decide which reactive unit Q will qualify for binding to a functional group of an analyte of interest.

In embodiments of the first aspect of the present invention, the analyte molecule comprises a functional group selected from the group consisting of carbonyl group, diene group, hydroxyl group, amine group, imine group, ketone group, aldehyde group, thiol group, diol group, phenolic group, epoxide group, disulfide group, nucleobase group, carboxylic acid group, terminal cysteine group, terminal serine group and azide group, each of which is capable of forming a covalent bond with reactive unit Q of compound. Further, it is also contemplated within the scope of the present invention that a functional group present on an analyte molecule would be first converted into another group that is more readily available for reaction with reactive unit Q of compounds.

In embodiments of the first aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the first aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group. Aldoses (aldehyde and keto) exist as acetal and hemiacetals, a sort of masked form of the parent aldehyde/keto.

In embodiments of the first aspect of the present invention, the carbonyl group is an amide group, the skilled person is well aware that the amide group as such is a stable group, but that it can be hydrolyzed to convert the amide group into an carboxylic acid group and an amino group. Hydrolysis of the amide group may be achieved via acid/base catalysed reaction or by enzymatic process either of which is well-known to the skilled person. In embodiments of the first aspect of the present invention, wherein the carbonyl group is a masked aldehyde group or a masked keto group, the respective group is either a hemiacetal group or acetal group, in particular a cyclic hemiacetal group or acetal group. In embodiments of the first aspect of the present invention, the acetal group, is converted into an aldehyde or keto group before reaction with the compound.

In embodiments of the first aspect of the present invention, the carbonyl group is a keto group. In embodiments of the first aspect of the present invention, the keto group may be transferred into an intermediate imine group before reacting with the reactive unit of compounds. In embodiments of the first aspect of the present invention, the analyte molecule comprising one or more keto groups is a ketosteroid. In particular embodiments of the first aspect of the present invention, the ketosteroid is selected from the group consisting of testosterone, epitestosterone, dihydrotestosterone (DHT), desoxymethyltestosterone (DMT), tetrahydrogestrinone (THG), aldosterone, estrone, 4-hydroxyestrone, 2-methoxyestrone, 2-hydroxyestrone, 16-ketoestradiol, 16-alpha-hydroxyestrone, 2-hydroxyestrone-3-methylether, prednisone, prednisolone, pregnenolone, progesterone, dehydroepiandrosterone (DHEA), 17-hydroxypregnenolone, 17-hydroxyprogesterone, androsterone, epiandrosterone, Δ4-androstenedione, 11-deoxycortisol, corticosterone, 21-deoxycortisol, 11-deoxycorticosterone, allopregnanolone and aldosterone.

In embodiments of the first aspect of the present invention, the carbonyl group is a carboxyl group. In embodiments of the first aspect of the present invention, the carboxyl group reacts directly with the compound or it is converted into an activated ester group before reaction with the compound. In embodiments of the first aspect of the present invention, the analyte molecule comprising one or more carboxyl groups is selected from the group consisting of Δ8-tetrahydrocannabinolic acid, benzoylecgonine, salicylic acid, 2-hydroxybenzoic acid, gabapentin, pregabalin, valproic acid, vancomycin, methotrexate, mycophenolic acid, montelukast, repaglinide, furosemide, telmisartan, gemfibrozil, diclofenac, ibuprofen, indomethacin, zomepirac, isoxepac and penicillin. In embodiments of the first aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenyalanine, valine, proline and glycine.

In embodiments of the first aspect of the present invention, the carbonyl group is an aldehyde group. In embodiments of the first aspect of the present invention, the aldehyde group may be transferred into an intermediate imine group before reacting with the reactive unit of compounds. In embodiments of the first aspect of the present invention, the analyte molecule comprising one or more aldehyde groups is selected from the group consisting of pyridoxal, N-acetyl-D-glucosamine, alcaftadine, streptomycin and josamycin.

In embodiments of the first aspect of the present invention, the carbonyl group is an carbonyl ester group. In embodiments of the first aspect of the present invention, the analyte molecule comprising one or more ester groups is selected from the group consisting of cocaine, heroin, Ritalin, aceclofenac, acetylcholine, amcinonide, amiloxate, amylocaine, anileridine, aranidipine artesunate and pethidine.

In embodiments of the first aspect of the present invention, the carbonyl group is an anhydride group. In embodiments of the first aspect of the present invention, the analyte molecule comprising one or more anhydride groups is selected from the group consisting of cantharidin, succinic anhydride, trimellitic anhydride and maleic anhydride.

In embodiments of the first aspect of the present invention, the analyte molecule comprises one or more diene groups, in particular to conjugated diene groups, as functional group. In embodiments of the first aspect of the present invention, the analyte molecule comprising one or more diene groups is a secosteroid. In embodiments, the secosteroid is selected from the group consisting of cholecalciferol (vitamin D3), ergocalciferol (vitamin D2), calcifediol, calcitriol, tachysterol, lumisterol and tacalcitol. In particular, the secosteroid is vitamin D, in particular vitamin D2 or D3 or derivates thereof. In particular embodiments, the secosteroid is selected from the group consisting of vitamin D2, vitamin D3, 25-hydroxyvitamin D2, 25-hydroxyvitamin D3 (calcifediol), 3-epi-25-hydroxyvitamin D2, 3-epi-25-hydroxyvitamin D3, 1,25-dihydroxyvitamin D2, 1,25-dihydroxyvitamin D3 (calcitriol), 24,25-dihydroxyvitamin D2, 24,25-dihydroxyvitamin D3. In embodiments of the first aspect of the present invention, the analyte molecule comprising one or more diene groups is selected from the group consisting of vitamin A, tretinoin, isotretinoin, alitretinoin, natamycin, sirolimus, amphotericin B, nystatin, everolimus, temsirolimus and fidaxomicin.

In embodiments of the first aspect of the present invention, the analyte molecule comprises one or more hydroxyl group as functional group. In embodiments of the first aspect of the present invention, the analyte molecule comprises a single hydroxyl group or two hydroxyl groups. In embodiments wherein more than one hydroxyl group is present, the two hydroxyl groups may be positioned adjacent to each other (1,2-diol) or may be separated by 1, 2 or 3 C atoms (1,3-diol, 1,4-diol, 1,5-diol, respectively). In particular embodiments of the first aspect, the analyte molecule comprises a 1,2-diol group. In embodiments, wherein only one hydroxyl group is present, said analyte is selected from the group consisting of primary alcohol, secondary alcohol and tertiary alcohol. In embodiments of the first aspect of the present invention, wherein the analyte molecule comprises one or more hydroxyl groups, the analyte is selected from the group consisting of benzyl alcohol, menthol, L-carnitine, pyridoxine, metronidazole, isosorbide mononitrate, guaifenesin, clavulanic acid, Miglitol, zalcitabine, isoprenaline, aciclovir, methocarbamol, tramadol, venlafaxine, atropine, clofedanol, alpha-hydroxyalprazolam, alpha-Hydroxytriazolam, lorazepam, oxazepam, Temazepam, ethyl glucuronide, ethylmorphine, morphine, morphine-3-glucuronide, buprenorphine, codeine, dihydrocodeine, p-hydroxypropoxyphene, O-desmethyltramadol, Desmetramadol, dihydroquinidine and quinidine. In embodiments of the first aspect of the present invention, wherein the analyte molecule comprises more than one hydroxyl groups, the analyte is selected from the group consisting of vitamin C, glucosamine, mannitol, tetrahydrobiopterin, cytarabine, azacitidine, ribavirin, floxuridine, Gemcitabine, Streptozotocin, adenosine, Vidarabine, cladribine, estriol, trifluridine, clofarabine, nadolol, zanamivir, lactulose, adenosine monophosphate, idoxuridine, regadenoson, lincomycin, clindamycin, Canagliflozin, tobramycin, netilmicin, kanamycin, ticagrelor, epirubicin, doxorubicin, arbekacin, streptomycin, ouabain, amikacin, neomycin, framycetin, paromomycin, erythromycin, clarithromycin, azithromycin, vindesine, digitoxin, digoxin, metrizamide, acetyldigitoxin, deslanoside, Fludarabine, clofarabine, gemcitabine, cytarabine, capecitabine, vidarabine, and plicamycin.

In embodiments of the first aspect of the present invention, the analyte molecule comprises one or more thiol group (including but not limited to alkyl thiol and aryl thiol groups) as functional group. In embodiments of the first aspect of the present invention, the analyte molecule comprising one or more thiol groups is selected from the group consisting of thiomandelic acid, DL-captopril, DL-thiorphan, N-acetylcysteine, D-penicillamine, glutathione, L-cysteine, zofenoprilat, tiopronin, dimercaprol, succimer.

In embodiments of the first aspect of the present invention, the analyte molecule comprises one or more disulfide group as functional group. In embodiments of the first aspect of the present invention, the analyte molecule comprising one or more disulfide groups is selected from the group consisting of glutathione disulfide, dipyrithione, selenium sulfide, disulfiram, lipoic acid, L-cystine, fursultiamine, octreotide, desmopressin, vapreotide, terlipressin, linaclotide and peginesatide. Selenium sulfide can be selenium disulfide, $SeS_2$, or selenium hexasulfide, $Se_2S_6$.

In embodiments of the first aspect of the present invention, the analyte molecule comprises one or more epoxide group as functional group. In embodiments of the first aspect of the present invention, the analyte molecule comprising one or more epoxide groups is selected from the group consisting of Carbamazepine-10,11-epoxide, carfilzomib, furosemide epoxide, fosfomycin, sevelamer hydrochloride, cerulenin, scopolamine, tiotropium, tiotropium bromide, methylscopolamine bromide, eplerenone, mupirocin, natamycin, and troleandomycin.

In embodiments of the first aspect of the present invention, the analyte molecule comprises one or more phenol groups as functional group. In particular embodiments of the first aspect of the present invention, analyte molecules comprising one or more phenol groups are steroids or steroid-like compounds. In embodiments of the first aspect of the present invention, the analyte molecule comprising one or more phenol groups is a steroid or a steroid-like compound having an A-ring which is $sp^2$ hybridized and an OH group at the 3-position of the A-ring. In particular embodiments of the first aspect of the present invention, the steroid or steroid-like analyte molecule is selected from the group consisting of estrogen, estrogen-like compounds, estrone (E1), estradiol (E2), 17a-estradiol, 17b-estradiol, estriol (E3), 16-epiestriol, 17-epiestriol, and 16, 17-epiestriol and/or metabolites thereof. In embodiments, the metabolites are selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHE1), 2-methoxyestrone (2-MeOE1), 4-methoxyestrone (4-MeOE1), 2-hydroxyestrone-3-methyl ether (3-MeOE1), 2-methoxyestradiol (2-MeOE2), 4-methoxyestradiol (4-MeOE2), 2-hydroxyestrone (2-OHE1), 4-hydroxyestrone (4-OHE1), 2-hydroxyestradiol (2-OHE2), estrone (E1), estrone sulfate (E1s), 17a-estradiol (E2a), 17b-estradiol (E2B), estradiol sulfate (E2S), equilin (EQ), 17a-dihydroequilin (EQa), 17b-dihydroequilin (EQb), Equilenin (EN), 17-dihydroequilenin (ENa), 17α-dihydroequilenin, 17β-dihydroequilenin (ENb), A8,9-dehydroestrone (dEl), Δ8,9-dehydroestrone sulfate (dEls), Δ9-tetrahydrocannabinol, mycophenolic acid. β or b can be used interchangeable. α and a can be used interchangeable.

In embodiments of the first aspect of the present invention, the analyte molecule comprises an amine group as functional group. In embodiments of the first aspect of the present invention, the amine group is an alkyl amine or an aryl amine group. In embodiments of the first aspect of the present invention, the analyte comprising one or more amine groups is selected from the group consisting of proteins and peptides. In embodiments of the first aspect of the present invention, the analyte molecule comprising an amine group is selected from the group consisting of 3,4-methylenedioxyamphetamine, 3,4-methylenedioxy-N-ethylamphetamine, 3,4-methylenedioxymethamphetamine, Amphetamine, Methamphetamine, N-methyl-1,3-benzodioxolylbutanamine, 7-aminoclonazepam, 7-aminoflunitrazepam, 3,4-dimethylmetheathinone, 3-fluoromethcathinone, 4-methoxymethcathinone, 4-methylethcathinone, 4-methylmethcathinone, amfepramone, butylone, etheathinone, elephedrone, methcathinone, methylone, methylenedioxypyrovalerone, benzoylecgonine, dehydronorketamine, ketamine, norketamine, methadone, normethadone, 6-acetylmorphine, diacetylmorphine, morphine, norhydrocodone, oxycodone, oxymorphone, phencyclidine, norpropoxyphene, amitriptyline, clomipramine, dothiepin, doxepin, imipramine, nortriptyline, trimipramine, fentanyl, glycylxylidide, lidocaine, monoethylglycylxylidide, N-acetylprocainamide, procainamide, pregabalin, 2-Methylamino-1-(3,4-methylendioxyphenyl)butan, N-methyl-1,3-benzodioxolylbutanamine, 2-Amino-1-(3,4-methylendioxyphenyl)butan, 1,3-benzodioxolylbutanamine, normeperidine, O-Destramadol, desmetramadol, tramadol, lamotrigine, Theophylline, amikacin, gentamicin, tobramycin, vancomycin, Methotrexate, Gabapentin sisomicin and 5-methylcytosine.

In embodiments of the first aspect of the present invention, the analyte molecule is a carbohydrate or substance having a carbohydrate moiety, e.g. a glycoprotein or a nucleoside. In embodiments of the first aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneuraminic acid, etc. In embodiments, the analyte molecule is an oligosaccharide, in particular selected from the group consisting of a disaccharide, trisaccharide, tetrasaccharide, polysaccharide. In embodiments of the first aspect of the present invention, the disaccharide is selected from the group consisting of sucrose, maltose and lactose. In embodiments of the first aspect of the present invention, the analyte molecule is a substance comprising above described mono-, di-, tri-, tetra-, oligo- or polysaccharide moiety.

In embodiments of the first aspect of the present invention, the analyte molecule comprises an azide group as functional group which is selected from the group consisting of alkyl or aryl azide. In embodiments of the first aspect of the present invention, the analyte molecule comprising one or more azide groups is selected from the group consisting of zidovudine and azidocillin.

Such analyte molecules may be present in biological or clinical samples such as body liquids, e.g. blood, serum, plasma, urine, saliva, spinal fluid, etc., tissue or cell extracts, etc. In embodiments of the first aspect of the present invention, the analyte molecule(s) are present in a biological or clinical sample selected from the group consisting of blood, serum, plasma, urine, saliva, spinal fluid, and a dried blood spot. In some embodiments of the first aspect of the present invention, the analyte molecules may be present in a sample which is a purified or partially purified sample, e.g. a purified or partially purified protein mixture or extract.

In embodiments of the first aspect of the present invention, the reactive unit Q is selected from the group consisting of a carbonyl reactive unit, a diene reactive unit, a hydroxyl reactive unit, an amino reactive unit, an imine reactive unit, a thiol reactive unit, a diol reactive unit, a phenol reactive unit, an epoxide reactive unit, a disulfide reactive unit, and an azido reactive unit.

In embodiments of the first aspect of the present invention, the reactive unit Q is a carbonyl reactive unit, which is capable of reacting with any type of molecule having a carbonyl group. In embodiments of the first aspect of the present invention, the carbonyl reactive unit is selected from the group consisting of carboxyl reactive unit, keto reactive unit, aldehyde reactive unit, anhydride reactive unit, carbonyl ester reactive unit, and imide reactive unit. In embodiments of the first aspect of the present invention, the carbonyl-reactive unit may have either a super-nucleophilic N atom strengthened by the α-effect through an adjacent O or N atom NH2-N/O or a dithiol molecule.

In embodiments of the first aspect of the present invention, the carbonyl-reactive unit is selected from the group consisting of (i) a hydrazine unit, e.g. a $H_2N$—NH—, or $H_2N$—NR1-unit, wherein R1 is aryl or C1-4 alkyl, particularly C1 or C2 alkyl, optionally substituted,
(ii) a hydrazide unit, in particular a carbo-hydrazide or a sulfohydrazide, in particular a $H_2N$—NH—C(O)—, or $H_2N$—NR2-C(O)— unit, wherein R2 is aryl or C1-4 alkyl, particularly C1 or C2 alkyl, optionally substituted,
(iii) a hydroxylamino unit, e.g. a $H_2N$—O— unit, and
(iv) a dithiol unit, particularly a 1,2-dithiol or 1,3-dithiol unit.

In embodiments of the first aspect of the present invention, wherein the carbonyl reactive unit is a carboxyl reactive unit, the carboxyl reactive units reacts with carboxyl groups on an analyte molecule. In embodiment of the first aspect of the present invention, the carboxyl reactive unit is selected from the group consisting of a diazo unit, an alkylhalide, amine, and hydrazine unit.

In embodiments of the first aspect of the present invention, analyte molecule comprises an ketone or aldehyde group and Q is a carbonyl reactive unit, which is selected from the group:

(i) a hydrazine unit,
(ii) a hydrazide unit,
(iii) a hydroxylamino unit, and
(iv) a dithiol unit.

In embodiments of the first aspect of the present invention, the reactive unit Q is a diene reactive unit, which is capable of reacting with an analyte comprising a diene group. In embodiments of the first aspect of the present invention, the diene reactive unit is selected from the group consisting of Cookson-type reagents, e.g. 1,2,4-triazoline-3,5-diones, which are capable to act as a dienophile.

In embodiments of the first aspect of the present invention, the reactive unit Q is a hydroxyl reactive unit, which is capable of reacting with an analyte comprising a hydroxyl group. In embodiments of the first aspect of the present invention, the hydroxyl reactive units is selected from the group consisting of sulfonylchlorides, activated carboxylic esters (NHS, or imidazolide), and fluoro aromates/heteroaromates capable for nucleophilic substitution of the fluorine (T. Higashi J Steroid Biochem Mol Biol. 2016 September; 162:57-69). In embodiments of the first aspect of the present invention, the reactive unit Q is a diol reactive unit which reacts with an diol group on an analyte molecule. In embodiments of the first aspect of the present invention, wherein the reactive unit is a 1,2 diol reactive unit, the 1,2 diol reactive unit comprises boronic acid. In further embodiments, diols can be oxidised to the respective ketones or aldehydes and then reacted with ketone/aldehyde-reactive units K.

In embodiments of the first aspect of the present invention, the amino reactive unit reacts with amino groups on an analyte molecule. In embodiments of the first aspect of the present invention, the amino-reactive unit is selected from the group consisting of active ester group such as N-hydroxy succinimide (NHS) ester or sulfo-NHS ester, pentafluoro phenyl ester, cabonylimidazole ester, quadratic acid esters, a hydroxybenzotriazole (HOBt) ester, 1-hydroxy-7-azabenzotriazole (HOAt) ester, and a sulfonylchloride unit.

In embodiments of the first aspect of the present invention, the thiol reactive unit reacts with an thiol group on an analyte molecule. In embodiments of the first aspect of the present invention, the thiole reactive unit is selected from the group consisting of haloacetyl group, in particular selected from the group consisting of Br/I—$CH_2$—C(═O)— unit, acrylamide/ester unit, unsaturated imide unit such as maleimide, methylsulfonyl phenyloxadiazole and sulfonylchloride unit.

In embodiments of the first aspect of the present invention, the phenol reactive unit reacts with phenol groups on an analyte molecule. In embodiments of the first aspect of the present invention, the phenol-reactive unit is selected from the group consisting of active ester unit such as N-hydroxy succinimide (NHS) ester or sulfo-NHS ester, pentafluoro phenyl ester, carbonylimidazole ester, quadratic acid esters, a hydroxybenzotriazole (HOBt) ester, 1-hydroxy-7-azabenzotriazole (HOAt) ester, and a sulfonylchloride unit. Phenol groups present on an analyte molecule can be reacted with highly reactive electrophiles like triazolinedione (like TAD) via a reaction (H. Ban et al J. Am. Chem. Soc., 2010, 132 (5), pp 1523-1525) or by diazotization or alternatively by ortho nitration followed by reduction to an amine which could then be reacted with an amine reactive reagent. In embodiments of the first aspect of the present invention, the phenol-reactive unit is fluoro-1-pyridinium.

In embodiments of the first aspect of the present invention, the reactive unit Q is a epoxide reactive unit, which is capable of reacting with an analyte comprising a epoxide group. In embodiments of the first aspect of the present invention, the epoxide reactive unit is selected from the group consisting of amino, thiol, super-nucleophilic N atom strengthened by the α-effect through an adjacent O or N atom NH2-N/O molecule. In embodiments of the first aspect of the present invention, the epoxide reactive unit is selected from the group:

(i) a hydrazine unit, e.g. a $H_2N$—NH—, or $H_2N$—$NR^1$— unit, wherein $R^1$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy,
(ii) a hydrazide unit, in particular a carbo-hydrazide or sulfo-hydrazide unit, in particular a $H_2N$—NH—C(O)—, or $H_2N$—$NR^2$—C(O)— unit,
  wherein $R^2$ is aryl, aryl containing one or more heteroatoms or $C_{1-4}$ alkyl, particularly C1 or $C_2$ alkyl, optionally substituted e.g. with halo, hydroxyl, and/or $C_{1-3}$ alkoxy, and
(iii) a hydroxylamino unit, e.g. a $H_2N$—O— unit.

In embodiments of the first aspect of the present invention, the reactive unit Q is a disulfide reactive unit, which is capable of reacting with an analyte comprising a disulfide group. In embodiments of the first aspect of the present invention, the disulfide reactive unit is selected from the group consisting of thiol. In further embodiments, disulfide group can be reduced to the respective thiol group and then reacted with thiol reactive units Q.

In embodiments of the first aspect of the present invention, the reactive unit Q is a thiol-reactive group or is an amino-reactive group such as an active ester group, e.g. N-hydroxysuccinimide (NHS) ester or sulpho-NHS ester, a hydroxybenzotriazole (HOBt) ester or 1-hydroxy-7-azabenzotriazole (HOAt) ester group.

In embodiments of the first aspect of the present invention, the reactive unit Q is selected from 4-substituted 1,2,4-triazolin-3,5-dione (TAD), 4-Phenyl-1,2,4-triazolin-3,5-dion (PTAD) or fluoro-substituted pyridinium.

In embodiments of the first aspect of the present invention, the reactive unit Q is a azido reactive unit which reacts with azido groups on an analyte molecule. In embodiments of the first aspect of the present invention, the azido-reactive unit reacts with azido groups through azide-alkyne cycloaddition. In embodiments of the first aspect of the present invention, the azido-reactive unit is selected from the group consisting of alkyne (alkyl or aryl), linear alkyne or cyclic alkyne. The reaction between the azido and the alkyne can proceed with or without the use of a catalyst. In further embodiments of the first aspect of the present invention the azido group can be reduced to the respective amino group and then reacted with amino reactive units K.

In embodiments of the first aspect of the present invention, the functional group of the analyte is selected from the options mentioned in the left column of the table 1. The reactive group of Q of the corresponding functional group of the analyte is selected from the group mentioned in the right column of table 1.

TABLE 1

Functional group of the analyte and reactive groups for the specific labels

| Functional group of the analyte | Reactive group |
|---|---|
| Amine | Active ester with NHS leaving group, pentafluorophenyl ester, squaric acid esters, sulfonyl chloride, ketone or aldehyde (reductive amination) |
| Thiol | Maleimide, iodoacetyl, methyl sulfonyl phenyl oxadiazole |
| Diol | Boronic acid (or oxidation to ketone or aldehyde) |
| Ketone, aldehyde | O-substituted hydroxylamine, hydrazines, hydrazides. |
| Diene | Dienophiles, triazolinedione (TAD) |
| Phenoles | Ene reaction triazolinedione (TAD), ortho nitration/reduction, diazo formation/nucleophilic substitution. Active ester with NHS leaving group, pentafluorophenyl ester, squaric acid esters, sulfonyl chloride, fluoro-1-pyridinium. |
| Nucleobase | Chloro acetyl/Pt complexes |
| Unspecific | Azide (Nitrene) |
| Carboxylic acids | ED AC activation => amine Base/alkyl halide Chloroformate/alcohol Diazoalkane |
| Terminal cysteine | Hetero aryl/Aryl cyanides |
| Terminal serine | Oxidation (followed by aldehyde reactive reagents) |

In embodiments of the first aspect of the present invention, the compound comprises two charged units, named as Z1 and Z2. Z1 is a charged unit comprising at least one permanently charged moiety, in particular a permanently positive charged moiety or a permanently negative charged moiety. Z2 is a charged unit comprising at least one permanently charged moiety, in particular a permanently positive charged moiety or a permanently negative charged moiety.

In embodiments of the first aspect of the present invention, the charged unit Z1 and/or Z2 is permanently charged, in particular under neutral conditions, in particular at a pH value of 6-8.

In embodiments of the first aspect of the present invention, each of the charged units Z1 and Z2 comprises or consists of (i) at least one or exact one positively charged moiety. Alternatively each of the charged units Z1 and Z2 comprises or consists of (ii) at least one or exact one negatively charged moiety. The compound comprises a net charge z1 of 2 or more than 2, e.g. 3, 4 or 5.

In embodiments of the first aspect of the present invention, Z1 and Z2 are separated from each other by at least one atom, e.g. a C atom.

In embodiments of the first aspect of the present invention, the charged unit Z1 or the charged unit Z2 or both is a positively charged unit. In embodiments of the first aspect of the present invention, the positively charged unit Z1 and/or Z2, is chosen in a manner that the resulting compound has a pKa of 10 or higher, more particularly has a pKa of 12 or higher. In embodiments of the first aspect of the present invention, the positively charged unit Z1 and/or Z2 is selected from the group consisting of primary, secondary, tertiary or quaternary ammonium, sulfonium, imidazolium, pyridinium, or a phosphonium. In particular embodiments of the first aspect, the positively charged moiety is tri-methyl-ammonium, N,N-dimethyl-piperidinium or N-alkyl-quinuclidinium.

In embodiments of the first aspect of the present invention, the charged unit Z1 or the charged unit Z2 or both is a negatively charged unit. In embodiments of the first aspect of the present invention, the negatively charged unit Z1 and/or Z2 is chosen in a manner that the resulting compound has a pKb of 10 or higher, more particularly has a pKb of 12 or higher. In embodiments of the first aspect of the present invention, the negatively charged unit Z1 and/or Z2 is selected from the group consisting of a phosphate, sulphate, sulphonate or carboxylate.

In embodiments of the first aspect of the present invention, L1 is a substituted linker or non-substituted linker, in particular a cleavable group via fragmentation, e.g. Mc Lafferty fragmentation moiety, Retro Diels Alder fragmentation moiety or aliphatic. In embodiments of the first aspect of the present invention, L1 is not protonatable. In embodiments of the first aspect, the L1 comprises 3 to 30 C-atoms, in particular 5-20 C-atoms, in particular 8-16 C-atoms. In embodiments, L1 comprises 1 or more heteroatoms, in particular N, O or S. In embodiments of the first aspect of the present invention, L1 comprises at least four heteroatoms, in particular five, six, or seven heteroatoms, in particular N and/or O. In embodiments of the first aspect of the present invention, L1 comprises five heteroatoms, in particular three O-atoms and two N-atoms.

In embodiments of the first aspect of the present invention, the linker L1 comprises 1 to 10 C-atoms, optionally comprising 1 or more heteroatoms.

In embodiments of the first aspect of the present invention, the linker L1 is selected from the group consisting of McLafferty fragmentation unit, Retro Diels alder unit, neutral loss cleaving unit, bond dissociation unit, alpha-cleavage and charge site rearrangements.

McLafferty fragmentation unit is a carbonyl compound containing at least one gamma hydrogen.

Retro Diels alder unit is a dials alder reaction product.

In embodiments of the first aspect of the present invention, the neutral loss cleaving unit releases at least one neutral entity upon ionization. The neutral entity is a low molecular weight neutral entity, in particular in a range of 10-100 Da, in particular 20-80 Da, in particular 25-65 Da. In particular, the neutral entity has a molecular weight of 100 Da or less, in particular of 80 Da or less, in particular of 70 Da or less, in particular of 50 Da or less, in particular of 30 Da or less.

In embodiments of the first aspect of the present invention, the neutral entity is selected from the group consisting of $N_2$, NO, $NO_2$, $S_2$, SO, $SO_2$, CO, $CO_2$. In particular embodiments, the neutral entity is $N_2$.

In embodiments of the first aspect of the present invention, the loss of the neutral entity leads to a reduction of the mass/charge ratio (m/z) by −28 Da (in case $N_2$ or CO is lost), −30 Da (in case NO is lost), −44 Da (in case $CO_2$ is lost), −46

Da (in case $NO_2$ is lost), −48 Da (in case SO is lost), or −64 Da (in case $S_2$ or $SO_2$ is lost).

In embodiments of the first aspect of the present invention, one neutral entity is released. In embodiments of the first aspect of the present invention, two neutral entities are released. In particular, the second released neutral entity is different from the first released neutral entity. The release of the second neutral entity occurs concurrently or subsequently to the release of the first neutral entity. In particular, the release of the second neutral entity occurs concurrently to the release of the first neutral entity, i.e. both neutral entity are released at once, i.e in one single fragmentation event.

In embodiments of the first aspect of the present invention, the neutral loss cleaving unit comprises or consists of a cyclic moiety which is capable of fragmentation. In embodiments of the first aspect of the present invention, the neutral loss cleaving unit comprises or consists of a heterocyclic moiety, particularly a 4-, 5- or 6-membered heterocyclic moiety, which is capable of fragmentation, in particular by a reverse cycloaddition reaction. In embodiments of the first aspect of the present invention, the neutral loss cleaving unit comprises or consists of a 4-, 5- or 6-membered heterocyclic moiety, particularly a 5-membered heterocyclic moiety, having at least 2 heteroatoms adjacent to each other, in particularly two N atoms adjacent to each other. In embodiments of the first aspect of the present invention, the neutral loss cleaving unit comprises or consists of triazole, tetrazole, oxadiazole, thiadiazole moiety or a hydrogenated derivative thereof. In embodiments of the the first aspect of the present invention, the neutral loss cleaving unit comprises or consists a 1,2,3-triazole, 1,4,5-triazol, 3,4,5-triazol moiety or a 2,3,4,5-tetrazole or a 2,3,5,6 tetrazole moiety.

Bond dissociation unit is, e.g., a chemical bond which is capable to dissociate in charged species under mass spectrometry conditions.

Alpha-cleavage is, e.g., a carbon carbon bond adjacent to a specific functional group.

Charge site rearrangements are electrons from the bond adjacent to the charged-bearing atom migrate to that atom, neutralizing the original charge and causing it to move to a different site.

In embodiments of the first aspect of the present invention, Q is covalently linked to Z1 or Z2. In particular, Q is directly linked to Z1 or directly linked to Z2 according.

In embodiments of the first aspect of the present invention, L1 covalently links Z1 and Z2. In particular, L1 is directly linked to Z1 and directly linked to Z2 according to the formula: Z1-L1-Z2.

In embodiments of the first aspect of the present invention, the compound is fragmented between Z1 and Z2. In particular, the compound is fragmented by cleavage of the linker L1.

In embodiments of the first aspect of the present invention, the compound comprises one of the following formulae 1-I to 1-III:

$$(Z1—L1—Z2—Q)^N \text{ with } N \geq 1, \quad (1\text{-I})$$

$$(Q—Z1—L1—Z2)^N \text{ with } N \geq 1, \quad (1\text{-II})$$

$$(Z1—Z2—Q)^N \text{ with } N \geq 1. \quad (1\text{-III})$$

In this context "N" means the net charge of the compound.

In the context of the disclosure mentioned below and/or above "N≥1" means that N is greater than or equal to +1 (plus one). In addition or alternatively "N≥1" means that N is greater than or equal to −1 (minus one).

In embodiments of the first aspect of the present invention, the compound comprises formula 1-I and is selected from the following group:

Label 1

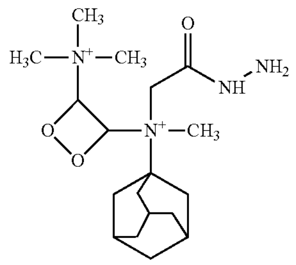

Label 2

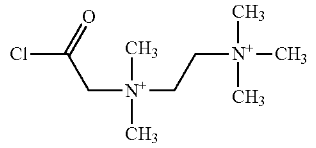

Label 3

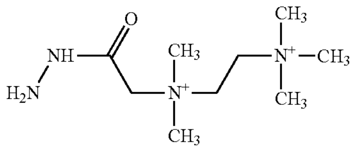

Label 4

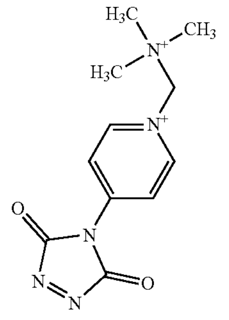

Label 5

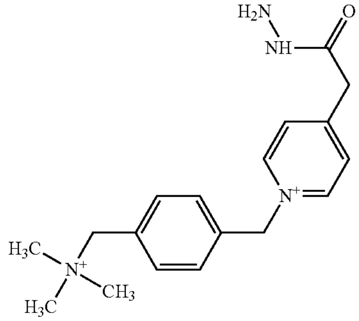

The example of these embodiments are double charged, particularly double positive charged.

In embodiments of the first aspect of the present invention, Z1 and Z2 comprise independently of each other a chelate complex, phosphonium, ammonium, carbenium, pyridinium, sulphonium, charged heterocycles of 3-10 membered rings containing either N, S, H, and C-Atoms or derivatives thereof.

In embodiments of the first aspect of the present invention, the compound comprises formula 1-IV: $(Z1\text{-}(L1\text{-}Z2)_M\text{-}(L2\text{-}Zo)_K\text{-}Q)^N$, wherein:

Zo is a charged unit, in particular comprising either a positive or a negative or a neutral charged unit, L2 is a substituted or non-substituted linker, in particular L2 is L1 or L2 is a cleavable group via fragmentation, and M >0, K >0 and N >1. L1, Z1, Z2 and Q have the same meaning as mentioned above.

In this context "N" means the net charge of the compound. In particular, N=M+1 (−1) if Zo=O or N=M+1 (−1)−K if Zo is charged.

In embodiments of the first aspect of the present invention, Zo is a charged unit. Zo can be selected from the group consisting of primary, secondary, tertiary or quaternary ammonium, carbenium, sulfonium, imidazolium, pyridinium, charged heterocycles of 3-10 membered rings containing either N, S, H, and C-Atoms or derivatives thereof, chelate complex or phosphonium. In particular embodiments of the first aspect, the positively charged moiety is tri-methyl-ammonium, N,N-dimethyl-piperidinium or N-alkyl-quinuclidinium.

In embodiments of the first aspect of the present invention, L2 is a substituted linker or non-substituted linker. L2 can be a cleavable group via fragmentation, e.g. Mc Lafferty fragmentation moiety, Retro Diels Alder fragmentation moiety, benzylic or aliphatic.

In embodiments of the first aspect of the present invention, M is 0, 1, 2, 3, 4 or 5.

In embodiments of the first aspect of the present invention, K is 0, 1, 2, 3, 4 or 5.

In embodiments of the first aspect of the present invention, the compound comprises formula 1-IV with M=1 and K=1. For example, the compound is selected from the following group:

Label 6

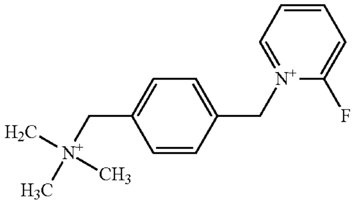

Label 7

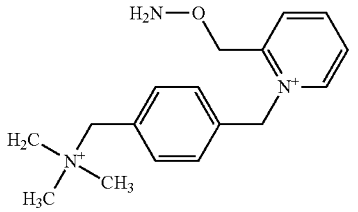

In embodiments of the first aspect of the present invention, the compound comprises formula 1-V: $(Z1\text{-}(L3\text{-}Z2)_M\text{-}(L2\text{-}Zo)_K\text{-}Q)^N$, wherein:

Zo is a charged unit, in particular comprising either a positive or a negative or a neutral charged unit, in particular the charged unit comprises either a positive or a negative charged unit, L2 is a substituted or non-substituted linker, in particular L2 is L1 or L2 is a cleavable group via fragmentation, L3 is a substituted or non-substituted linker, in particular a non-cleavable group via fragmentation, e.g. benzylic or diazo, M>0, K>0 and N≥1. L1, Z1, Z2 and Q have the same meaning as mentioned above.

In embodiments of the first aspect of the present invention, L3 is a substituted or non-substituted linker. L3 is selected from the group consisting of a cleavable group via fragmentation, e.g. Mc Lafferty fragmentation moiety, Retro Diels Alder fragmentation moiety, benzylic or aliphatic. Alternatively, L3 is in particular a non-cleavable group via fragmentation, e.g. benzylic, diazo or aliphatic group consisting of at least one or two carbon atoms (C1-C2) and aliphatic group consisting of C1-C2.

In embodiments of the first aspect of the present invention, the compound comprises formula 1-V with M=1 and K=1. For example, the compound is selected from label 6 or label 7.

In embodiments of the first aspect of the present invention, the compound comprises formula 1-VI: $((Z1)_M\text{-}L1\text{-}Z2\text{-}(L2/L3)_K\text{-}Zo)^N\text{-}Q$, wherein:

Zo is a charged unit, in particular comprising either a positive or a negative or a neutral charged unit, L2 is a substituted or non-substituted linker, in particular L2 is L1 or L2 is a cleavable group via fragmentation, L3 is a substituted or non-substituted linker, in particular a non-cleavable group via fragmentation, e.g. benzylic or diazo, M >0, K >0 and N >1. L1, Z1, Z2 and Q have the same meaning as mentioned above.

In embodiments of the first aspect of the present invention, the compound comprises formula 1-VI and is Label 8

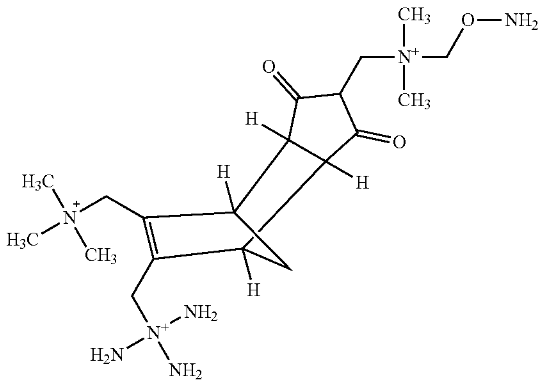

In embodiments of the first aspect of the present invention, the compound comprises formula 1-VII: $(Z1\text{-}L1\text{-}Z2\text{-}Q)^N$, wherein: N≥1. L1, Z1, Z2 and Q have the same meaning as mentioned above.

In embodiments of the first aspect of the present invention, the compound comprises formula 1-VIII:

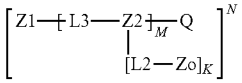

wherein:

Zo is a charged unit comprising, in particular either a positive or a negative or a neutral charged unit, L2 is a substituted or non-substituted linker, in particular L2 is L1 or L2 is a cleavable group via fragmentation, L3 is a substituted or non-substituted linker, in particular a non-cleavable group via fragmentation, e.g. benzylic or diazo, N>1, M>0 and K>0. Z1, Z2 and Q have the same meaning as mentioned above.

In embodiments of the first aspect of the present invention, the compound comprises formula 1-IX:

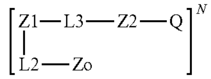

wherein:

Zo is a charged unit, in particular comprising either a positive or a negative or a neutral charged unit, L2 is a substituted or non-substituted linker, in particular L2 is L1 or L2 is a cleavable group via fragmentation, L3 is a substituted or non-substituted linker, in particular a non-cleavable group via fragmentation, e.g. benzylic or diazo, and N≥1. Z1, Z2 and Q have the same meaning as mentioned above.

In embodiments of the first aspect of the present invention, the compound comprises formula 1-IX and is selected from:

Label 9

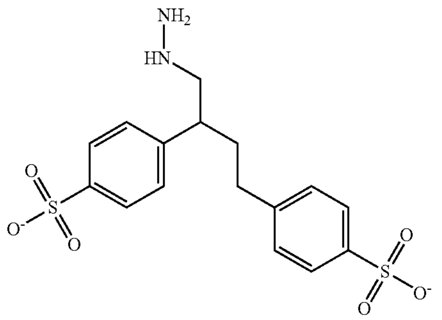

Label 10

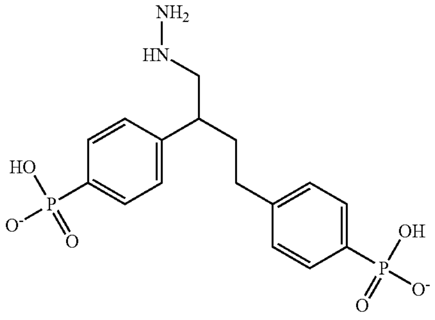

Labels 9 and 10 are negative double charged.

In embodiments of the first aspect of the present invention, the compound comprises formula 1-X:

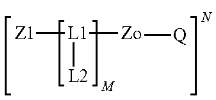

wherein:

Zo is a charged unit comprising, in particular either a positive or a negative or a neutral charged unit, N≥1 and M>0. L1, Z1, Z2 and Q have the same meaning as mentioned above.

In embodiments of the first aspect of the present invention, the compound comprises formula 1-XI:

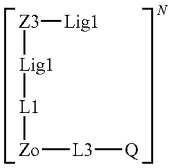

wherein:

Zo is a charged unit comprising, in particular either a positive or a negative or a neutral charged unit, Z3 is a multiple charged unit, in particular a multiple charged metal unit, L3 is a substituted or non-substituted linker, in particular a non-cleavable group via fragmentation, e.g. benzylic, diazo or aliphatic group consisting of at least one or two carbon atoms (C1-C2) and aliphatic group consisting of C1-C2.

Lig1 is a multiple charged metal complex binding ligand, in particular depended with high binding constant log Kb>5, and N≥1. L1 and Q have the same meaning as mentioned above.

In embodiments of the first aspect of the present invention, Lig1 is a multiple charged metal complex binding ligand and is selected from the following group: acetylacetonate (acac), 2-(2-aminoethylamino)ethanol, 2,2'-bis(diphenylphosphino)-6,6'-dimethoxy-1,1'-biphenyl, 2,2'-bis(diphenylphosphino)-1,1'-binapthyl, 1,2-bis[4,5-dihydro-3H-binaphtho[1,2-c:2',1'-e]phosphepine]benzene (BINAPHANE), 1,1'-bi-2-naphthol (BINOL), 5,5'-di-tert-butyl-2,2'-bipyridine, bis(oxazolin) ligands (BOX), 2,2'-bipyridine, bis(diphenylphosphino)butane, 1,5-cyclooctadiene, benzyl(methyl)phenylphosphine, 1,2-bis(2,5-diethylphosphono)ethane, tert-butoxycarbonyl-4-diphenylphosphino-2-(diphenylphosphinomethyl) pyrrolidine, bis(4-isopropyl-4,5-dihydrooxazol-2-yl) phenylamine (bopa-ip), 1,4,7,10-tetraazacyclododecane-1,4,7,10-tetraacetic acid (DOTA), N-heterocyclic carbenes, 1,10-phenanthroline, porphin, terpyridine (terpy), triphenylphosphine, 1,2-bis(o-aminophenoxy)ethane-N,N,N',N'-tetraacetic acid (BAPTA), bis(diphenylphosphino)methane (dppm), 1,2-bis(diphenylphosphino)ethane (dppe), 1,3-bis(diphenylphosphino)propane (dppp), crown ethers, [2.2.2] cryptand, cyclopentadienyl anion, diethylenetriaminepentaacetic acid (DTPA), ethylenediaminetetraacetic acid (EDTA), ethylenediaminotriacetate (TED), ethylenebis(oxyethylenenitrilo)tetraacetate (egta4-), iminodiacetic acid (IDA), nitrilotriacetic acid (NTA), tris(o-tolyl)phosphine, tris(2-aminoethyl)amine, cyclohexyl-o-anisylmethylphosphine (CAMP), phenyl-o-anisylmethylphosphine (PAMP), tropylium ion, citrate, cyclooctene, cyclooctatetraene (COT), cyclopentadienyl ion (Cp), 1,2,3,4,5-pentamethylcyclopentadienyl ion (Cp*), 1,4-diazabicyclo[2.2.2]octane (DABCO), dibenzylideneacetone (dba), 4-dimethylaminopyridine (DMAP), neocuproin, bis(2,5-dimethylphospholano)benzene, (3,5-dioxa-4-phosphacyclohepta[2,1-a;3,4-a'] dinapthalen-4-yl)dimethylamine (MonoPhos), 1,3-diketiminate ligands, bicyclo[2.2.1]hepta-2,5-diene, acetate, oxalate, 8-hydroxyquinoline, phthalocyanine, picolylamine, 2-phenylpyridine, pyrazine, salen ligands, 1,4,7-triazacyclononane (TACN), tartrate, trispyrazolylborate, tetraphenylporphyrin (TPP), 3,3',3"-phosphanetriyltris(benzenesulfonic acid) trisodium salt (tppts), 5-(3-pyridyl)-1H-tetrazole, 2-(1H-imidazol-2-yl)pyridine, 2-(1H-1,2,4-triazol-3-yl)pyridine, picoline, 2, 2'-bipyridine-4-butanoic acid.

In embodiments of the first aspect of the present invention, the compound comprises formula 1-XI is Label 11

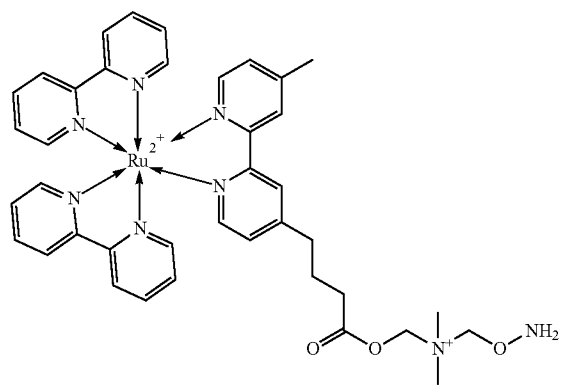

In embodiments of the first aspect of the present invention, the compound comprises formula 1-XII:

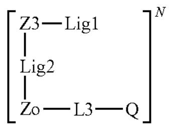

wherein:

Zo is a charged unit comprising, in particular either a positive or a negative or a neutral charged unit, Z3 is a multiple charged unit, in particular a multiple charged metal unit, L3 is a substituted or non-substituted linker, in particular a non-cleavable group via fragmentation, e.g. benzylic or diazo, Lig1 is a multiple charged metal complex binding ligand, in particular depended with a binding constant log $K_B$>5

Lig2 is a multiple charged metal complex binding ligand, in particular depended with a binding constant: 1≤log $K_B$≤5 and N≥1. Q has the same meaning as mentioned above.

In embodiments of the first aspect of the present invention, Lig1 is present 2 times in the complex.

In embodiments of the first aspect of the present invention, Lig1 is equal to Lig2.

In embodiments of the first aspect of the present invention, Lig1 can be selected from the group as mentioned above.

In embodiments of the first aspect of the present invention, Lig2 is a multiple charged metal complex binding ligand. Lig2 can be selected from the following group: 2-(2-aminoethylamino)ethanol, 1,1'-bi-2-naphthol (BINOL), bis(oxazolin)-ligands (BOX), tert-butoxycarbonyl-4-diphenylphosphino-2-(diphenylphosphinomethyl)pyrrolidine, 1,4,7,10-tetraazacyclododecane-1,4,7,10-tetraacetic acid (DOTA), N-heterocyclic carbenes, aminopolycarboxylic acids, 1,2-bis(o-aminophenoxy)ethane-N,N,N',N'-tetraacetic acid (BAPTA), crown ethers, diethylenetriaminepentaacetic acid (DTPA), ethylenediaminetetraacetic acid (EDTA), ethylenebis(oxyethylenenitrilo)tetraacetate (egta4-), iminodiacetic acid, nitrilotriacetic acid (NTA), tris (2-aminoethyl)amine, citrate, cyclooctene, cyclooctatetraene (COT), acetate, oxalate, picolylamine, tartrate, ethylenediaminotriacetate (TED), 2,2'-bipyridine-4-butanoic acid.

In embodiments of the first aspect of the present invention, the compound comprises formula 1-XIII: $(Z1\text{-}L3\text{-}Z2\text{-}L1\text{-}Z3\text{-}L2\text{-}Zo\text{-}Q)^N$. Each of Z1, L3, Z2, L1, Z3, L2, Zo, Q and N has the same meaning as mentioned above.

In embodiments of the first aspect of the present invention, the compound is

Label 12

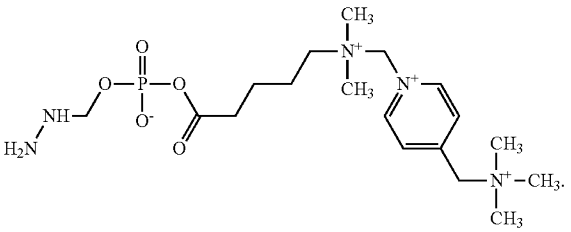

In embodiments of the first aspect of the present invention, M is 1, K is 1 and N is 2.

In embodiments of the first aspect of the present invention, each of M, N, K are integer and more than 0. It means that the moieties in brackets of formulae 1-I to 1-XIII can be repeated M-times or K-times. N is the net charge of the resulting molecule.

In embodiments of the first aspect of the present invention, L1 and L2 can be fragmented in the ion source with in-source fragmentation or in the collision cell, i.e. at different potentials (voltage).

In embodiments of the first aspect of the present invention, the compound comprises a counter ion for forming a salt, wherein the counter ion is preferably selected from the following group: $Cl^-$, $Br^-$, $F^-$, formiate, $PF_6^-$, sulfonate, phosphate, acetate.

In embodiments of the first aspect of the present invention, wherein the compound is free of trifluoroacetate (TFA). TFA as strong coordinating anion is capable to compensate a net charge per TFA molecule and therefore inhibits the double charged moiety by forming a singly charged species as TFA adduct.

In embodiments of the first aspect of the present invention, the compound is selected from the following group:

Label 13

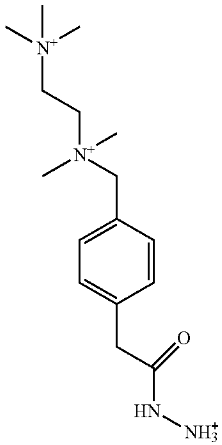

-continued

Label 14

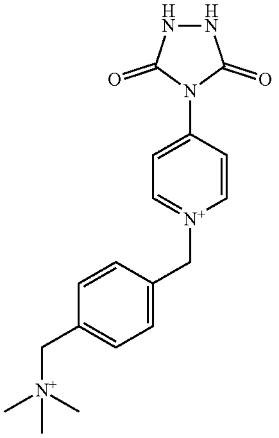

Label 15

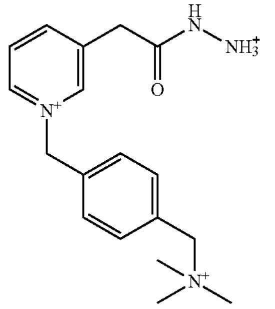

Label 16

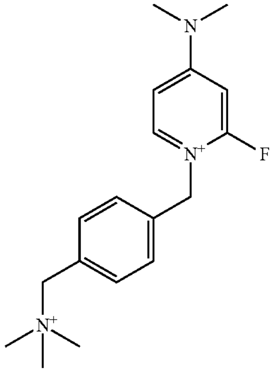

Label 17

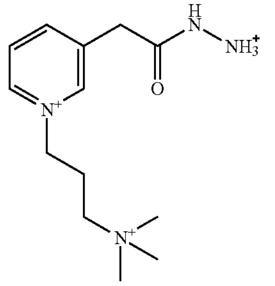

In embodiments of the first aspect of the present invention, the compound is double charged, in particular double permanently positive charged.

In embodiments of the first aspect of the present invention, the compound is selected from the following group:

Label 18

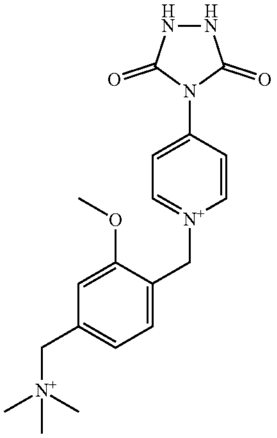

Label 19

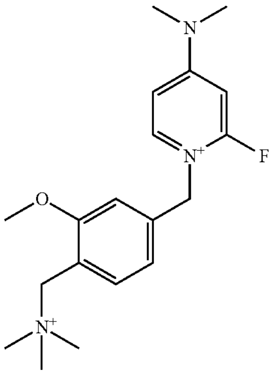

Label 20

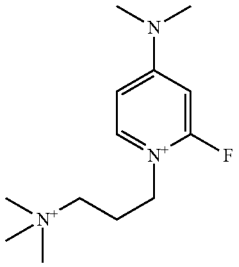

In a second aspect, the present invention relates to a composition comprising the compound as disclosed in detail above with regard to first aspect of the present invention. All embodiments mentioned for the first aspect of the invention apply for the second aspect of the invention and vice versa.

In a third aspect, the present invention relates to a kit comprising the compound as disclosed in detail herein above with regard to first aspect of the present invention or the composition of the second aspect of the present invention as disclosed in detail herein above. All embodiments mentioned for the first aspect of the invention and/or second aspect of the invention apply for the third aspect of the invention and vice versa.

In a fourth aspect, the present invention relates to a complex for quantitative detection of an analyte using mass spectrometric determination, wherein the complex is formed by the analyte and a compound, which are covalently linked to each other, wherein the complex comprises a permanent charge, in particular a permanent net charge, wherein said complex has a mass m3 and a net charge z3, wherein the complex is capable of forming at least one daughter ion having a mass m4<m3 and a net charge z4<z3 after fragmentation by mass spectrometric determination, wherein m3/z3<m4/z4.

In particular, the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof. All embodiments mentioned for the first aspect of the invention and/or second aspect of the invention and/or third aspect of the invention apply for the fourth aspect of the invention and vice versa.

In embodiments of the fourth aspect of the present invention, the complex resulting from the formation of a covalent bond between the compound with a functional group present in the analyte molecule. Depending on the reactive unit Q of the compound, and the functional group of the analyte molecule, the skilled person is well able to determine the covalent bond formed between the two.

In embodiments of the fourth aspect of the present invention, m3≥100, for example, m3 is 100, 105, 110, 115, 120, 125, 130, 135, 140, 145 or 150.

In embodiments of the fourth aspect of the present invention, each of z3 and z4 or both are permanently net charges.

In embodiments of the fourth aspect of the present invention, each of z3 and z4 or both are permanently positive net charges.

In embodiments of the fourth aspect of the present invention, each of z3 and z4 or both are permanently negative net charges.

In embodiments of the fourth aspect of the present invention, the daughter ion comprises the analyte or fragments thereof.

In embodiments of the fourth aspect of the present invention, the daughter ion comprises the analyte and a fragment of the compound, wherein the fragment of the compound is linked to the analyte via a covalent bonding, in particular wherein the fragment of the compound carries one permanently charge, in particular one permanently positive net charge or one permanently negative net charge.

In embodiments of the fourth aspect of the present invention, the complex is capable of forming further daughter ions, each comprises fragments of the compound and each having a mx/zx value with x>4, wherein each of the mx/zx value of the further daughter ions are smaller than the m3/z3 value. The further daughter ions can further comprise the analyte or fragments thereof.

In embodiments of the fourth aspect of the present invention, z3=2, wherein after fragmentation the complex is capable of forming the daughter ion with z4=1 and a further daughter ion, wherein the further daughter ion has a net charge z5, wherein z5=1, wherein the daughter ion or the further daughter ion comprises the analyte or fragments thereof. The double charged complex is fragmented between the two charges of the complex into at least two daughter ions, the daughter ion and the further daughter ion. The daughter ion as well as the further daughter ion are each one-time charged, e.g. each one-time positive charged or each one-time negative charged.

In embodiments of the fourth aspect of the present invention, the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof. All embodiments of the analyte mentioned for the first aspect of the invention apply for the fourth aspect of the invention and vice versa.

Further, it is also contemplated within the scope of the present invention that a functional group present on an analyte molecule can be first converted into another group that is more readily available for reaction with reactive unit Q of the compound.

In embodiments of the fourth aspect of the present invention, the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof.

In embodiments of the fourth aspect of the present invention, the analyte molecule comprises a functional group selected from the group consisting of carbonyl group, diene group, hydroxyl group, amine group, imine group, thiol group, diol group, phenolic group, epoxide group, disulfide group, and azide group, each of which is capable of forming a covalent bond with reactive unit Q of the compound.

In embodiments of the fourth aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the fourth aspect of the present invention, the complex comprises two positive permanently charges, which are spaced from one another by the linker L1. In particular, the each of the two positive permanently charges are positive permanently net charges.

In embodiments of the fourth aspect of the present invention, the complex comprises at least three units Z1, Z2, Q' and optional a further unit L1, wherein the units are covalently linked to each other, wherein:

Q' is a reactive unit, which forms a covalent bond with the analyte,

Z1 is a charged unit comprising at least one permanently charged moiety, in particular a permanently positive charged moiety or a permanently negative charged moiety, Z2 is a charged unit comprising at least one permanently charged moiety, in particular a permanently positive charged moiety or a permanently negative charged moiety, and L1 is a substituted or non-substituted linker, in particular a cleavable group via fragmentation, e.g. Mc Lafferty fragmentation moiety, Retro Diels Alder fragmentation moiety, benzylic or aliphatic, and wherein the net charge of the complex is greater than 1. Z1, Z2 and L1 can have the same meaning as mentioned for Z1, Z2 and L1 with respect to embodiments of the first aspect of the present invention.

In embodiments of the fourth aspect of the present invention, Q' results from the formation of a covalent bond between the reactive unit Q of compound of the first aspect of the present invention with a functional group present in the analyte molecule. Depending on the reactive unit Q of compound of the first aspect of the present invention, and the functional group of the analyte molecule, the skilled person is well able to determine the covalent bond formed between the two.

In embodiments of the fourth aspect of the present invention, net charge of the complex is 2, 3, 4 or 5.

In embodiments of the fourth aspect of the present invention, the complex is selected from the following formulae 2-I to 2-XI:

(2-I)

$$(Z1—L1—Z2—Q')^N$$

(2-II)

$$(Q'—Z2—L1—Z2)^N$$

(2-III)

$$(Z1—Z2—Q')^N$$

(2-IV)

$$(Z1—(L1—Z2)_M—(L2—Zo)_K—Q')^N$$

(2-V)

$$(Z1—(L3—Z2)_M—(L2—Zo)_K—Q')^N$$

(2-VI)

$$((Z1)_M—L1—Z2—(L2/L3)_K—Zo)^N—Q'$$

(2-VII)

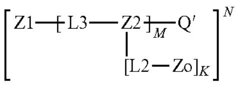

(2-VIII)

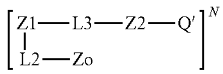

(2-IX)

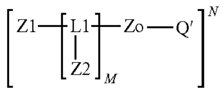

(2-X)

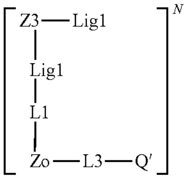

(2-XI)

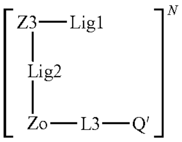

wherein the analyte is covalently bonded to Q',

Z1 is a charged unit comprising at least one permanently charged moiety, in particular a permanently positive charged moiety or a permanently negative charged moiety, L1 is a substituted or non-substituted linker, in particular a cleavable group via fragmentation, e.g. Mc Lafferty fragmentation moiety, Retro Diels Alder fragmentation moiety, benzylic or aliphatic, Z2 is a charged unit comprising at least one permanently charged moiety, in particular a permanently positive charged moiety or a permanently negative charged moiety, Zo is a charged unit, in particular comprising either a positive or a negative or a neutral charged unit, Z3 is a multiple charged unit, in particular a multiple charged metal unit, L3 is a substituted or non-substituted linker, in particular a non-cleavable group via fragmentation, e.g. benzylic or diazo, Lig1 is a multiple charged metal complex binding ligand, in particular depended with a binding constant log $K_B>5$, L2 is a substituted or non-substituted linker, in particular L2 is L1 or L2 is a cleavable group via fragmentation, Lig2 is a multiple charged metal complex binding ligand, in particular depended with a binding constant: $1<\log K_B\leq 5$, $M>0$, $K>0$ and $N\geq 1$.

In embodiments of the fourth aspect of the present invention, the binding compound is covalently linked via a carbonyl group, hydroxyl group or diene group of the analyte to form the said complex. Binding compound means the compound of the compound-analyte complex.

In a fifth aspect, the present invention relates to the use of the compound for mass spectrometric determination of the analyte. Preferably the mass spectrometric determination comprises a tandem mass spectrometric determination, in particular a triple quadrupole mass spectrometric determination. All embodiments mentioned for the first aspect of the invention and/or second aspect of the invention and/or third aspect of the invention and/or fourth aspect of the invention apply for the fifth aspect of the invention and vice versa.

In embodiments of the fifth aspect of the present invention, the signal to noise ratio of a mass spectrometric spectrum of the compound of first aspect of the present invention or of a complex of the fourth aspect of the present invention is lower compared to a the mass spectrometric spectrum of an exemplary complex or exemplary compound, which has a one-time permanently net charge equal to or smaller than 1 as a maximum.

In a sixth aspect, the present invention relates to a method for mass spectrometric determination of an analyte comprising the steps of:

(a) reacting the analyte with the compound as disclosed herein with regard to the first aspect of the present invention, whereby a complex as disclosed herein with regard to the fourth aspect of the present invention is formed, (b) subjected the complex from step (a) to a mass spectrometric analysis.

In embodiments of the sixth aspect of the present invention, mass spectrometric analysis step (b) comprises:

(i) subjecting an ion of the complex to a first stage of mass spectrometric analysis, whereby the ion of the complex is characterized according to its mass/charge (m/z) ratio, (ii) causing fragmentation of the complex ion, whereby a first entity, particularly a low-molecular weight entity, is released and a daughter ion of the complex is generated, wherein the daughter ion of the complex differs in its m/z ratio from the complex ion, and (iii) subjecting the daughter ion of the complex to a second stage of mass spectrometric analysis, whereby the daughter ion of the complex is characterized according to its m/z ratio, and/or wherein (ii) may further comprises alternative fragmentation of the complex ion, whereby a second entity different from the first entity is released and a second daughter ion of the complex is generated, and wherein (iii) may further comprises subjecting the first and second daughter ions of the complex to a second stage of mass spectrometric analysis, whereby the first and second daughter ions of the complex are characterized according to their m/z ratios, wherein the m/z ratio of the first and/or the second daughter ion is greater than the m/z ratio of ion of the complex.

In embodiments of the sixth aspect of the present invention, a further step (a') before step (a) comprises:

(a') subjecting the ion of the complex or an ion of the compound an ion exchange of the counter ion, wherein in particular a strongly coordinating anion, e.g. trifluoroacetate, as the counter ion is exchanged by chloride, bromide or a weekly coordinating counter ion.

A weekly counter ion is an ion not binding the analyte in the gas phase. It gets dissociated by introducing the mass spectrometer via the ion source.

A strongly coordinating anion means that the binding constant of the complex or compound comprising a strongly coordinating anion as the counter ion is greater than the binding constant of a corresponding complex or compound comprising chloride as a counter ion in the gas phase.

In embodiments of the sixth aspect of the present invention, the first entity and/or second entity is selected from the group consisting of trimethylamine, pyridine, phosphine, trimethylamine, tripropylamine, tributylamine dimethylethylamine, methyldiethylamine and trialkylamine.

Step (a) may occur at different stages within the sample preparation workflow prior to mass spectrometric determination. The samples comprising an analyte molecule may be pre-treated and/or enriched by various methods. The pre-treatment method is dependent upon the type of sample, such as blood (fresh or dried), plasma, serum, urine, or saliva, whereas the enrichment method is dependent on the analyte of interest. It is well known to the skilled person which pre-treatment sample is suitable for which sample type. It is also well-known to the skilled person which enrichment method is suitable for which analyte of interest.

In embodiments of the sixth aspect of the present invention, step (a) of the present method for the mass spectrometric determination of an analyte molecule takes place i) subsequent to a pre-treatment step of the sample, ii) subsequent to a first enrichment of the sample, or iii) subsequent to a second enrichment of the sample.

In embodiments of the sixth aspect of the present invention, wherein the sample is a whole blood sample, it is assigned to one of two pre-defined sample pre-treatment (PT) workflows, both comprising the addition of an internal standard (ISTD) and a hemolysis reagent (HR) followed by a pre-defined incubation period (Inc), where the difference between the two workflows is the order in which the internal standard (ISTD) and a hemolysis reagent (HR) are added. In embodiments water is added as a hemolysis reagents, in particular in an amount of 0.5:1 to 20:1 ml water/ml sample, in particular in an amount of 1:1 to 10:1 mL water/mL sample, in particular in an amount of 2:1 to 5:1 ml water/ml sample.

In embodiments of the sixth aspect of the present invention, the sample is a urine sample, it is assigned to one of other two pre-defined sample PT workflows, both comprising the addition of an internal standard and an enzymatic reagent followed by a pre-defined incubation period, where the difference between the two workflows is the order in which the internal standard and a enzymatic reagent are added. An enzymatic reagent is typically a reagent used for glucuronide cleavage or protein cleavage or any pre-processing of analyte or matrix. In an additional step a derivatization reagent such as compounds of the present invention as disclosed herein above or below, is added followed by an incubation period.

In embodiments of the sixth aspect of the present invention, the enzymatic reagent in selected from the group consisting of glucuronidase, (partial) exo- or endo-deglycosylation enzymes, or exo- or endo proteases. In embodiments, glucoronidase is added in amount of 0.5-10 mg/ml, in particular in an amount of 1 to 8 mg/ml, in particular in an amount of 2 to 5 mg/ml.

In embodiments of the sixth aspect of the present invention, wherein the sample is plasma or serum it is assigned to another pre-defined PT workflow including only the addition of an internal standard (ISTD) followed by a pre-defined incubation time.

It is well-known to the skilled person which incubation time and temperature to choose for a sample treatment, chemical reaction or method step considered and as named herein above or below. In particular, the skilled person knows that incubation time and temperature depend upon each other, in that e.g. a high temperature typically leads to a shorter incubation period and vise versa. In embodiments of the sixth aspect of the invention, the incubation temperature is in a range of 4 to 45° C., in particular in a range of 10-40° C., in particular at 20-37° C. In embodiments, the incubation time is in the range of 30 sec to 120 min, in particular 30 sec to 1 min, 30 sec to 5 min, 30 sec to 10 min, 1 min to 10 min, or 1 min to 20 min, 10 min to 30 min, 30 min to 60 min, or 60 min to 120 min. In particular embodiments, the incubation time is a multiple of 36 sec.

Accordingly, the embodiments of the present method, step a) takes place subsequent to either of the above disclosed pre-treatment process of the sample.

In embodiment of the sixth aspect of the present invention, the reaction of the compound and the analyte molecule in step a) takes place before any enrichment process, the compound is added to the pre-treated sample of interest. Accordingly, the complex of the analyte molecule and the compound is formed after the pre-treatment and prior to the first enrichment process. The complex is thus, subjected to the first enrichment process and to the second enrichment process before being subjected to the mass spectrometric analysis of step b).

The pre-treated sample may be further subjected to an analyte enrichment workflow. The analyte enrichment workflow may include one or more enrichment methods. Enrichment methods are well-known in the art and include but are not limited to chemical enrichment methods including but not limited to chemical precipitation, and enrichment methods using solid phases including but not limited to solid phase extraction methods, bead workflows, and chromatographic methods (e.g. gas or liquid chromatography).

In embodiments of the sixth aspect of the present invention, a first enrichment workflow comprises the addition of a solid phase, in particular of solid beads, carrying analyte-selective groups to the pre-treated sample. In embodiments of the sixth aspect of the present invention, a first enrichment workflow comprises the addition of magnetic or paramagnetic beads carrying analyte-selective groups to the pre-treated sample. In embodiments of the sixth aspect of the present invention, the addition of the magnetic beads comprises agitation or mixing. A pre-defined incubation period for capturing the analyte(s) of interest on the bead follows. In embodiments of the sixth aspect of the present invention, the workflow comprises a washing step (W1) after incubation with the magnetic beads. Depending on the analyte(s) one or more additional washing steps (W2) are performed. One washing step (W1, W2) comprises a series of steps including magnetic bead separation by a magnetic bead handling unit comprising magnets or electromagnets, aspiration of liquid, addition of a washing buffer, resuspension of the magnetic beads, another magnetic bead separation step and another aspiration of the liquid. Moreover washing steps may differ in terms of type of solvent (water/organic/salt/pH), apart from volume and number or combination of washing cycles. It is well-known to the skilled person how to choose the respective parameters. The last washing step (W1, W2) is followed by the addition of an elution reagent followed by resuspension of the magnetic beads and a pre-defined incubation period for releasing the analyte(s) of interest from the magnetic beads. The bound-free magnetic beads are then separated and the supernatant containing derivatized analyte(s) of interest is captured.

In embodiments of the sixth aspect of the present invention, a first enrichment workflow comprises the addition of magnetic beads carrying matrix-selective groups to the pre-treated sample. In embodiments of the sixth aspect of the present invention, the addition of the magnetic beads comprises agitation or mixing. A pre-defined incubation period for capturing the matrix on the bead follows. Here, the analyte of interest does not bind to the magnetic beads but remains in the supernatant. Thereafter, the magnetic beads are separated and the supernatant containing the enriched analyte(s) of interest is collected.

In embodiments of the sixth aspect of the present invention, the supernatant is subjected to a second enrichment workflow. Here, the supernatant is transferred to the LC station or is transferred to the LC station after a dilution step by addition of a dilution liquid. Different elution procedures/reagents may also be used, by changing e.g. the type of solvents (water/organic/salt/pH) and volume. The various parameters are well-known to the skilled person and easily chosen.

In embodiments of the sixth aspect of the present invention, wherein step a) of the present method did not take place directly after the pre-treatment method, step a) may take place after the first enrichment workflow using magnetic beads as described herein above.

In embodiments of the sixth aspect of the present invention, wherein analyte specific magnetic beads are used, the compounds as disclosed herein above or below, is added to the sample of interest after the washing steps (W1, W2) are concluded either prior to, together with or subsequent with the elution reagent, which is followed by an incubation period (defined time and temperature).

In embodiments of the sixth aspect of the present invention, the bound-free magnetic beads are then separated and the supernatant containing the complex of step a) is collected. In embodiments of the sixth aspect of the present invention, the supernatant containing the complex of step a) is transferred to a second enrichment workflow, in particular either directly transferred to an LC station or after a dilution step by addition of a dilution liquid.

In embodiments of the sixth aspect of the present invention, wherein matrix-specific magnetic beads are used, the compounds as disclosed herein above or below, is added to the sample of interest before or after the magnetic beads are separated. In embodiments of the sixth aspect of the present invention, the supernatant containing the complex of step a) is transferred to a second enrichment workflow, in particular either directly to an LC station or after a dilution step by addition of a dilution liquid.

Accordingly, in embodiments of the sixth aspect of the present invention, wherein the reaction of the compound and the analyte molecule in step a) takes place subsequent to a first enrichment process, the compound is added to the sample of interest after the first enrichment process, in particular a first enrichment process using magnetic beads, is concluded. Accordingly, the sample is first pre-treated as described herein above, is then subjected to a first enrichment process, in particular using magnetic beads, carrying analyte selective groups as described herein above, and prior to, simultaneously with or subsequently to the elution from the beads, the compound is added. Accordingly, the complex of the analyte molecule and the compound is formed after the first enrichment process and prior to the second enrichment process. The complex is thus, subjected to the second enrichment process before being subjected to the mass spectrometric analysis of step b).

In another embodiment of the sixth aspect of the present invention, step (a) of the present method takes place after a second analyte enrichment workflow. In the second enrichment workflow, chromatographic separation is used to further enrich the analyte of interest in the sample. In embodiments of the sixth aspect of the present invention, the chromatographic separation is gas or liquid chromatography. Both methods are well known to the skilled person. In embodiments of the sixth aspect of the present invention, the liquid chromatography is selected from the group consisting of HPLC, rapid LC, micro-LC, flow injection, and trap and elute.

In embodiments of the sixth aspect of the present invention, step a) of the present method takes place concurrent with or subsequent to the chromatographic separation. In embodiment of the sixth aspect of the present invention, the compound is added to the column together with the elution buffer. In alternative embodiments, the compound is added post column.

In embodiments of the sixth aspect of the present invention, the first enrichment process includes the use of analyte selective magnetic beads. In embodiments of the sixth aspect of the present invention, the second enrichment process includes the use of chromatographic separation, in particular using liquid chromatography.

Accordingly, in embodiments of the sixth aspect of the present invention, wherein the reaction of the compound and the analyte molecule in step a) takes place subsequent to a second enrichment process, the compound is added to the sample of interest after the second enrichment process using chromatography, in particular liquid chromatography, is concluded. Accordingly, in this case, the sample is first pre-treated as described herein above, is then subjected to a first enrichment process, in particular using magnetic bead, as described herein above, followed by chromatographic separation, in particular using liquid chromatography, and subsequent to chromatographic separation the compound is added. Accordingly, the complex of the binding analyte molecule and the binding compound is formed after the second enrichment process. The complex is thus, not subjected to a enrichment process before being subjected to the mass spectrometric analysis of step b).

In embodiments of the present invention, a clinical diagnostic system comprises the compound of the first aspect of the invention and/or the composition of the second aspect of the present invention and/or the kit of the third aspect of the present invention and/or the complex of the fourth aspect of the present invention. Additionally or optionally, the compound of the first aspect of the present invention is used for mass spectrometric determination of an analyte, wherein the clinical diagnostic system comprises the mass spectrometric determination. Additionally or optionally, the method for mass spectrometric determination of an analyte of the sixth aspect of the present invention is performed by the clinical diagnostic system.

A "clinical diagnostics system" is a laboratory automated apparatus dedicated to the analysis of samples for in vitro diagnostics. The clinical diagnostics system may have different configurations according to the need and/or according to the desired laboratory workflow. Additional configurations may be obtained by coupling a plurality of apparatuses and/or modules together. A "module" is a work cell, typically smaller in size than the entire clinical diagnostics system, which has a dedicated function. This function can be analytical but can be also pre-analytical or post analytical or it can be an auxiliary function to any of the pre-analytical function, analytical function or post-analytical function. In particular, a module can be configured to cooperate with one or more other modules for carrying out dedicated tasks of a sample processing workflow, e.g. by performing one or more pre-analytical and/or analytical and/or post-analytical steps. In particular, the clinical diagnostics system can comprise one or more analytical apparatuses, designed to execute respective workflows that are optimized for certain types of analysis, e.g. clinical chemistry, immunochemistry, coagulation, hematology, liquid chromatography separation, mass spectrometry, etc. Thus the clinical diagnostic system may comprise one analytical apparatus or a combination of any of such analytical apparatuses with respective workflows, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The clinical diagnostics system can comprise functional units such as liquid handling units for pipetting and/or pumping and/or mixing of samples and/or reagents and/or system fluids, and also functional units for sorting, storing, transporting, identifying, separating, detecting. The clinical diagnostic system can comprise a sample preparation station for the automated preparation of samples comprising analytes of interest, a liquid chromatography (LC) separation station comprising a plurality of LC channels and/or a sample preparation/LC interface for inputting prepared samples into any one of the LC channels. The clinical diagnostic system can further comprise a controller programmed to assign samples to pre-defined sample preparation workflows each comprising a pre-defined sequence of sample preparation steps and requiring a pre-defined time for completion depending on the analytes of interest. The clinical diagnostic system can further comprise a mass spectrometer (MS) and an LC/MS interface for connecting the LC separation station to the mass spectrometer. The term "automatically" or "automated" as used herein is a broad term and is to be given its ordinary and customary meaning to a person of ordinary skill in the art and is not to be limited to a special or customized meaning. The term specifically may refer, without limitation, to a process which is performed completely by means of at least one computer and/or computer network and/or machine, in particular without manual action and/or interaction with a user.

A "sample preparation station" can be a pre-analytical module coupled to one or more analytical apparatuses or a unit in an analytical apparatus designed to execute a series of sample processing steps aimed at removing or at least reducing interfering matrix components in a sample and/or enriching analytes of interest in a sample. Such processing steps may include any one or more of the following processing operations carried out on a sample or a plurality of samples, sequentially, in parallel or in a staggered manner: pipetting (aspirating and/or dispensing) fluids, pumping fluids, mixing with reagents, incubating at a certain temperature, heating or cooling, centrifuging, separating, filtering, sieving, drying, washing, resuspending, aliquoting, transferring, storing, etc.).

A "liquid chromatography (LC) separation station" is an analytical apparatus or module or a unit in an analytical apparatus designed to subject the prepared samples to chromatographic separation in order for example to separate analytes of interest from matrix components, e.g. remaining matrix components after sample preparation that may still interfere with a subsequent detection, e.g. a mass spectrometry detection, and/or in order to separate analytes of interest from each other in order to enable their individual detection. According to an embodiment, the LC separation station is an intermediate analytical apparatus or module or a unit in an analytical apparatus designed to prepare a sample for mass spectrometry and/or to transfer the prepared sample to a mass spectrometer. In particular, the LC separation station is a multi-channel LC station comprising a plurality of LC channels.

The clinical diagnostic system, e.g. the sample preparation station, may also comprise a buffer unit for receiving a plurality of samples before a new sample preparation start sequence is initiated, where the samples may be individually randomly accessible and the individual preparation of which may be initiated according to the sample preparation start sequence.

The clinical diagnostic system makes use of LC coupled to mass spectrometry more convenient and more reliable and therefore suitable for clinical diagnostics. In particular, high-throughput, e.g. up to 100 samples/hour or more with random access sample preparation and LC separation can be obtained while enabling online coupling to mass spectrometry. Moreover the process can be fully automated increasing the walk-away time and decreasing the level of skills required.

In further embodiments, the present invention relates to the following aspects:

1. A compound for quantitative detection of an analyte using mass spectrometric determination, wherein said compound comprises a permanent charge, in particular a permanent net charge, wherein said compound is capable of covalently binding to the analyte, wherein said compound has a mass m1 and a net charge z1, wherein the compound is capable of forming at least one daughter ion having a mass m2<m1 and a net charge z2<z1 after fragmentation by mass spectrometric determination, wherein m1/z1<m2/z2.

2. The compound of aspect 1, wherein m1/z1 is at least 60 or more, for example 66 for $C_7H_2ON_2^{2+}$, and/or m2/z2 is at least 70 or more, for example 74 for $C_4H_{12}N^+$.

3. The compound of aspect 1 or 2, which is free of a sulfoxide unit (SO).

4. The compound of any of the proceeding aspects, wherein z1 is an integer and is 2 or more than 2.

5. The compound of any of the proceeding aspects, wherein z1 is 2, 3, 4 or 5, preferably z1 is 2.

6. The compound of any of the proceeding aspects, wherein z2=z1−1, preferably z2 is 1.

7. The compound of any of the proceeding aspects, wherein each of z1 and z2 or both are permanently charges, in particular permanently net charges.

8. The compound of any of the proceeding aspects, wherein each of z1 and z2 or both are permanently positive charges, in particular permanently positive net charges.

9. The compound of any of the proceeding aspects, wherein each of z1 and z2 or both are permanently negative charges, in particular permanently negative net charges.

10. The compound of any of the proceeding aspects, wherein the net charge z1 is the sum of x-times positive permanently charges and y-times negative permanently charges of the compound.

11. The compound of any of the proceeding aspects, wherein the net charge z2 is the sum of x-times positive permanently charges and y-times negative permanently charges of the at least one daughter ion.

12. The compound of any of the proceeding aspects, wherein the compound is capable of forming further daughter ions, each of the further daughter ions comprises a fragment or more fragments of the compound and each having a mx/zx value with x >4, wherein each of the mx/zx value of the further daughter ions is smaller than the m1/z1 value.

13. The compound of any of the proceeding aspects comprising at least three units Z1, Z2, Q and optional a further unit L1, wherein the units are covalently linked to each other, wherein:

Q is a reactive unit capable of forming a covalent bond with the analyte,

Z1 is a charged unit comprising at least one permanently charged moiety, in particular a permanently positive charged moiety or a permanently negative charged moiety, Z2 is a charged unit comprising at least one permanently charged moiety, in particular a permanently positive charged moiety or a permanently negative charged moiety, and L1 is a substituted or non-substituted linker, in particular a cleavable group via fragmentation, e.g. Mc Lafferty fragmentation moiety, Retro Diels Alder fragmentation moiety or aliphatic, wherein the net charge of the compound is greater than 1.

14. The compound of any of the proceeding aspects, wherein Z1 and Z2 are separated from each other by at least one atom.

15. The compound of any of the proceeding aspects, wherein Q is covalently linked to Z1 or Q is covalently linked to Z2.

16. The compound of any of the proceeding aspects, wherein L1 covalently links Z1 and Z2.

17. The compound of any of the proceeding aspects, wherein the compound is fragmented between Z1 and Z2.

18. The compound of any of the proceeding aspects, comprising the formula 1-I: $(Z1\text{-}L1\text{-}Z2\text{-}Q)^N$ with N≥1. N≥1 can mean N≥+1 and/or N≥−1. N≥+1 can mean e.g. +1, +2, +3, +4, +5, +6, etc. N≥−1 can mean e.g. −1, −2, −3, −4, −5, −6, etc.

19. The compound of any of the proceeding aspects, comprising the formula 1-II: (Q-Z1-L1-Z2) N with N >1.

20. The compound of any of the proceeding aspects, comprising the formula 1-III: $(Z1\text{-}Z2\text{-}Q)^N$ with N >1.

21. The compound of any of the proceeding aspects, wherein the reactive unit Q is selected from the group consisting of carbonyl reactive unit, diene reactive unit, hydroxyl reactive unit, amino reactive unit, an imine reactive unit, a thiol reactive unit, a diol reactive unit, a phenol reactive unit, epoxide reactive unit, a disulfide reactive unit, and an azide reactive unit.

22. The compound of any of the proceeding aspects, wherein the reactive unit Q is a carbonyl-reactive group, in particular wherein Q is selected from the group consisting of (i) a hydrazine unit, e.g. a $H_2N$—NH—, or $H_2N$—NR1-unit, wherein R1 is aryl or C1-4 alkyl, particularly C1 or C2 alkyl, optionally substituted, (ii) a hydrazide unit, in particular a carbo-hydrazide or a sulfohydrazide, in particular a $H_2N$—NH—C(O)—, or $H_2N$—NR2-C(O)— unit, wherein R2 is aryl or C1-4 alkyl, particularly C1 or C2 alkyl, optionally substituted, (iii) a hydroxylamino unit, e.g. a $H_2N$—O— unit, and (iv) a dithiol unit, particularly a 1,2-dithiol or 1,3-dithiol unit.

23. The compound of any of the proceeding aspects, wherein the reactive unit Q is a thiol-reactive group or is an amino-reactive group such as an active ester group, e.g. N-hydroxysuccinimide (NHS) ester or sulpho-NHS ester, a hydroxybenzotriazole (HOBt) ester or 1-hydroxy-7-azabenzotriazole (HOAt) ester group.

24. The compound of any of the proceeding aspects, wherein the reactive unit Q is selected from 4-substituted 1,2,4-triazolin-3,5-dione (TAD), 4-Phenyl-1,2,4-triazolin-3,5-dion (PTAD) or fluoro-substituted pyridinium.

25. The compound of any of the proceeding aspects, wherein the linker L1 comprises 1 to 10 C-atoms, optionally comprising 1 or more heteroatoms.

26. The compound of any of the proceeding aspects, wherein the linker L1 is selected from the group consisting of McLafferty fragmentation unit, Retro Diels alder unit, neutral loss cleaving unit, bond dissociation unit, alpha-cleavage and charge site rearrangements.

27. The compound of any of the proceeding aspects, wherein Z1 and Z2 comprise independently of each other a chelate complex, phosphonium, ammonium, carbenium, pyridinium, sulphonium, charged heterocycles of 3-10 membered rings containing either N, S, H, and C-Atoms or derivatives thereof.

28. The compound of any of the proceeding aspects, comprising formula 1-IV: $(Z1\text{-}(L1\text{-}Z2)_M\text{-}(L2\text{-}Zo)_K\text{-}Q)^N$, wherein:

Zo is a charged unit, in particular comprising either a positive charged unit or a negative charged unit or a neutral charged unit, L2 is a substituted linker or non-substituted linker, in particular L2 is L1 or in particular L2 is a cleavable group via fragmentation, M>0, K>0 and N≥1.

29. The compound of any of the proceeding aspects, comprising formula 1-V: $(Z1\text{-}(L3\text{-}Z2)_M\text{-}(L2\text{-}Zo)_K\text{-}Q)^N$, wherein:

Zo is a charged unit, in particular comprising either a positive charged unit or a negative charged unit or a neutral charged unit, L2 is a substituted linker or non-substituted linker, in particular L2 is L1 or in particular L2 is a cleavable group via fragmentation L3 is a substituted linker or non-substituted linker, in particular a non-cleavable group via fragmentation, e.g. benzylic or diazo, M>0, K>0 and N≥1.

30. The compound of any of the proceeding aspects, comprising formula 1-VI: $((Z1)_M\text{-}L1\text{-}Z2\text{-}(L2/L3)_K\text{-}Zo)^N\text{-}Q$, wherein:

Zo is a charged unit, in particular comprising either a positive charged unit or a negative charged unit or a neutral charged unit, L2 is a substituted linker or non-substituted linker, in particular L2 is L1 or in particular L2 is a cleavable group via fragmentation,

- L3 is a substituted linker or non-substituted linker, in particular a non-cleavable group via fragmentation, e.g. benzylic or diazo, $M>0$, $K\geq 0$ and $N\geq 1$.

31. The compound of any of the proceeding aspects, comprising formula 1-VII: $(Z1\text{-}L1\text{-}Z2\text{-}Q)^N$, wherein: $N\geq 1$.

32. The compound of any of the proceeding aspects, comprising formula 1-VIII:

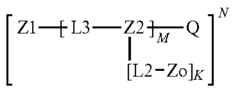

wherein:

- Zo is a charged unit comprising, in particular either a positive charged unit or a negative charged unit or a neutral charged unit,
- L2 is a substituted linker or non-substituted linker, in particular L2 is L1 or in particular L2 is a cleavable group via fragmentation,
- L3 is a substituted linker or non-substituted linker, in particular a non-cleavable group via fragmentation, e.g. benzylic or diazo, $N\geq 1$, $M>0$ and $K>0$.

33. The compound of any of the proceeding aspects, comprising formula 1-IX:

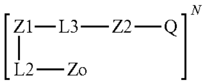

wherein:

- Zo is a charged unit, in particular comprising either a positive charged unit or a negative charged unit or a neutral charged unit,
- L2 is a substituted linker or non-substituted linker, in particular L2 is L1 or in particular L2 is a cleavable group via fragmentation,
- L3 is a substituted linker or non-substituted linker, in particular a non-cleavable group via fragmentation, e.g. benzylic or diazo, and $N\geq 1$.

34. The compound of any of the proceeding aspects, comprising formula 1-X:

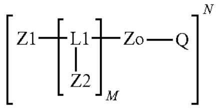

wherein:

- Zo is a charged unit comprising, in particular either a positive charged unit or a negative charged unit or a neutral charged unit, $N\geq 1$ and $M>0$.

35. The compound of any of the proceeding aspects, comprising formula 1-XI:

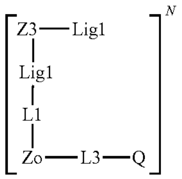

wherein:

- Zo is a charged unit comprising, in particular either a positive charged unit or a negative charged unit or a neutral charged unit,
- Z3 is a multiple charged unit, in particular a multiple charged metal unit,
- L3 is a substituted linker or non-substituted linker, in particular a non-cleavable group via fragmentation, e.g. benzylic, diazo or aliphatic group consisting of at least one or two carbon atoms (C1-C2) and aliphatic group consisting of C1-C2,
- Lig1 is a multiple charged metal complex binding ligand, in particular depended with a binding constant log Kb>5, and $N>1$.

36. The compound of any of the proceeding aspects, comprising formula 1-XII:

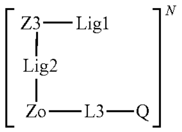

wherein:

- Zo is a charged unit comprising, in particular either a positive charged unit or a negative charged unit or a neutral charged unit,
- Z3 is a multiple charged unit, in particular a multiple charged metal unit,
- L3 is a substituted linker or non-substituted linker, in particular a non-cleavable group via fragmentation, e.g. benzylic or diazo,
- Lig1 is a multiple charged metal complex binding ligand, in particular depended with a binding constant log $K_B>5$
- Lig2 is a multiple charged metal complex binding ligand, in particular depended with a binding constant $1\leq \log K_B\leq 5$ and $N\geq 1$.

37. The compound of any of the proceeding aspects, comprising formula 1-XIII: $(Z1\text{-}L3\text{-}Z2\text{-}L1\text{-}Z3\text{-}L2\text{-}Zo\text{-}Q)^N$, wherein each of Z1, L3, Z2, L1, Z3, L2, Zo, Q and N can have the same meaning as mentioned in the other aspects.

38. The compound of any of the proceeding aspects, wherein each of M, N, K are integer and more than 0. The moieties in brackets of formulae 1-I to 1-XIII can be repeated M-times and K-times and N is the net charge of the compound.

39. The compound of any of the proceeding aspects, wherein the compound comprises a counter ion for forming a salt, wherein the counter ion is preferably selected from the following group: $Cl^-$, $Br^-$, $F^-$, formiate, $PF_6^-$, sulfonate, phosphate, acetate.

40. The compound of any of the proceeding aspects, wherein the compound is free of trifluoroacetate (TFA).

41. A composition comprising the compound of any of aspects 1 to 40.

42. A kit comprising the compound of any of aspects 1 to 40 or the composition of aspect 41.

43. A complex for quantitative detection of an analyte using mass spectrometric determination, wherein the complex is formed by the analyte and a compound, which are covalently linked to each other, wherein the complex comprises a permanent charge, in particular a permanent net charge, wherein said complex has a mass m3 and a net charge z3, wherein the complex is capable of forming at least one daughter ion having a mass m4<m3 and a net charge z4<z3 after fragmentation by mass spectrometric determination, wherein m3/z3<m4/z4.

44. The complex of aspect 43, wherein m3≥100.

45. The complex of aspects 43 to 44, wherein each of z3 and z4 or both are permanently net charges.

46. The complex of aspects 43 to 45, wherein each of z3 and z4 or both are permanently positive net charges.

47. The complex of aspects 43 to 46, wherein each of z3 and z4 or both are permanently negative net charges.

48. The complex of aspects 43 to 47, wherein the daughter ion comprises the analyte or fragments thereof.

49. The complex of aspects 43 to 48, wherein the complex is a parent ion.

50. The complex of aspects 43 to 49, wherein the daughter ion comprises the analyte and a fragment of the compound, wherein the fragment of the compound is linked to the analyte via a covalent bonding, in particular wherein the fragment of the compound carries one permanently charge, in particular one permanently positive charge or one permanently negative charge.

51. The complex of aspects 43 to 50, wherein the complex is capable of forming further daughter ions, each comprises fragments of the compound and each having a mx/zx value with x>4, wherein each of the mx/zx value of the further daughter ions are smaller than the m3/z3 value.

52. The complex of aspects 43 to 51, wherein z3=2, wherein after fragmentation the complex is capable of forming the daughter ion with z4=1 and a further daughter ion, wherein the further daughter ion has a net charge z5, wherein z5=1, wherein the daughter ion or the further daughter ion comprises the analyte or fragments thereof.

53. The complex of aspects 43 to 52, wherein the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof.

54. The complex of aspects 43 to 53, wherein the complex comprises two positive permanently charges, which are spaced from one another by the linker L1.

55. The complex of aspects 43 to 54, comprising at least three units Z1, Z2, Q' and optional a further unit L1, wherein the units are covalently linked to each other, wherein:

Q' is a reactive unit, which forms a covalent bond with the analyte,

Z1 is a charged unit comprising at least one permanently charged moiety, in particular a permanently positive charged moiety or a permanently negative charged moiety, Z2 is a charged unit comprising at least one permanently charged moiety, in particular a permanently positive charged moiety or a permanently negative charged moiety, and L1 is a substituted linker or non-substituted linker, in particular a cleavable group via fragmentation, e.g. Mc Lafferty fragmentation moiety, Retro Diels Alder fragmentation moiety or aliphatic, and wherein the net charge of the complex is greater than 1.

56. The complex of aspects 43 to 55, wherein the complex is selected from the following formulae 2-I to 2-XI:

$$(Z1—L1—Z2—Q')^N \quad (2\text{-}I)$$

$$(Q'—Z2—L1—Z2)^N \quad (2\text{-}II)$$

$$(Z1—Z2—Q')^N \quad (2\text{-}III)$$

$$(Z1—(L1—Z2)_M—(L2—Zo)_K—Q')^N \quad (2\text{-}IV)$$

$$(Z1—(L3—Z2)_M—(L2—Zo)_K—Q')^N \quad (2\text{-}V)$$

$$((Z1)_M—L1—Z2—(L2/L3)_K—Zo)^N—Q' \quad (2\text{-}VI)$$

(2-VII)

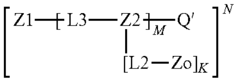

(2-VIII)

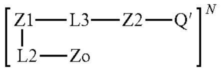

(2-IX)

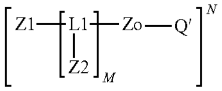

(2-X)

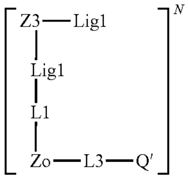

(2-XI)

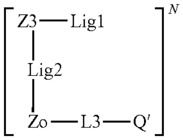

wherein the analyte is covalently bonded to Q',

Z1 is a charged unit comprising at least one permanently charged moiety, in particular a permanently positive charged moiety or a permanently negative charged moiety, L1 is a substituted or non-substituted linker, in particular a cleavable group via fragmentation, e.g. Mc Lafferty fragmentation moiety, Retro Diels Alder fragmentation moiety or aliphatic, Z2 is a charged unit comprising at least one permanently charged moiety, in particular a permanently positive charged moiety or a permanently negative charged moiety, Zo is a charged unit, in particular comprising either a positive or a negative or a neutral charged unit, Z3 is a multiple charged unit, in particular a multiple charged metal unit, L3 is a substituted or non-substituted linker, in particular a non-cleavable group via fragmentation, e.g. benzylic or diazo, Lig1 is a multiple charged metal complex binding ligand, in particular depended with a binding constant log $K_B$>5, L2 is a substituted or non-substituted linker, in particular L2 is L1 or L2 is a cleavable group via fragmentation, Lig2 is a multiple charged metal complex binding ligand, in particular depended with a binding constant: 1≤log $K_B$≤5, M >0, K >0 and N >1, preferably N >1. N >1 can mean N >+1, e.g. +2, +3, +4, +5, +6, etc. and/or can mean N>−1, e.g. −2, −3, −4, −5, −6, etc.

57. Use of the compound of any of aspects 1 to 40 for mass spectrometric determination of the analyte, preferably wherein the mass spectrometric determination comprises a tandem mass spectrometric determination, in particular a triple quadrupole mass spectrometric determination.

58. The use of aspect 57, wherein the signal to noise ratio of a mass spectrometric spectrum of the compound of any of aspects 1 to 40 or of a complex of any of aspects 43 to 56 is lower compared to a the mass spectrometric spectrum of an exemplary complex or exemplary compound, which has a one-time permanently net charge equal to or smaller than 1 as a maximum.

59. A method for mass spectrometric determination of an analyte comprising the steps of:

(a) reacting the analyte with the compound as defined in anyone of aspects 1 to 40, whereby a complex as defined in anyone of aspects 43 to 56 is formed, (b) subjected the complex from step (a) to a mass spectrometric analysis.

60. The method of aspect 59, wherein step (b) comprises:

(i) subjecting an ion of the complex to a first stage of mass spectrometric analysis, whereby the ion of the complex is characterized according to its mass/charge (m/z) ratio, (ii) causing fragmentation of the complex ion, whereby a first entity, particularly a low-molecular weight entity, is released and a daughter ion of the complex is generated, wherein the daughter ion of the complex differs in its m/z ratio from the complex ion, and (iii) subjecting the daughter ion of the complex to a second stage of mass spectrometric analysis, whereby the daughter ion of the complex is characterized according to its m/z ratio, and/or wherein (ii) may further comprise alternative fragmentation of the complex ion, whereby a second entity different from the first entity is released and a second daughter ion of the complex is generated, and wherein (iii) may further comprise subjecting the first and second daughter ions of the complex to a second stage of mass spectrometric analysis, whereby the first and second daughter ions of the complex are characterized according to their m/z ratios, wherein the m/z ratio of the first daughter ion and/or the second daughter ion is greater than the m/z ratio of ion of the complex.

61. The method of aspect 59 or 60, wherein a further step (a') before step (a) comprises: (a') subjecting the ion of the complex or an ion of the compound an ion exchange of the counter ion, wherein in particular a strongly coordinating anion, e.g. trifluoroacetate, as the counter ion is exchanged by chloride, bromide or a weekly coordinating counter ion.

62. The compound or the method of any of the proceeding aspects, wherein the fragmentation is a one-step process.

EXAMPLES

The following examples are provided to illustrate, but not to limit the presently claimed invention.

Figure 1:
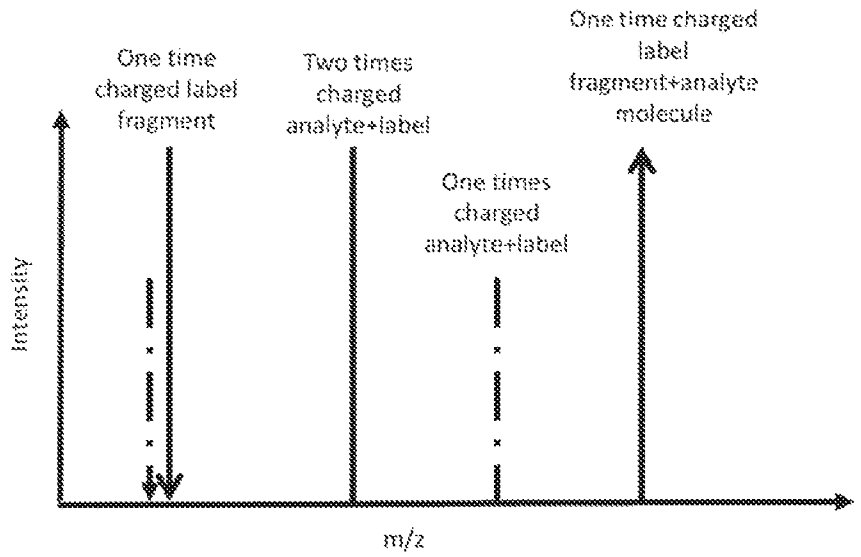
FIG. 1 shows the schematic illustration of a MS spectrum (intensity in % versus m/z): It describes the fragmentation behavior of a compound or complex of the present invention, in particular a complex comprising a two times charged labeled analyte, against a one times (single) charged analyte of precursor and fragmentation; Multiple charges can be or are respective to the resulting net charge.

FIG. 1 illustrates a schematic mass spectra of a two-times charged labeled analyte against a one times charged analyte of precursor and fragmentation thereof. In this case a two-times charged complex (parent ion) fragments into two daughter ions. The first daughter ion is a one-time charged molecule comprising label fragments and the analyte molecule and has a m/z value, which is bigger than the m3/z3 value of the two-times charged complex. The second daughter ion is a one-time charged label fragment and has a m/z value which is smaller than m3/z3. The two-times charged labeled analyte results to an MS signal enhancement. In contrast to that, a known one-time charged complex fragments only into a one time charged daughter ion, wherein the m/z value of the daughter ion is smaller than the m/z value of the known one-time charged complex. A known one-time charged complex does not fragment into a daughter ion having a m/z value bigger than the m3/z3 value of the known one-time charged complex. A known one-time charged complex does not show such a fragmentation pattern, a MS signal enhancement or better noise to signal ratio compared to a two-times charged complex.

By installing one permanent charge with one label on one reactive part of an analyte molecule the fragmentation properties are going to be from a high mass precursor ion to a low mass quantifying ion after MSMS process. This fragmentation pattern occurs if one charge (permanent or as pseudo molecular ion ($M^+H$; $M^+Na$, etc.)) is produced after ionization process or chemical derivatization. In particular, small molecules (up to ca. 2000 Da) show this fragmentation pattern of a small fragment shift from high m/z to a lower m/z values. As a result of this false positive signal from unwanted ions e.g. matrix or co-eluting/isobaric compounds with similar fragmentation pattern like the molecule of interest occur (see also FIG. 5A to FIG. 5C). This is due to similar signals during MSMS process and is therefore interfere with the quantitative signal of the desired analyte. Minor amounts of clinical relevant analytes result after a ESI (electrospray ionization) process in a two charged version as pseudo molecular ion. Those kind of molecules mostly consist of peptides, e.g. Tyr-Met-Arg-Phe-$NH_2$, or related substances, e.g. Vancomycine. The charge on those kind of molecules are derived form a (in positive ion mode) double protonation process which is dependent on the respective ion source parameters which regulates the ionization.

Figure 2:
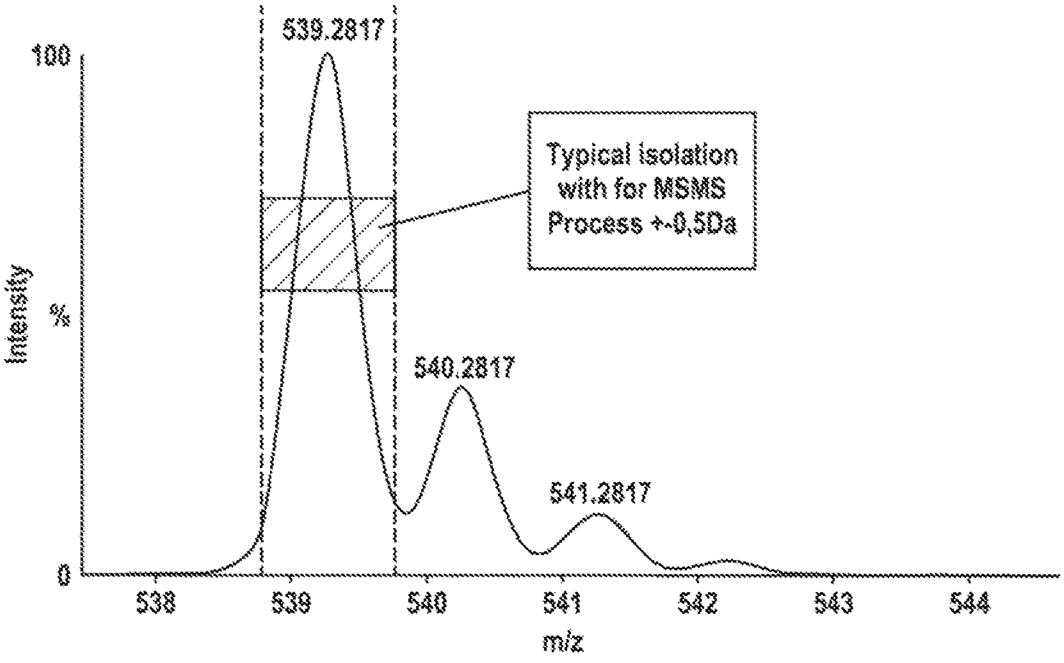
FIG. 2 shows the schematic illustration of a MS spectrum (intensity in % versus m/z): It describes the fragmentation behavior of a comparison compound, which is one times charged with a +/−0.5 Dalton window (window is represented between the two dashed lines).

FIG. 2 shows the schematic illustration of a MS spectrum (intensity in % versus m/z). It describes the fragmentation behavior of a comparison compound, which is one times charged with a +/−0.5 Dalton window (window is represented between the two dashed lines). Typical mass spectrometers with a separation power of R=2000 can separate isobaric species of 500 m/z and +−0.5 Da with is a typical isolation with for mass spectrometer in MSMS modes. If this kind of resolving power is used to enhance the selectivity of separating a precursor molecule the naturally containing isotopes do not get into the collision process for MSMS because the first isotope if one charge is added to the ionized molecule will be +0.5 Da. For higher mass molecules of approximately 2000m/z the first isotopic peaks get into the collision cell after separation of the precursor molecule. Most clinical relevant small molecule analytes are below 2000 Da. Therefore the intensity of the naturally occurring isotopes get lost during fragmentation process. For a molecule containing CHNOS this is up to ca. 30% of intensity at a mass of ca. 500 Da.

Figure 3:
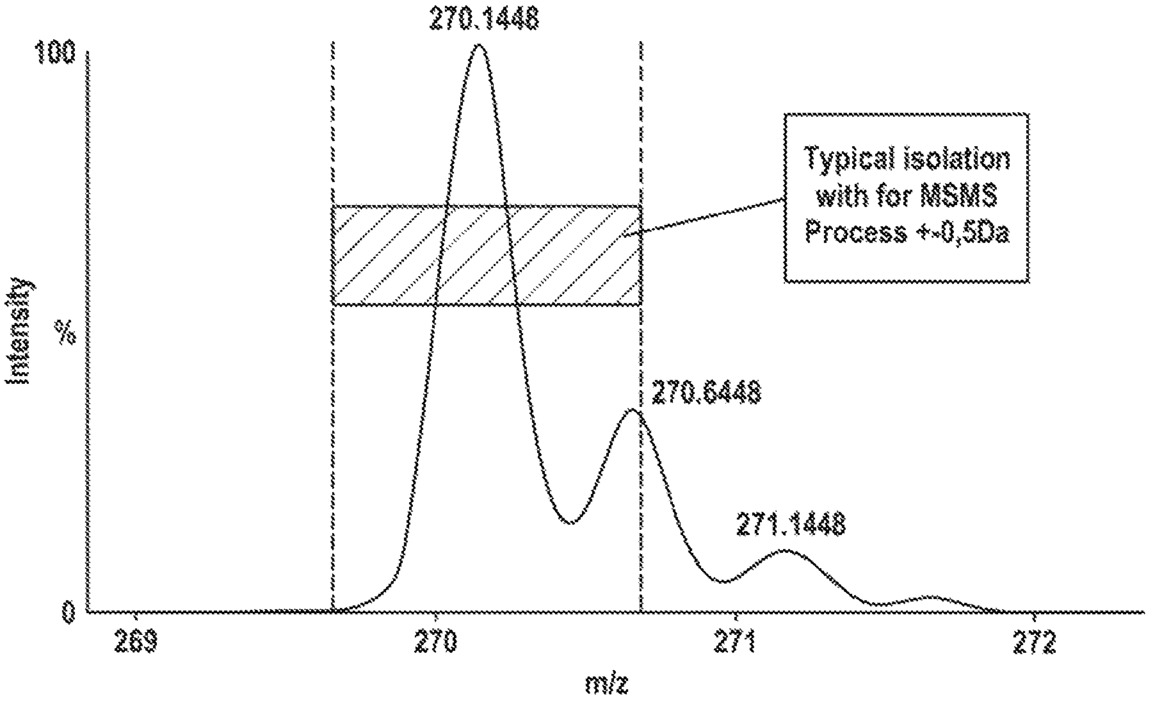
FIG. 3 shows the schematic illustration of a MS spectrum (intensity in % versus m/z): It describes the fragmentation behavior of a compound or complex of the present invention, which is two times charged with a +/−0.5 Dalton window (window is represented between the two dashed lines).

FIG. 3 shows the schematic illustration of a MS spectrum (intensity in % versus m/z). It describes the fragmentation behavior of a compound or complex of the present invention, which is two times charged with a +/−0.5 Dalton window (window is represented between the two dashed lines).

A two times charged (as well as respective multiple times charged) molecule is advantageous compared to a one time charged molecule (see FIG. 2). It is a fixed isolation with in a mass spectrometer is set due to the effect that that first naturally containing isotope will be separated to the monoisotopic peak by one charge with +1 Da and with two charged with +0.5 Da. Therefore ca. 30% more ions can be used for the further MSMS Process.

FIG. 4A to FIG. 4E show a LLOQ (lower limit of quantification) of a two times charged complex (analyte: estradiol or derivatives thereof; compound: two-times permanently positive charged compound, estradiol conjugated with label 6, label 6 also named as RHA256). With a permanent positive label a better signal to noise ratios of analyte vs. analyte-compound can be achieved which is directly linked to an enhanced detection limit and therefore the respective enhancement factor.

FIG. 5A to FIG. 5C show the background noise of a blank sample using transition of one time charged molecules (RHA139F2 (FIG. 5A) and RHA171F2 (FIG. 5B)) in comparison to a two times charged molecule (Estradiol conjugated with label 6 (FIG. 5C)). The unusual fragmentation pathway from a lower m/z precursor or lower m/z compound to a higher m/z quantifying ion (daughter ion) results in a significantly lower background noise. A resulting 0.4 pg/ml detection limit compared to a comparable underivatized workflow (estradiol native detection limit ca. 5 ng/ml positive mode and ca. 30 pg/ml in negative ion mode) show the detection limit enhancement of the labeling. The background noise of a estradiol conjugated with label 6 mass spectrum is better than that of RHA139F2 and RHA171F2 mass spectrum. The structure of RHA139F2, RHA171F2 and estradiol conjugated with label 6 are:

estradiol conjugated with label 6

RHA139F2

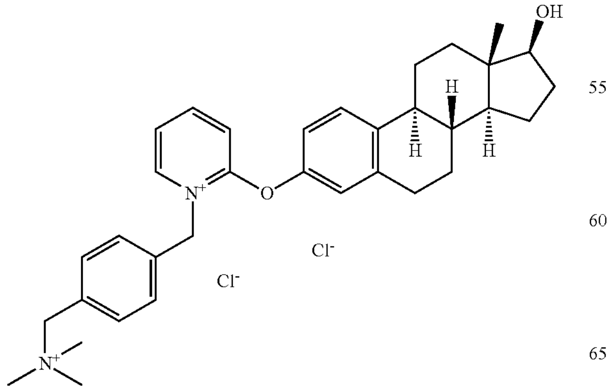

-continued

RHA171F2

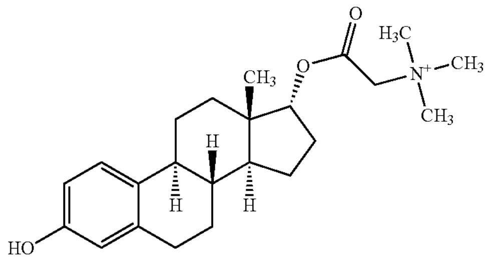

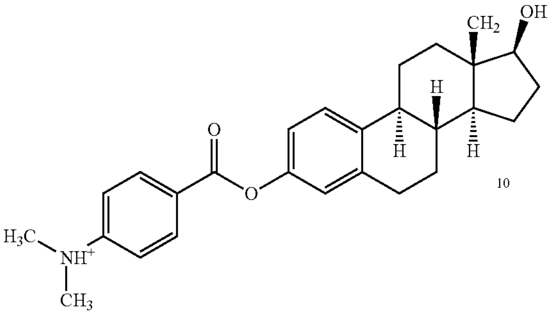

10

By fragmentation of a two times permanently charged molecule or complex the two permanent installed charges distribute after fragmentation between the label information containing ion and the analyte information containing ion. These two ions will appear at least with comparable intensities without losing ions and therefore can serve very good as qualifier and quantifier ion.

By using this concept which is seldom for all interfering substances the selectiveness of the MSMS process is enhanced and background ions depleted. (see FIG. 4A to FIG. 4E and FIG. 5A to FIG. 5C).

FIG. 6 shows a mass spectra of a two times positive charged complex (analyte-label 6-complex). The complex comprises estradiol or derivative thereof as an analyte of interest and estradiol conjugated with label 6 as a two-times permanently positive charged compound. The unfragmented complex has a m3/z3 value of 256.16 (parent ion). The one-time permanently positive charged daughter ion comprising estradiol and compound fragments has a m/z value of 349.20 which is more than the m3/z3 value of the parent ion. Two further daughter ions each comprising fragments of the compound have a m/z value of 198.09 and 104.05, respectively.

If the concept of multiple positive and one negative (or vice versa) charges are used within one label and the opposite charge (according to the resulting charge of the precursor) is separated after MSMS process the quantification of the analyte can be done in a different ionization mode than the ionization mode for precursor isolation. This can be done by a fast switching between positive and negative ionization mode.

The here described label capabling to install multiple permanent charges (either x-times positive charges, y-times negative charges or a (x-y)-times positive and negative charges as net charge) show a fragmentation behavior to one or multiple fragments and bear information for the part of the labeling and the part for the analyte molecule ion after fragmentation. Thus the MS signal enhancement of the analyte results which is, e.g. important for low abundant analytes.

FIG. 7 shows the schematic illustration of peak "splitting": It describes the capability of the chromatographic system to separate the different isomers resulting from the derivatization reaction of the analyte molecule from each other.

FIG. 8 shows schematic representation of the workflow determining the enhancement factor of a labeled analyte in comparison to unlabeled analyte.

FIG. 9A and FIG. 9B show the detection of the signal quenching effect of TFA on doubly charged derivatives/compounds.

FIG. 9A shows the respective MSMS transition of label 15 (double charged molecular ion to singly charged fragment) as derivatization agent/compound for testosterone at 500 pg/ml TFA free.

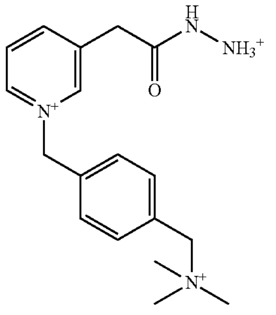

RHA330= Label 15

FIG. 9B shows respective MSMS transition of label 15 (double charged molecular ion to singly charged fragment) as derivatization agent/compound for testosterone at 500 pg/ml with TFA addition.

The addition or presence of TFA is quenching the doubly charged ion which results in a significantly lower signal compared to a TFA free system.

The complex comprising label 15 as the compound and testosterone as the analyte with TFA or without TFA is prepared as follows:

Analytical Derivatization of Testosterone Using Label 15

A 500 ng/ml solution (S1) of testosterone was prepared in methanol. A solution (S2) compared to the solution (S1) containing an excess of either of the derivatization reagents/label 15, diluted in methanol (molar ratio >1000) was added and the solution was acidified with glacial acidic acid (20% v/v). The solution S1 and S2 were mixed resulting in solution S3, and held for 2 h at 65° C. followed by 12 h at room temperature and a dilution step with methanol to reach a concentration of 500 pg/ml with 1 ml total volume.

The so prepared molecule in its metabolic solution was splitted 1:1 (v/v) in the solutions (S3-A) and (S3-B). The solution S3-B was spiked with 40 μl of water/TFA while S3-A was only spiked with 40 μl water.

Both solutions were measured in ESI-positive-full scan mode using the mass to display of m/z=302.71 Da which corresponds to the doubly charged derivate of testosterone.

As seen in FIG. 9A (ESI-MS of m/z=302.7 Da using solution S3-A; upper chromatogram and ESI-MS of m/z=302.7 Da using solution S3-B; lower chromatogram), the peak heights of the chromatogram using S3-B is significantly lower than for S3-A. A quenching of the doubly changed peak can be observed by addition of strongly coordinating anions like TFA which inhibits the doubly changed molecular ion and results therefore in the occurrence of the pseudo molecular ion [M+TFA]+ which is disadvantages for quantitative analytics.

Chromatographic and MS Parameters

| | | |
|---|---|---|
| Polarity | ES+ | |
| Calibration | Static 2 | |
| Soft Transmission Mode | Disabled | |
| Capillary (kV) | 3.00 | 3.14 |
| Cone (V) | 50.00 | 144.92 |
| Source Offset (V) | 30.0 | |
| Source Temperature (° C.) | 140 | 140 |
| Desolvation Temperature (° C.) | 350 | 350 |
| Cone Gas Flow (L/Hr) | 150 | 149 |
| Desolvation Gas Flow (L/Hr) | 1000 | 990 |
| Collision Gas Flow (mL/Min) | 0.15 | 0.14 |
| Nebuliser Gas Flow (Bar) | 7.00 | 6.52 |
| LM 1 Resolution | 3.0 | |
| HM 1 Resolution | 15.0 | |
| Ion Energy 1 | −0.2 | |
| MS Mode Collision Energy | 4.00 | |
| MSMS Mode Collision Energy | 2.00 | |
| MS Mode Entrance | 1.00 | |
| MS Mode Exit | 1.00 | |
| Gas On MS Mode Entrance | 1.00 | |
| Gas On MS Mode Exit | 1.00 | |
| Gas On MSMS Mode Entrance | 1.00 | |
| Gas On MSMS Mode Exit | 1.00 | |
| Gas Off MS Mode Entrance | 30.00 | |
| Gas Off MS Mode Exit | 30.00 | |
| Gas Off MSMS Mode Entrance | 30.00 | |
| Gas Off MSMS Mode Exit | 30.00 | |
| ScanWave MS Mode Entrance | 1.00 | |
| ScanWave MS Mode Exit | 1.00 | |
| ScanWave MSMS Mode Entrance | 1.00 | |
| ScanWave MSMS Mode Exit | 1.00 | |
| LM 2 Resolution | 3.0 | |
| HM 2 Resolution | 15.0 | |
| Ion Energy 2 | 0.2 | |
| Gain | 1.00 | |
| Multiplier | 513.80 | |
| Active Reservoir | C | |

-continued

| | | |
|---|---|---|
| Cone Energy Ramp: | Disabled | |
| Probe Temperature Ramp: | Disabled | |
| Collision Energy Ramp: | Disabled | |
| Instrument Parameters - Function 2: Parameter File - E:\Regulated projects\ESI-Derivatization_PDA.PRO\ACQUDB\cz20Mrz2019-testo-label-general_tuning.IPR | | |
| Polarity | ES+ | |
| Calibration | Static 2 | |
| Soft Transmission Mode | Disabled | |
| Capillary (kV) | 3.00 | 3.14 |
| Cone (V) | 50.00 | 144.92 |
| Source Offset (V) | 30.0 | |
| Source Temperature (° C.) | 140 | 140 |
| Desolvation Temperature (° C.) | 350 | 350 |
| Cone Gas Flow (L/Hr) | 150 | 149 |
| Desolvation Gas Flow (L/Hr) | 1000 | 990 |
| Collision Gas Flow (mL/Min) | 0.15 | 0.14 |
| Nebuliser Gas Flow (Bar) | 7.00 | 6.52 |
| LM 1 Resolution | 3.0 | |
| HM 1 Resolution | 15.0 | |
| Ion Energy 1 | −0.2 | |
| MS Mode Collision Energy | 4.00 | |
| MSMS Mode Collision Energy | 2.00 | |
| MS Mode Entrance | 1.00 | |
| MS Mode Exit | 1.00 | |
| Gas On MS Mode Entrance | 1.00 | |
| Gas On MS Mode Exit | 1.00 | |
| Gas On MSMS Mode Entrance | 1.00 | |
| Gas On MSMS Mode Exit | 1.00 | |
| Gas Off MS Mode Entrance | 30.00 | |
| Gas Off MS Mode Exit | 30.00 | |
| Gas Off MSMS Mode Entrance | 30.00 | |
| Gas Off MSMS Mode Exit | 30.00 | |
| ScanWave MS Mode Entrance | 1.00 | |
| ScanWave MS Mode Exit | 1.00 | |
| ScanWave MSMS Mode Entrance | 1.00 | |
| ScanWave MSMS Mode Exit | 1.00 | |
| LM 2 Resolution | 3.0 | |
| HM 2 Resolution | 15.0 | |
| Ion Energy 2 | 0.2 | |
| Gain | 1.00 | |
| Multiplier | 513.80 | |
| Active Reservoir | C | |
| Cone Energy Ramp: | Disabled | |
| Probe Temperature Ramp: | Disabled | |
| Collision Energy Ramp: | Disabled | |
| Engineers Settings: | | |
| MS1 Low Mass Position | 673 | |
| MS1 High Mass Position | 335 | |
| MS1 Low Mass Resolution | 215 | |
| MS1 High Mass Resolution | 2152 | |
| MS1 Resolution Linearity | 531 | |
| MS1 High Mass DC Balance | 0.07 | |
| MS1 DC Polarity | Negative | |
| MS2 Low Mass Position | 672 | |
| MS2 High Mass Position | 291 | |
| MS2 Low Mass Resolution | 219 | |
| MS2 High Mass Resolution | 2162 | |
| MS2 Resolution Linearity | 528 | |
| MS2 High Mass DC Balance | 0.50 | |
| MS2 DC Polarity | Negative | |
| Inter-scan delays: | | |
| Automatic Mode | | |
| MS Inter-scan delay (secs) | 0.003 | |
| Polarity/Mode switch Inter-scan delay (secs) | 0.020 | |
| Enhanced Inter-scan delay (secs) | 0.020 | |
| Inter-channel delay - See Tables | | |

MS 1 Delay Table:

| R | delay |
|---|---|
| <=1.250 | 0.001 |
| <=4.000 | 0.002 |
| <=10.000 | 0.003 |

-continued

| | |
|---|---|
| <=20.000 | 0.004 |
| >20.000 | 0.005 |

Run method parameters

| | |
|---|---|
| Waters Acquity | SDS |
| Run Time: | 6.50 min |
| Comment: | |
| Solvent Selection A: | A2 |
| Solvent SelectionB: | B1 |
| Low Pressure Limit: | 0.000 bar |
| High Pressure Limit: | 1034.200 bar |
| Solvent Name A: | Water + NH4Ac + 0.1% formic acid |
| Solvent Name B: | MeOH + NH4Ac + 0.1% formic acid |
| Switch 1: | No Change |
| Switch 2: | No Change |
| Switch 3: | No Change |
| Seal Wash: | 5.0 min |
| Chart Out 1: | System Pressure |
| Chart Out 2: | % B |
| System Pressure Data Channel: | Yes |
| Flow Rate Data Channel: | No |
| % A Data Channel: | No |
| % B Data Channel: | Yes |
| Primary A Pressure Data Channel: | No |
| Accumulator A Pressure Data Channel: | No |
| Primary B Pressure Data Channel: | No |
| Accumulator B Pressure Data Channel: | No |
| Degasser Pressure Data Channel: | No |

[Gradient Table]

| | Time(min) | Flow Rate | % A | % B | Curve |
|---|---|---|---|---|---|
| 1. | Initial | 0.400 | 60.0 | 40.0 | Initial |
| 2. | 0.50 | 0.400 | 60.0 | 40.0 | 6 |
| 3. | 3.00 | 0.400 | 10.0 | 90.0 | 6 |
| 4. | 5.00 | 0.400 | 10.0 | 90.0 | 6 |
| 5. | 5.10 | 0.400 | 60.0 | 40.0 | 6 |
| 6. | 6.50 | 0.400 | 60.0 | 40.0 | 6 |

| | |
|---|---|
| Run Events: | Yes |
| Gradient Start (Relative to Injection): | 0 uL |
| 2 D Repeat: | No |
| Waters Acquity | PDA |
| Run Time: | 6.50 min |
| PDA Detector Type: | UPLC LG 500 nm |
| Lamp: | On |
| Sampling Rate: | 10 points/sec |
| Filter Time Constant: | 0.2000 sec |
| Exposure Time: | Auto msec |
| Interpolate 2nd order filter Region: | No |
| Use UV Blocking Filter: | No |
| 3 D Channel . . . | |
| Range: | 200-400 |
| Resolution: | 2.4 nm |
| Initial Switch 1: | No Change |
| Initial Switch 2: | No Change |
| Waters ACQUITY FTN AutoSampler | |
| Run Time: | 6.50 min |
| Comment: | |
| Load Ahead: | Disabled |
| Loop Offline: | Automatic min |
| Wash Solvent Name: | ACN:water |
| Pre-Inject Wash Time: | 15.0 sec |
| Post-Inject Wash Time: | 15.0 sec |
| Purge Solvent Name: | ACN:water |
| Dilution: | Disabled |
| Dilution Volume: | 0 uL |
| Delay Time: | 0 min |
| Dilution Needle Placement: | Automatic mm |
| Target Column Temperature: | 40.0 C. |
| Column Temperature Alarm Band: | Disabled |
| Target Sample Temperature: | 6.0 C. |
| Sample Temperature Alarm Band: | Disabled |

-continued

| | |
|---|---|
| Syringe Draw Rate: | Automatic |
| Needle Placement: | 0.5 mm |
| Pre-Aspirate Air Gap: | Automatic |
| Post-Aspirate Air Gap: | Automatic |
| Column Temperature Data Channel: | No |
| Room Temperature Data Channel: | Yes |
| Sample Temperature Data Channel: | Yes |
| Sample Organizer Temperature Data Channel: | No |
| Sample Pressure Data Channel: | No |
| Preheater Temperature Data Channel: | No |
| Seal Force Data Channel: | No |
| No Injection Mode Enabled: | No |
| Autoaddition Mix Stroke Cycles: | Automatic |
| Autoaddition Mix Stroke Volume: | Automatic uL |
| Active Preheater: | Use Console Configuration |
| Run Events: | No |
| Sample Run Injection Parameter | |
| Injection Volume (ul) - 5.00 | |
| Function 1 | |
| Scans in function: | 738 |
| Cycle time (secs): | Automatic |
| Inter Scan Delay (secs): | Automatic |
| Inter Channel Delay (secs): | Automatic |
| Span (Da): | 0.500 |
| Start and End Time(mins): | 0.000 to 5.000 |
| Ionization mode: | ES+ |
| Data type: | Enhanced SIR or MRM |
| Function type: | MRM of 1 channel |
| Chan Reaction | Dwell(secs) Cone Volt. Col.Energy Delay(secs) |

| | | | | | | Compound |
|---|---|---|---|---|---|---|
| 1: | 289.25 > 108.78 | 0.200 | Tune | 25.0 | Auto | Testosterone |

| | |
|---|---|
| Function 2 | |
| Scans in function: | 737 |
| Cycle time (secs): | Automatic |
| Inter Scan Delay (secs): | Automatic |
| Inter Channel Delay (secs): | Automatic |
| Span (Da): | 0.500 |
| Start and End Time(mins): | 0.000 to 5.000 |
| Ionization mode: | ES+ |
| Data type: | Enhanced SIR or MRM |
| Function type: | MRM of 1 channel |
| Chan Reaction | Dwell(secs) Cone Volt. Col.Energy Delay(secs) |

| | | | | | | Compound Formula\|Mass |
|---|---|---|---|---|---|---|
| 1: | 624.40 >203.00 | 0.200 | Tune | 40.0 | Auto | DMA041 CE40420.2 |

| | |
|---|---|
| Function 3 | |
| Scans in function: | 3901 |
| Function type: | Diode Array |
| Wavelength range (nm): | 200 to 400 |

From linear calibration curves the respective detection limits were obtained by using the procedure described in DIN EN ISO 32645. Enhancement factors can be calculated based upon the labeled analyte, e.g. testosterone, Limit of Detection (LOD) in comparison to the underivatized analyte, e.g. testosterone, LOD. The principle workflow is shown in FIG. 8.

FIG. 10A to FIG. 10D show the fragmentation pattern of an analyte-label 17-complex at different fragmentation energies (5V to 25V).

Figure 10A:
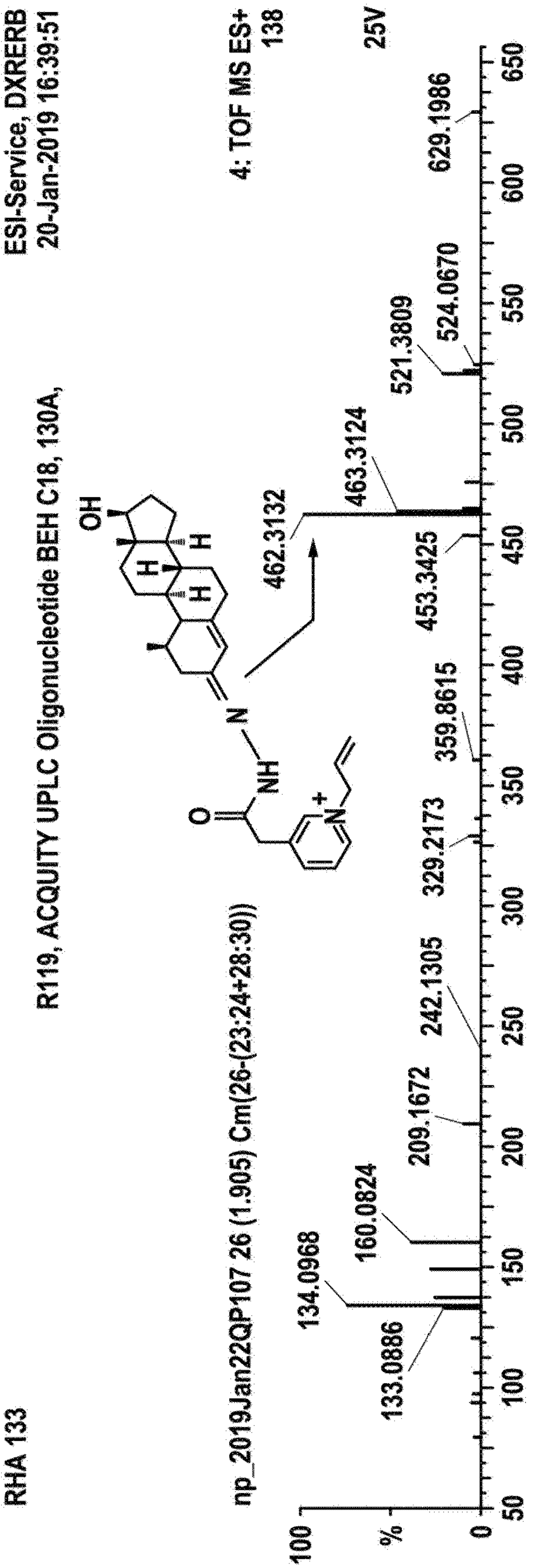
Figure 10B:
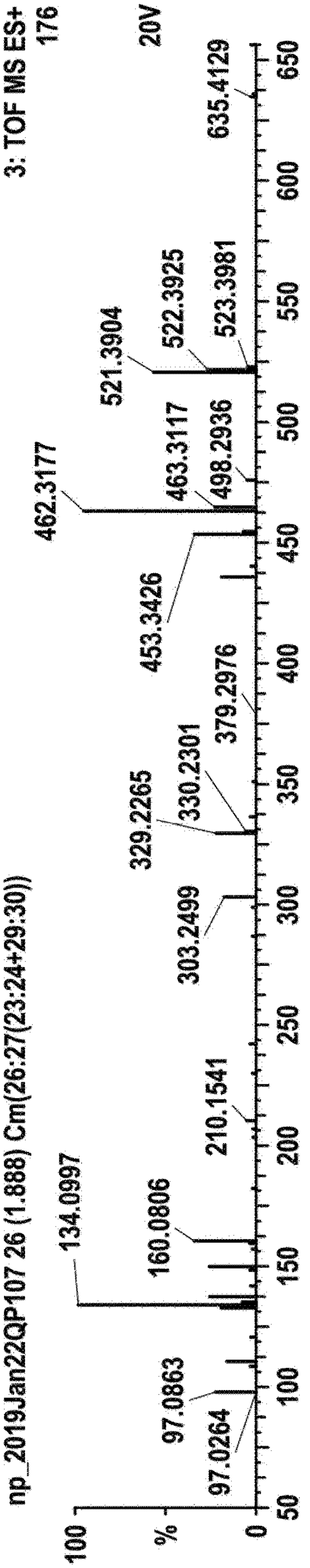
Figure 10C:
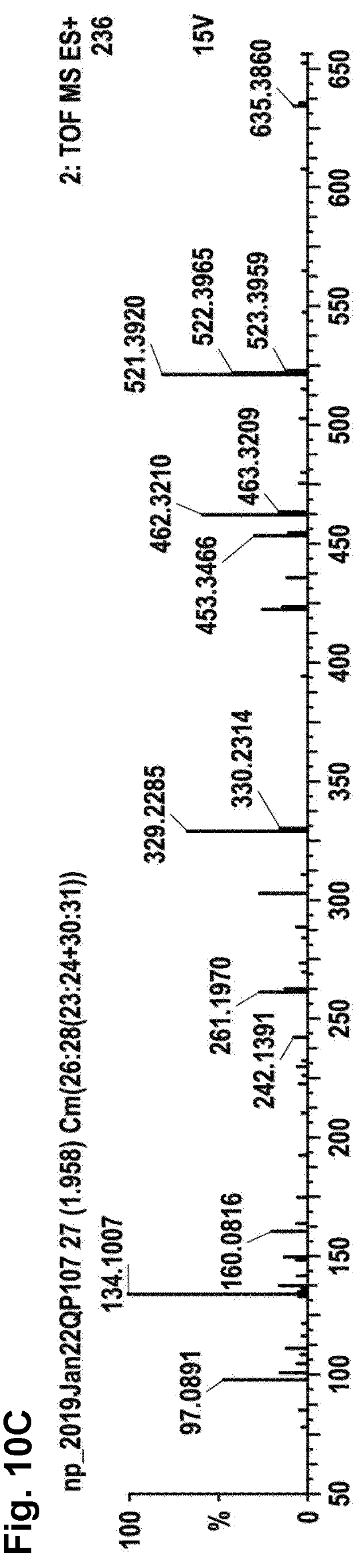
Figure 10D:
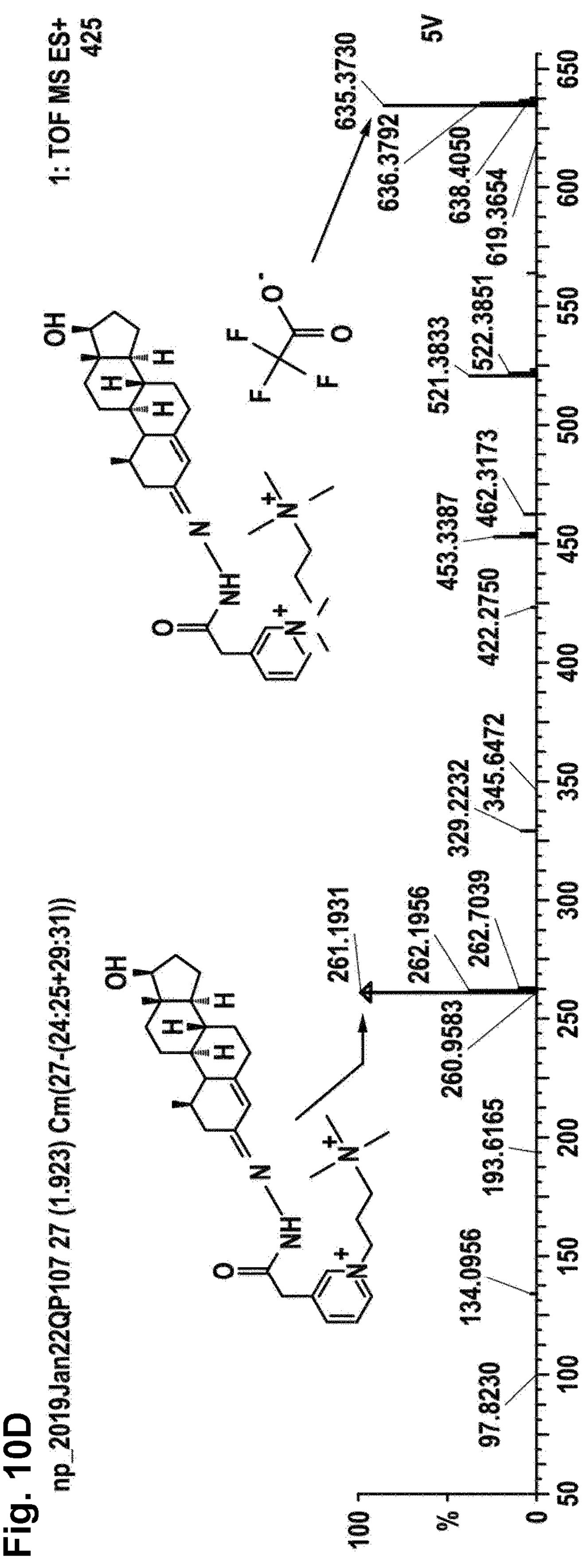

FIG. 10D shows the fragmentation pattern of the complex at 5V. The parent ion with a m3/z3 value of 261 is fragmented into a first daughter ion having a m4/z4 value of 462. Further ions, e.g. a TFA adduct having a m/z value of 635 and a second daughter ion having a m/z value of 453 are shown. By increasing the fragmentation energy from 5 V to 25 V (FIG. 10A to FIG. 10D), the intensity of the first daughter ion increases and intensities of the TFA adduct and parent ion decrease. The best performance of the fragmentation energy can be detected. It is well-known to the skilled person how to choose the best performance of the fragmentation energy, e.g. by using a computer (software or manual). The optimized fragmentation energy can be tuned by routine measurement.

FIG. 11 shows the fragmentation pattern of an analyte-label 15-complex.

The complex is formed by the analyte testosterone and the compound label 15, which are covalently linked to each other. The complex (parent ion) comprises two permanent charges and has a m3/z3 ratio of 291. The complex is fragmented into at least four daughter ions, each having a m/z ratio more than the m/z ratio of the parent ion (m/z: 302, 328, 510 and 524). The possible structures of these daughter ions are shown in FIG. 11. Further daughter ions having a m/z ratio smaller than m3/z3 are detected.

The here described label capabling to install two permanent charges show a fragmentation behavior to one or multiple fragments and bear information for the part of the labeling and the part for the analyte molecule ion after fragmentation. Thus the MS signal enhancement of the analyte results which is, e.g. important for low abundant analytes.

General Synthetic Protocol 1

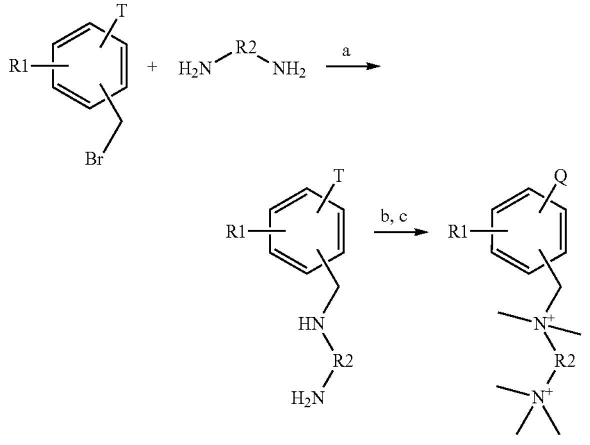

T=precursor of reacting functional group Q

R1 and R2 can be selected independently from each other from the following groups:

R1=methoxy, ethoxy, propoxy, butoxy, pentoxy, hexoxy, cyclopropoxy, cyclobutoxy, cyclopentoxy, cyclohexoxy, phenoxy, methylthioxy, ethylthioxy, propylthioxy, phenthioxy, acyl, formyl, methoxycarbonyl, ethoxycarbonyl, propoxycarbonyl, butoxycarbonyl, benzyloxycarbonyl, benzoyloxy, acetoxy, fluoro, chloro, bromo, iodo, hydroxy, phenyl, benzyl, methyl, ethyl, propyl, butyl, pentyl, hexyl, cyclopropyl, cyclobutyl, cyclopentyl, cyclohexyl, aryl, heteroaryl.

R2=methylene, ethylene, propylene, butylene, pentylene, hexylene, aryl, heteroaryl.

Reaction Conditions:

a=alkylation step, different solvents and temperature:

b=methylation step, different solvents, MeI;

c=transformation of T in Q: for example: $N_2H_4$, MeOH or $SOCl_2$, DCM or iodobenzene diacetate, MeOH The selection of the solvents and/or temperature depends on the nature of the produced product. It is well-known to the skilled person how to choose the appropriate solvent and/or temperature.

General Synthetic Protocol Alkylation Step a

The methyl ester reagent (4.35 mmol) was dissolved in 15 mL of solvent and the ethylenediamine reagent (10.95 mmol) was added. The reaction mixture was stirred at (room temperature or 70° C.) for (2-10 h) and subsequently concentrated in vacuo. The crude product was co-evaporated with DMF (3×15 mL) and re-dissolved in a mixture of 20 mL acetonitrile and 10 mL ethyl acetate. The solution was stored at −20° C. for 16 h in order to precipitate the quaternary ammonium salt. The supernatant was removed and the resulting solid was dried in vacuo.

General Synthetic Protocol Methylation Step b

The crude material (step a) was dissolved in a mixture in solvent and methyl iodide (7.5 mmol) was added. The reaction mixture was stirred at room temperature for 16 h and subsequently dried in vacuo. Next, the crude bis-quaternary ammonium salt was co-evaporated with acetonitrile/methanol (2/1, 2×30 mL).

General Synthetic Protocol Step c

The crude material (step b) was dissolved in acetonitrile/methanol and hydrazine hydrate (15 mmol) was added. The reaction mixture was stirred at room temperature for 4 h and subsequently dried in vacuo. The crude product obtained was purified by preparative RP-HPLC to yield the desired product as a crystalline solid. Final conversion of the TFA salt into the corresponding formiate salt was achieved by using a formic acid activated anion exchange resin (Lewatit-MP-62 free base polymer).

General Synthetic Protocol 2

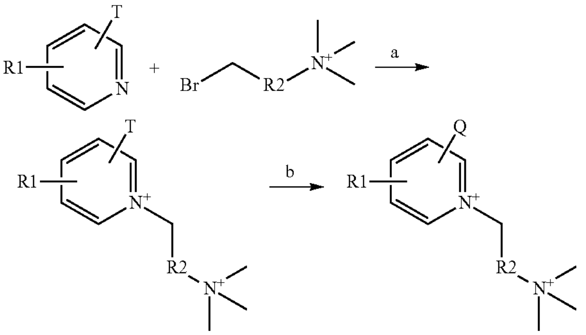

T=precursor of reacting functional group Q

R1 and R2 can be selected independently from each other from the following groups:

R1=methoxy, ethoxy, propoxy, butoxy, pentoxy, hexoxy, cyclopropoxy, cyclobutoxy, cyclopentoxy, cyclohexoxy, phenoxy, methylthioxy, ethylthioxy, propylthioxy, phenthioxy, acyl, formyl, methoxycarbonyl, ethoxycarbonyl, propoxycarbonyl, butoxycarbonyl, benzyloxycarbonyl, benzoyloxy, acetoxy, fluoro, chloro, bromo, iodo, hydroxy, phenyl, benzyl, methyl, ethyl, propyl, butyl, pentyl, hexyl, cyclopropyl, cyclobutyl, cyclopentyl, cyclohexyl, aryl, heteroaryl.

R2=methylene, ethylene, propylene, butylene, pentylene, hexylene, aryl, heteroaryl.

Reaction Conditions:

a=alkylation step, different solvents and temperature b=transformation of T in Q: for example: $N_2H_4$, MeOH or $SOCl_2$, DCM or iodobenzene diacetate, MeOH General Synthetic Protocol Alkylation Step a Pyridine reagent (0.50 mmol) and (bromomethyl)trimethylammonium reagent (0.60 mmol) were dissolved in 1 mL of dry DMF. The reaction mixture was stirred at (room temperature (r.t) or 70° C.) for (24-36 h). The solvent was removed under vacuum and the residue was purified by preparative HPLC. The pure fractions were collected and concentrated under vacuum to give the products as solids.

General Synthetic Protocol Step b

PTAD-Py reagent (0.029 mmol) was dissolved in MeOH (500 μL). A solution of iodobenzene diacetate (0.033 mmol) in MeOH (500 μL) was added to the first solution. The reaction mixture was stirred at r.t. for 15 min. The solvent was removed under vacuum and the residue was used directly without further purification.

General Synthetic Protocol 3

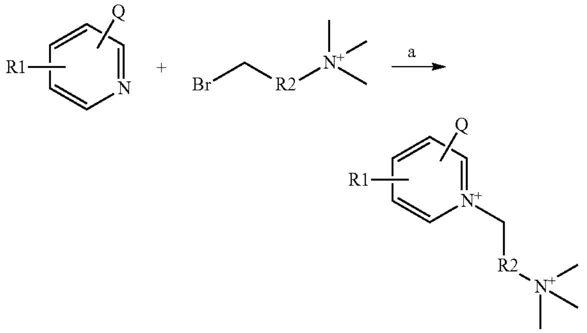

R1 and R2 can be selected independently from each other from the following groups:

R1=methoxy, ethoxy, propoxy, butoxy, pentoxy, hexoxy, cyclopropoxy, cyclobutoxy, cyclopentoxy, cyclohexoxy, phenoxy, methylthioxy, ethylthioxy, propylthioxy, phenthioxy, acyl, formyl, methoxycarbonyl, ethoxycarbonyl, propoxycarbonyl, butoxycarbonyl, benzyloxycarbonyl, benzoyloxy, acetoxy, fluoro, chloro, bromo, iodo, hydroxy, phenyl, benzyl, methyl, ethyl, propyl, butyl, pentyl, hexyl, cyclopropyl, cyclobutyl, cyclopentyl, cyclohexyl, aryl, heteroaryl.

R2=methylene, ethylene, propylene, butylene, pentylene, hexylene, aryl, heteroaryl.

Reaction Conditions:

a=alkylation step, different solvents and temperature

General Synthetic Protocol Alkylation Step a

2-Fluoropyridine reagent (0.36 mmol) and (bromomethyl)trimethylammonium reagent (0.46 mmol) were dissolved in 1 mL of dry DMF. The reaction mixture was stirred at (r.t or 90° C.) for (24-48 h). The solvent was removed under vacuum and the residue was purified by preparative HPLC. The pure fractions were collected and concentrated under vacuum to give the product as a colourless oil.

General Synthetic Protocol 4

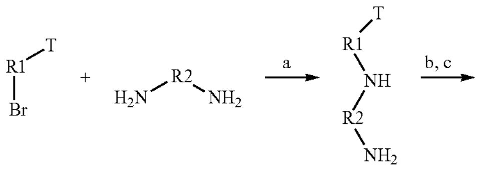

-continued

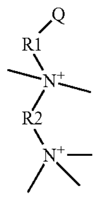

T=precursor of reacting functional group Q

R1 and R2 can be selected independently from each other from the following groups:

R1=methylene, ethylene, propylene, butylene, pentylene, hexylene, aryl, heteroaryl.

R2=methylene, ethylene, propylene, butylene, pentylene, hexylene, aryl, heteroaryl.

Reaction Conditions:

a=alkylation step, different solvents and temperature b=methylation step, different solvents, MeI;

c=transformation of T in Q: for example: $N_2H_4$, MeOH or $SOCl_2$, DCM or iodobenzene diacetate, MeOH Example 1: Label 13

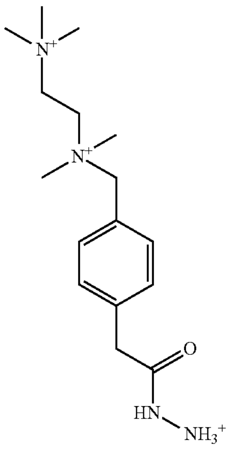 [SMILES: C[N+](C)(C)CC[N+](C)(C)Cc1ccc(CC(=O)N[NH3+])cc1]

Synthesis of Label 13

Synthesis of [4-[2-(azaniumylamino)-2-oxo-ethyl]phenyl]methyl-dimethyl-[2-(trimethylammonio)ethyl]ammonium;2,2,2-trifluoroacetate

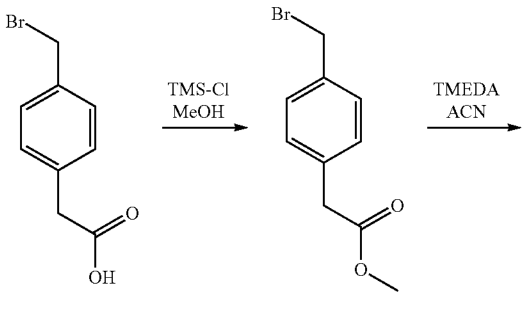

-continued

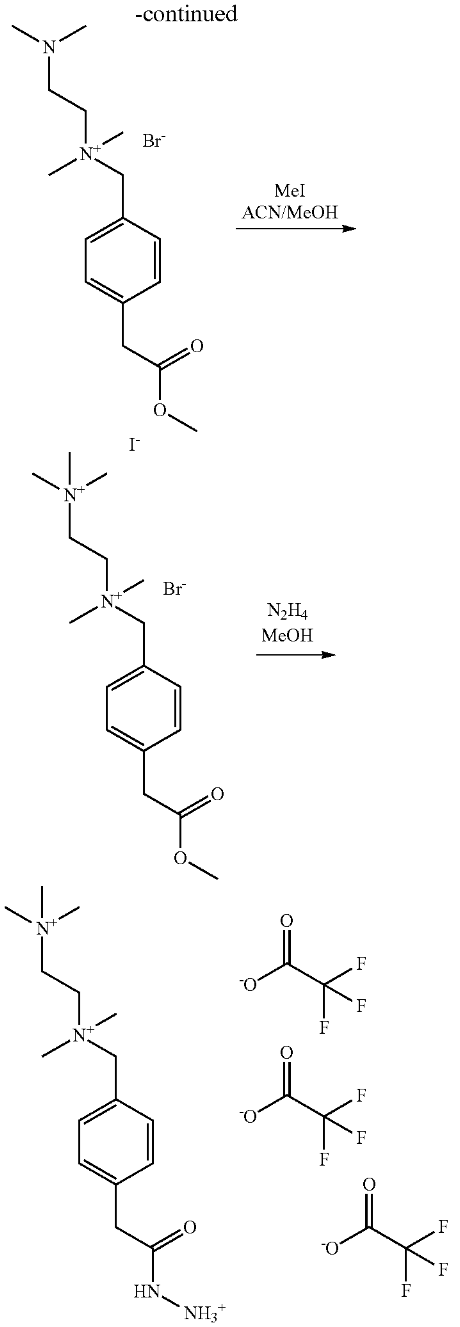

[4-[2-(azaniumylamino)-2-oxo-ethyl]phenyl]methyl-dimethyl-[2-(trimethylammonio)ethyl]ammonium;2,2,2-trifluoroacetate Bromomethylphenylacetic acid (4.35 mmol) was dissolved in 15 ml of methanol. Trimethylsilylchloride (0.87 mmol) was added and the reaction was stirred for 2 h at room temperature. The reaction mixture was concentrated in vacuo and the residual was co-evaporated with methanol (2×15 ml). The crude methylester was dissolved in 15 ml acetonitrile and tetramethylethylenediamine (10.95 mmol) was added. The reaction mixture was stirred at 70° C. for 5 h and subsequently concentrated in vacuo. The crude product was co-evaporated with DMF (3×15 ml) and re-dissolved in a mixture of 20 mL acetonitrile and 10 mL ethyl acetate. The solution was stored at −20° C. for 16 h in order to precipitate the quaternary ammonium salt. The supernatant was removed and the resulting solid was dried in vacuo. The crude material was dissolved in a mixture of acetonitrile/methanol (2/1, 30 mL) and methyliodide (7.5 mmol) was added. The reaction mixture was stirred at room temperature for 16 h and subsequently dried in vacuo. Next, the crude bis-quaternary ammonium salt was coevaporated with acetonitrile/methanol (2/1, 2×30 mL), dissolved in acetonitrile/methanol (1/4, 40 mL) and hydrazine hydrate (15 mmol) was added. The reaction mixture was stirred at room temperature for 4 h and subsequently dried in vacuo. The crude product obtained was purified by preparative RP-HPLC to yield the desired product (16% over 4 steps) as a crystalline solid. Final conversion of the TFA-salt into the corresponding formiate-salt was achieved by using a formic acid activated anion exchange resin (Lewatit-MP-62 free base polymer).

HPLC-MS (m/z) $[M^{2+}+TFA]^+$ calcd 407.5, found 407.3.

Preparation of Label 13-Analyte Derivative (Complex) and its Analysis Via MS

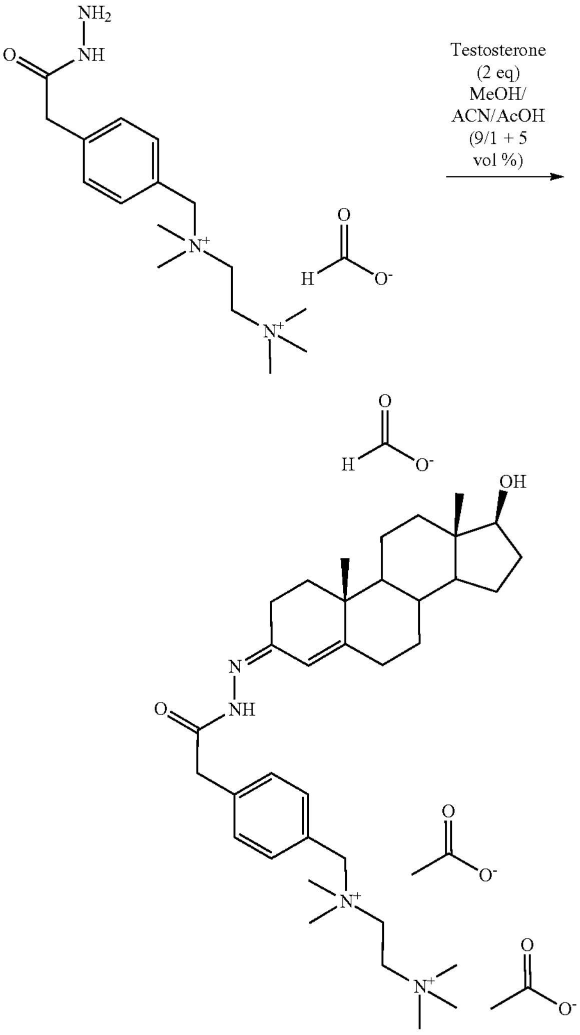

Label 13 (120 mg, 190 μmol) and testosterone (100 mg, 350 μmol, 1.8 eq) were dissolved in in 5 mL of ACN/MeOH/AcOH (10/90+5 vol %) and the mixture stirred at room temperature. After 16 h, the reaction mixture was concentrated in vacuo and the crude product was subjected to HPLC purification (Triart C18 20×250 mm, linear gradient: 20% to 100% B in 30 min; A=water; B=ACN). Lyophilization afforded the desired conjugate.

HPLC-MS (m/z) $[M2+FA]^+$ calcd 609.9, found 609.8.

Example 2: Label 14

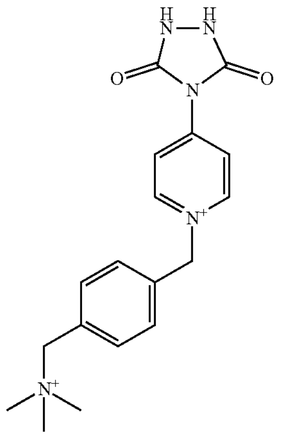 [SMILES: C[N+](C)(C)Cc1ccc(C[n+]2ccc(-n3c(=O)[nH][nH]c3=O)cc2)cc1]

Synthesis of Label 14

Synthesis of [4-[[4-(3,5-dioxo-1,2,4-triazolidin-4-yl)pyridin-1-ium-1-yl]methyl]phenyl]methyl-trimethyl-ammonium trifluoroacetate

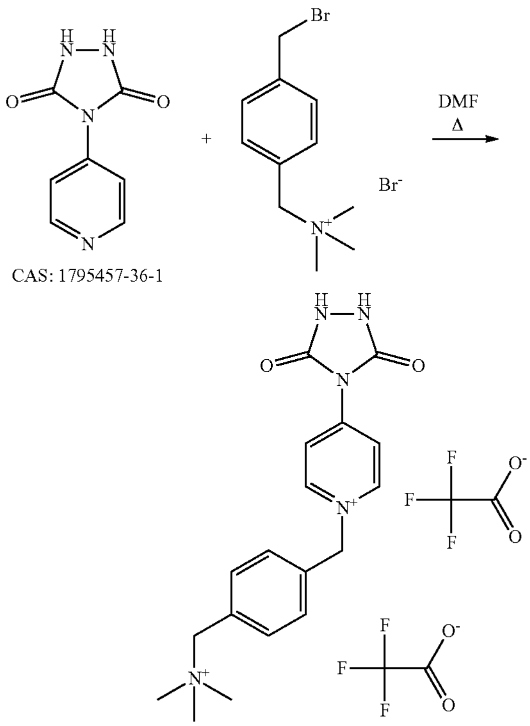

[4-[[4-(3,5-dioxo-1,2,4-triazolidin-4-yl)pyridin-1-ium-1-yl]methyl]phenyl]methyl-trimethyl-ammonium trifluoroacetate 4-(Pyridin-4-yl)-1,2,4-triazolidine-3,5-dione (0.50 mmol) and 4-(bromomethyl)benzyl trimethylammonium bromide (0.60 mmol) [synthesized as previously reported in *Polym. Chem.* 2014, 5, 1180-1190] were dissolved in 1 mL of dry DMF. The reaction mixture was stirred at 70° C. for 36 h. The solvent was removed under vacuum and residue was purified by preparative HPLC. The pure fractions were collected and concentrated under vacuum to give the products (78 mg, 24% yield) as solids.

HPLC Method C-18 Column:

0 min: 100% $H_2O$ 0.1% TFA, 0% $CH_3CN$ 0.1% TFA;

0-20 min: 100% $H_2O$ 0.1% TFA, 0% $CH_3CN$ 0.1% TFA;

20-60 min: 70% $H_2O$ 0.1% TFA, 30% $CH_3CN$ 0.1% TFA;

60-64 min: 2% $H_2O$ 0.1% TFA; 98% $CH_3CN$ 0.1% TFA;

64-74 min: 2% $H_2O$ 0.1% TFA; 98% $CH_3CN$ 0.1% TFA;

74-79 min: 60% $H_2O$ 0.1% TFA; 40% $CH_3CN$ 0.1% TFA;

79-90 min: 60% $H_2O$ 0.1% TFA; 40% $CH_3CN$ 0.1% TFA.

$^1H$ NMR (400 MHz, METHANOL-$d_4$) δ ppm 3.10 (s, 9H) 4.55 (s, 2H) 5.85 (s, 2H) 7.61-7.70 (m, 4H) 8.85-8.89 (m, 2H) 9.01-9.06 (m, 2H).

HPLC-MS (m/z) $[M]^{2+}$ calcd 170.59, found 170.79.

Preparation of Label 14-Analyte Derivative (Complex) and its Analysis Via MS

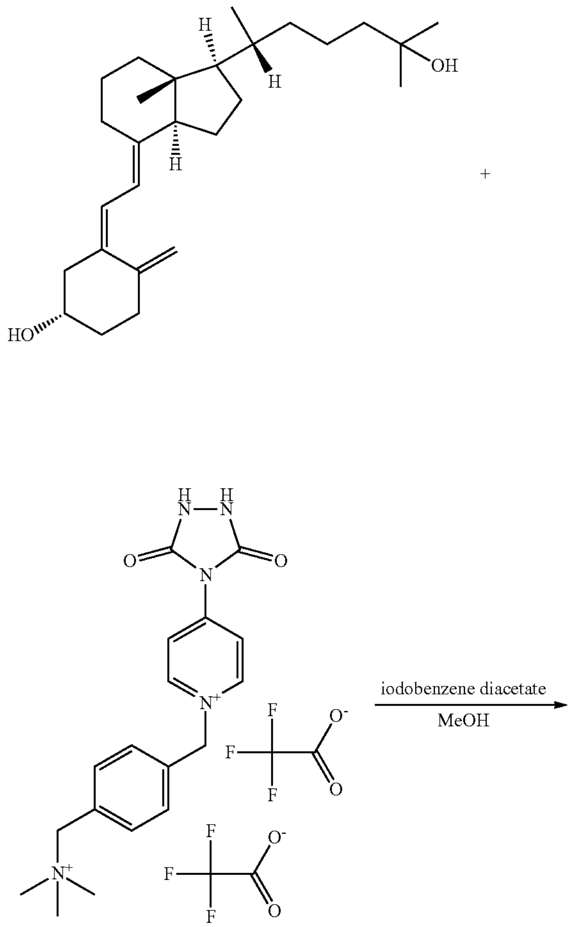

-continued

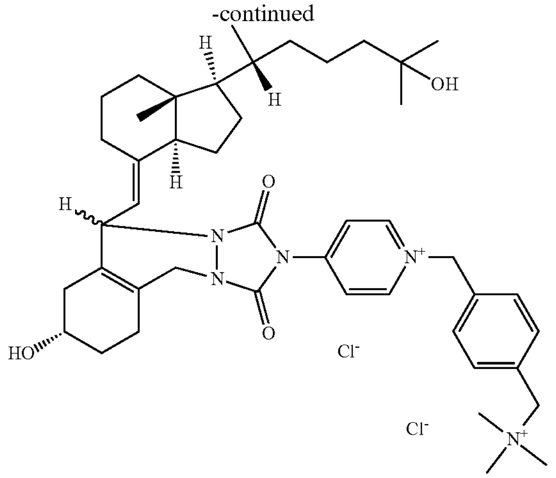

25-Hydroxyvitamin D monohydrate (0.024 mmol) and [4-[[4-(3,5-dioxo-1,2,4-triazolidin-4-yl)pyridin-1-ium-1-yl]methyl]phenyl]methyl-trimethyl-ammonium trifluoroacetate (0.029 mmol) were dissolved in MeOH (500 μL). A solution of iodobenzene diacetate (0.033 mmol) in MeOH (500 μL) was added to the first solution. The reaction mixture was stirred at r.t. for 15 min. Full conversion of vitamin D to the corresponding product was observed. The solvent was removed under vacuum and the residue was purified by preparative HPLC. Product was obtained as chloro salt after ion exchange.

HPLC Method C-18 Column:

0 min: 100% $H_2O$ 0.1% TFA, 0% $CH_3CN$ 0.1% TFA;
0-20 min: 5% $H_2O$ 0.1% TFA, 95% $CH_3CN$ 0.1% TFA;
20-40 min: 5% $H_2O$ 0.1% TFA; 95% $CH_3CN$ 0.1% TFA;
40-45 min: 2% $H_2O$ 0.1% TFA; 98% $CH_3CN$ 0.1% TFA;
45-50 min: 2% $H_2O$ 0.1% TFA; 98% $CH_3CN$ 0.1% TFA;
50-55 min: 60% $H_2O$ 0.1% TFA; 40% $CH_3CN$ 0.1% TFA;
55-65 min: 60% $H_2O$ 0.1% TFA; 40% $CH_3CN$ 0.1% TFA.

$^1H$ NMR (400 MHz, METHANOL-$d_4$) δ ppm 0.46 (s, 2H) 0.59 (s, 1H) 0.90-0.98 (m, 4H) 1.14 (s, 3H) 1.15 (s, 3H) 1.25-1.47 (m, 10H) 1.58-2.30 (m, 12H) 2.37-2.46 (m, 1H) 2.97-3.86 (m, 1H) 3.12 (s, 9H) 3.82-4.02 (m, 2H) 4.15-4.26 (m, 1H) 4.57 (s, 2H) 4.76-4.82 (m, 1H) 5.10-5.17 (m, 1H) 5.87 (s, 2H) 7.59-7.73 (m, 4H) 8.78-8.90 (m, 2H) 9.02-9.16 (m, 2H).

HPLC-MS (m/z) $[M]^{2+}$ calcd 376.75, found 370.06.

Example 3: Label 15

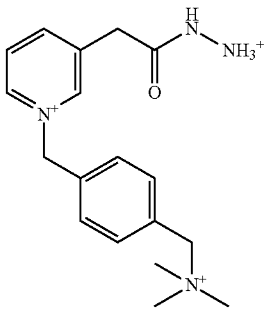 [SMILES: C[N+](C)(C)Cc1ccc(C[n+]2cccc(CC(=O)N[NH3+])c2)cc1]

Synthesis of Label 15

Step 1: Synthesis of [4-[[3-(2-methoxy-2-oxoethyl)pyridin-1-ium-1-yl]methyl]phenyl]methyltrimethylammonium bistrifluoroacetate

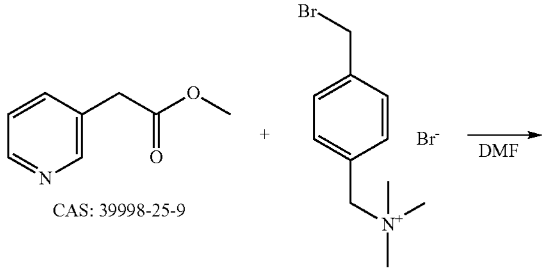

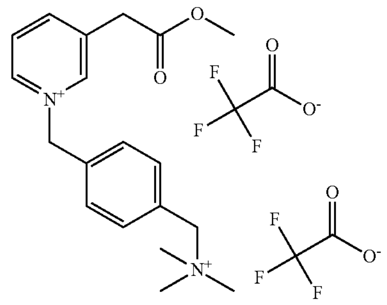

[4-[[3-(2-methoxy-2-oxoethyl)pyridin-1-ium-1-yl]methyl]phenyl]methyltrimethyl-ammonium bistrifluoroacetate The mixture of methyl 2-(3-pyridyl)acetate (0.161 mmol) and 3-bromopropyl(trimethyl)ammonium bromide (0.146 mmol) was dissolved in dry DMF (1 mL). At 70° C. the solution stirred for 20 h. The solvent was removed and purification proceeded on a preparative HPLC yielding 30.8 mg of the desired product as colorless oil.

HPLC Method C-18 Column:

0 min: 100% $H_2O$ 0.1% TFA, 0% $CH_3CN$ 0.1% TFA;
0-40 min: 90% $H_2O$ 0.1% TFA, 10% $CH_3CN$ 0.1% TFA;
40-44 min: 2% $H_2O$ 0.1% TFA; 98% $CH_3CN$ 0.1% TFA;
44-52 min: 2% $H_2O$ 0.1% TFA; 98% $CH_3CN$ 0.1% TFA;
52-54 min: 60% $H_2O$ 0.1% TFA; 40% $CH_3CN$ 0.1% TFA;
54-59 min: 60% $H_2O$ 0.1% TFA; 40% $CH_3CN$ 0.1% TFA;
59-60 min: 60% $H_2O$ 0.1% TFA; 40% $CH_3CN$ 0.1% TFA.

$^1H$ NMR (400 MHz, METHANOL-$d_4$) δ ppm 3.10 (s, 9H) 3.73 (s, 3H) 4.02 (s, 2H) 4.55 (s, 2H) 5.92 (s, 2H) 7.58-7.72 (m, 4H) 8.10 (dd, J=7.97, 6.21 Hz, 1H) 8.57 (d, J=8.16 Hz, 1H) 9.02 (d, J=6.15 Hz, 1H) 9.11 (s, 1H).

$^{13}C$ NMR (150 MHz, METHANOL-$d_4$) δ ppm 36.13 (1C), 51.67 (1C) 51.76 (3C), 63.60 (1C), 68.28 (1C), 127.80 (1C), 129.33 (1C), 129.36 (2C), 133.73 (2C), 135.95 (1C), 136.75 (1C), 143.14 (1C), 145.41 (1C), 147.30 (1C), 169.97 (1C).

HPLC-MS (m/z) $[M+TFA]^+$ calcd 427.18, found 427.61.

Step 2: Synthesis of [4-[[3-[2-(azaniumylamino)-2-oxoethyl]pyridin-1-ium-1-yl]methyl]phenyl]methyl-trimethylammonium tristrifluoroacetate

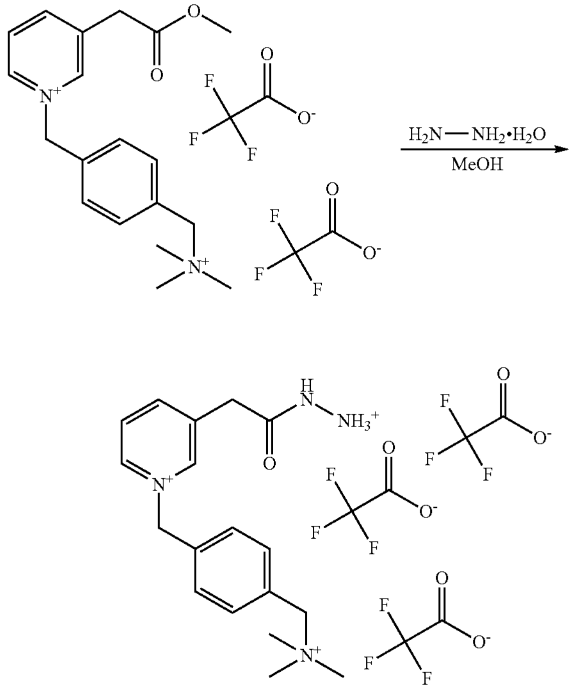

[4-[[3-[2-(azaniumylamino)-2-oxoethyl]pyridin-l-ium-l-yl]methyl]phenyl]methyl-trimethylammonium tristrifluoroacetate

[4-[[3-(2-methoxy-2-oxoethyl)pyridin-1-ium-1-yl] methyl]phenyl]methyltrimethyl-ammonium bistrifluoroacetate (0.057 mmol) was dissolved in dry MeOH (1 mL) and hydrazine hydrate (0.617 mmol) was added. The solution was stirred at 50° C. for 3 h. The solution was then allowed to cool down to room temperature and the solvents were removed in vacuo and the crude mixture was subjected to purification by preparative HPLC yielding 21.6 mg of the desired product as a colorless oil.

HPLC Method C-18 Column:

0 min: 100% $H_2O$ 0.1% TFA, 0% $CH_3CN$ 0.1% TFA;

0-40 min: 90% $H_2O$ 0.1% TFA, 10% $CH_3CN$ 0.1% TFA;

40-44 min: 2% $H_2O$ 0.1% TFA; 98% $CH_3CN$ 0.1% TFA;

44-52 min: 2% $H_2O$ 0.1% TFA; 98% $CH_3CN$ 0.1% TFA;

52-54 min: 60% $H_2O$ 0.1% TFA; 40% $CH_3CN$ 0.1% TFA;

54-59 min: 60% $H_2O$ 0.1% TFA; 40% $CH_3CN$ 0.1% TFA;

59-60 min: 60% $H_2O$ 0.1% TFA; 40% $CH_3CN$ 0.1% TFA.

$^1H$ NMR (400 MHz, METHANOL-$d_4$) δ ppm 3.10 (s, 9H) 3.98 (s, 2H) 4.55 (s, 2H) 5.92 (s, 2H) 7.60-7.69 (m, 4H) 8.10 (dd, J=7.97, 6.21 Hz, 1H) 8.57 (d, J=8.03 Hz, 1H) 9.02 (d, J=6.15 Hz, 1H) 9.14 (s, 1H).

$^{13}C$ NMR (150 MHz, METHANOL-$d_4$) δ ppm 35.50 (1C), 51.77 (3C), 63.61 (1C), 68.26 (1C), 127.84 (1C), 129.32 (1C), 129.39 (2C), 133.72 (2C), 135.89 (1C), 136.35 (1C), 143.25 (1C), 145.37 (1C), 147.16 (1C), 167.93 (1C).

The compound can also be obtained as a different type of salt.

Example 4: Label 16

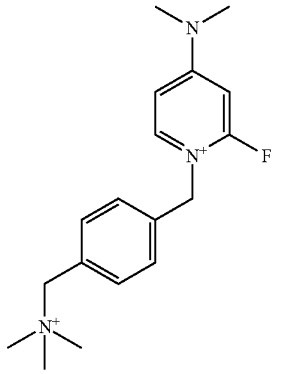 [SMILES: CN(C)c1cc[n+](Cc2ccc(C[N+](C)(C)C)cc2)c(F)c1]

Synthesis of Label 16

Synthesis of [4-[[4-(dimethylamino)-2-fluoro-pyridin-1-ium-1-yl]methyl]phenyl]methyl-trimethyl-ammonium trifluoroacetate

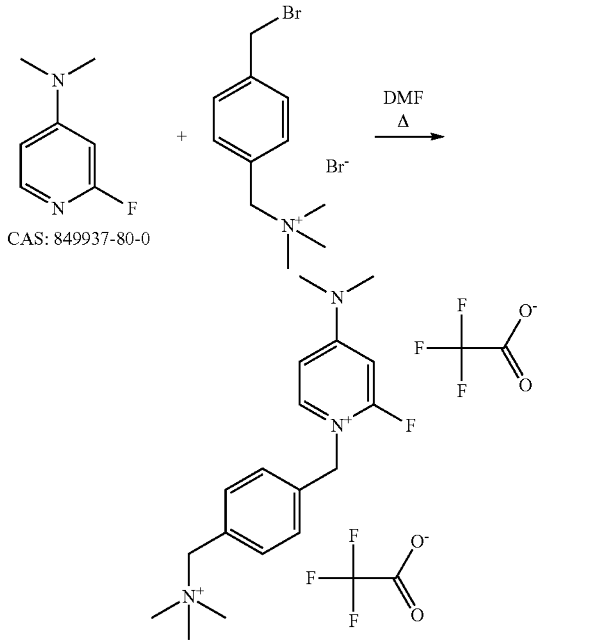

[4-[[4-(dimethylamino)-2-fluoro-pyridin-l-ium-1-yl]methyl]phenyl]methyl-trimethyl-ammonium trifluoroacetate 2-Fluoro-N,N-dimethylpyridin-4-amine (0.36 mmol) and 4-(bromomethyl)benzyltrimethylammonium bromide (0.46 mmol) [synthesized as previously reported in Polym. Chem. 2014, 5, 1180-1190] were dissolved in 1 mL of dry DMF. The reaction mixture was stirred at 90° C. for 48 h. The solvent was removed under vacuum and residue was purified by preparative HPLC. The pure fractions were collected and concentrated under vacuum to give the product 66 mg (35% yield) as a colourless oil.

HPLC Method C-18 Column:

0 min: 100% $H_2O$ 0.1% TFA, 0% $CH_3CN$ 0.1% TFA;

0-60 min: 70% $H_2O$ 0.1% TFA, 30% $CH_3CN$ 0.1% TFA;
60-64 min: 2% $H_2O$ 0.1% TFA; 98% $CH_3CN$ 0.1% TFA;
64-74 min: 2% $H_2O$ 0.1% TFA; 98% $CH_3CN$ 0.1% TFA;
74-79 min: 60% $H_2O$ 0.1% TFA; 40% $CH_3CN$ 0.1% TFA;
79-90 min: 60% $H_2O$ 0.1% TFA; 40% $CH_3CN$ 0.1% TFA.

$^1H$ NMR (400 MHz, ACETONITRILE-$d_3$) δ ppm 3.04 (s, 9H) 3.18 (s, 3H) 3.23 (s, 3H) 4.50 (s, 2H) 5.41 (d, J=2.01 Hz, 2H) 6.69 (dd, J=9.29, 2.89 Hz, 1H) 6.87 (dd, J=7.72, 2.82 Hz, 1H) 7.48 (d, J=8.03 Hz, 2H) 7.54-7.65 (m, 2H) 8.07 (dd, J=7.78, 6.15 Hz, 1H).

$^{19}F$ NMR (376 MHz, ACETONITRILE-$d_3$) δ ppm −90.63 (dd, J=8.94, 6.56 Hz, 1 F) −75.66 (s, 1 F).

HPLC-MS (m/z) $[M]^{2+}$ calcd 151.60, found 151.77.

Preparation of Label 16-Analyte Derivative (Complex) and its Analysis Via MS

Synthesis of Estradiol Conjugate

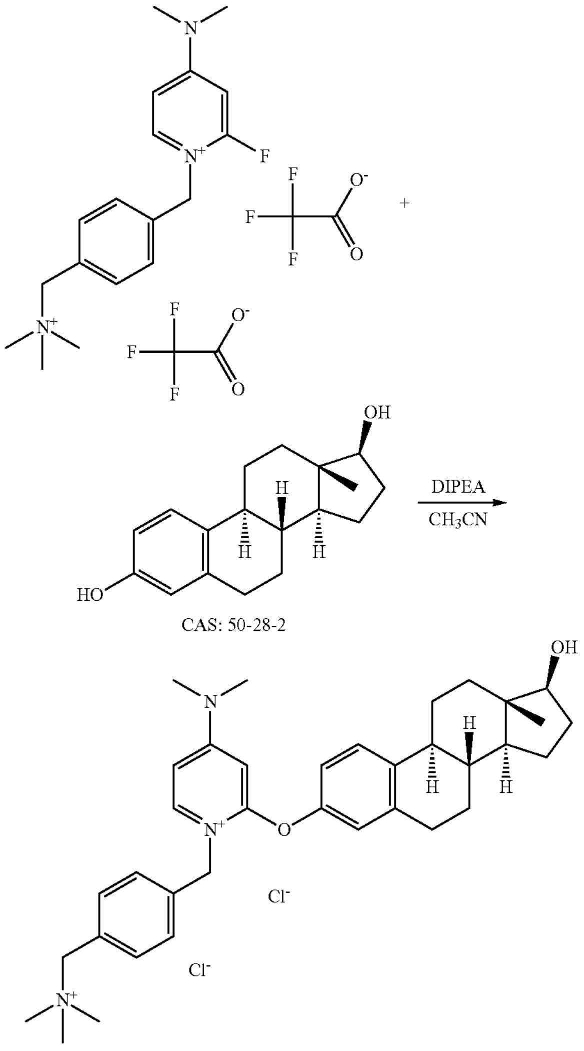

Estradiol (0.09 mmol) and [4-[[4-(dimethylamino)-2-fluoro-pyridin-1-ium-1-yl]methyl]phenyl]methyl-trimethyl-ammonium trifluoroacetate (0.11 mmol) were dissolved in $CH_3CN$ (1 ml). Then DIPEA (0.14 mmol) was added and the reaction mixture stirred at r.t. for 30 min. The solvent was removed under vacuum and the residue was purified by preparative HPLC. The pure fractions were collected and lyophilized to obtain the product as a white solid.

HPLC Method C-18 Column:

0 min: 100% $H_2O$ 0.1% TFA, 0% $CH_3CN$ 0.1% TFA;
0-60 min: 50% $H_2O$ 0.1% TFA, 50% $CH_3CN$ 0.1% TFA;
60-64 min: 2% $H_2O$ 0.1% TFA; 98% $CH_3CN$ 0.1% TFA;
64-74 min: 2% $H_2O$ 0.1% TFA; 98% $CH_3CN$ 0.1% TFA;
74-79 min: 60% $H_2O$ 0.1% TFA; 40% $CH_3CN$ 0.1% TFA;
79-90 min: 60% $H_2O$ 0.1% TFA; 40% $CH_3CN$ 0.1% TFA.

$^1H$ NMR (400 MHz, METHANOL-$d_4$) δ ppm 0.77 (s, 3H) 1.15-1.59 (m, 7H) 1.62-1.77 (m, 1H) 1.86-2.10 (m, 41H) 2.19-2.30 (m, 1H) 2.30-2.40 (m, 1H) 2.81-2.87 (m, 2H) 2.96 (s, 3H) 3.09 (s, 9H) 3.23 (s, 3H) 3.66 (t, J=8.60 Hz, 1H) 4.53 (s, 2H) 5.54 (s, 2H) 5.85 (d, J=2.76 Hz, 1H) 6.79-6.85 (m, 2H) 6.87 (dd, J=7.78, 2.76 Hz, 1H) 7.40 (d, J=8.41 Hz, 1H) 7.52 (d, J=8.16 Hz, 2H) 7.61 (d, J=8.28 Hz, 2H) 8.19 (d, J=7.78 Hz, 1H).

HPLC-MS (m/z) $[M]^{2+}$ calcd 277.69, found 278.05.

The compound can also be obtained as a different type of salt.

Label 16b: Additional Synthesized Conjugate

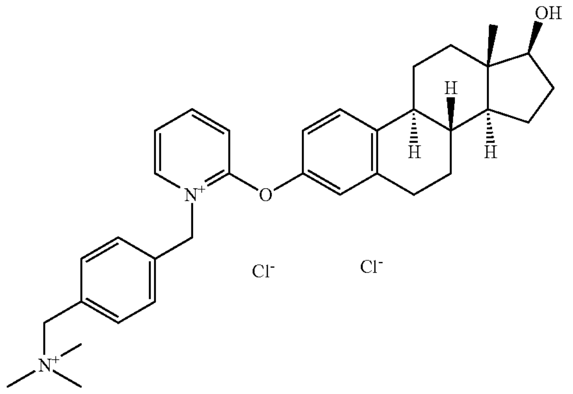

Yield: 21.0 mg as a colorless solid.

HPLC Method C-18 Column:

0 min: 100% $H_2O$ 0.1% TFA, 0% $CH_3CN$ 0.1% TFA;
0-60 min: 30% $H_2O$ 0.1% TFA, 70% $CH_3CN$ 0.1% TFA;
60-64 min: 2% $H_2O$ 0.1% TFA; 98% $CH_3CN$ 0.1% TFA;
64-80 min: 2% $H_2O$ 0.1% TFA; 98% $CH_3CN$ 0.1% TFA;
80-83 min: 60% $H_2O$ 0.1% TFA; 40% $CH_3CN$ 0.1% TFA;
83-89 min: 60% $H_2O$ 0.1% TFA; 40% $CH_3CN$ 0.1% TFA;
89-90 min: 60% $H_2O$ 0.1% TFA; 40% $CH_3CN$ 0.1% TFA.

$^1H$ NMR (400 MHz, METHANOL-$d_4$) δ ppm 0.78 (s, 3H) 1.16-1.61 (m, 7H) 1.64-1.88 (m, 1H) 1.80-2.12 (m, 4H) 2.21-2.31 (m, 1H) 2.38 (br s, 1H) 2.87 (br s, 2H) 3.12 (s, 9H) 3.67 (t, J=8.53 Hz, 1H) 4.60 (s, 2H) 5.94 (s, 2H) 6.90-7.00 (m, 2H) 7.24 (d, J=8.66 Hz, 1H) 7.43-7.53 (m, 1H) 7.62-7.79 (m, 5H) 8.44 (t, J=8.09 Hz, 1H) 8.93 (d, J=6.27 Hz, 1H).

HPLC-MS (m/z) $[M]^{2+}$ calcd 256.17, found 256.69.

Example 5: Label 17

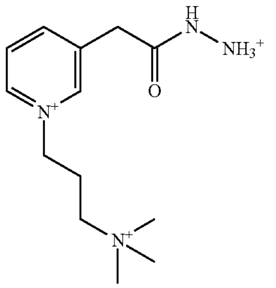 [SMILES: C[N+](C)(C)CCC[n+]1cccc(CC(=O)N[NH3+])c1]

Synthesis of Label 17

Step 1: Synthesis of 3-[3-(2-methoxy-2-oxoethyl) pyridin-1-ium-1-yl]propyltrimethylammonium bis-trifluoroacetate

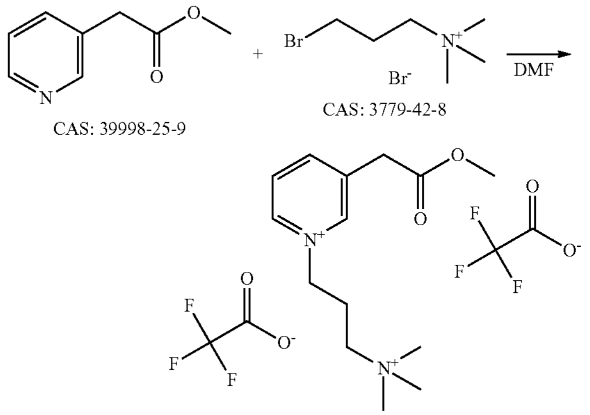

CAS: 39998-25-9

CAS: 3779-42-8

3-[3-(2-methoxy-2-oxoethyl)pyridin-1-ium-1-yl]propyltrimethylammonium bistrifluoroacetate The mixture of methyl 2-(3-pyridyl)acetate (1.610 mmol) and 3-bromopropyl(trimethyl)ammonium bromide (1.628 mmol) was dissolved in dry DMF (1 mL). At 100° C. the solution stirred for 18 h. The solvent was removed and purification proceeded on a preparative HPLC yielding 292.6 mg of the desired product as a black oil.

HPLC Method C-18 Column:

0 min: 100% $H_2O$ 0.1% TFA, 0% $CH_3CN$ 0.1% TFA;

0-60 min: 70% $H_2O$ 0.1% TFA, 30% $CH_3CN$ 0.1% TFA;

60-64 min: 2% $H_2O$ 0.1% TFA; 98% $CH_3CN$ 0.1% TFA;

64-80 min: 2% $H_2O$ 0.1% TFA; 98% $CH_3CN$ 0.1% TFA;

80-83 min: 60% $H_2O$ 0.1% TFA; 40% $CH_3CN$ 0.1% TFA;

83-89 min: 60% $H_2O$ 0.1% TFA; 40% $CH_3CN$ 0.1% TFA;

89-90 min: 60% $H_2O$ 0.1% TFA; 40% $CH_3CN$ 0.1% TFA.

$^1H$ NMR (400 MHz, METHANOL-$d_4$) δ ppm 1.95-2.02 (m, 2H) 3.22 (s, 3H) 3.60-3.64 (m, 2H) 3.75 (s, 3H) 4.05-4.08 (m, 2H) 4.81 (s, 2H) 8.13 (dd, J=6.15, 7.93 Hz, 1H) 8.60 (d, J=8.10 Hz, 1H) 9.07 (d, J=6.29 Hz, 1H) 9.18 (s, 1H).

$^{13}C$ NMR (101 MHz, METHANOL-$d_4$) δ ppm 24.83 (1C) 36.33 (1C) 51.73 (1C) 52.62 (1C) 52.66 (1C) 52.70 (1C) 57.82 (1C) 62.35 (1C) 127.69 (1C) 136.55 (1C) 143.24 (1C) 145.34 (1C) 147.31 (1C) 170.02 (1C).

Step 2: Synthesis of 3-[3-[2-(azaniumylamino)-2-oxoethyl]pyridin-1-ium-1-yl]propyltrimethyl-ammonium tristrifluoroacetate

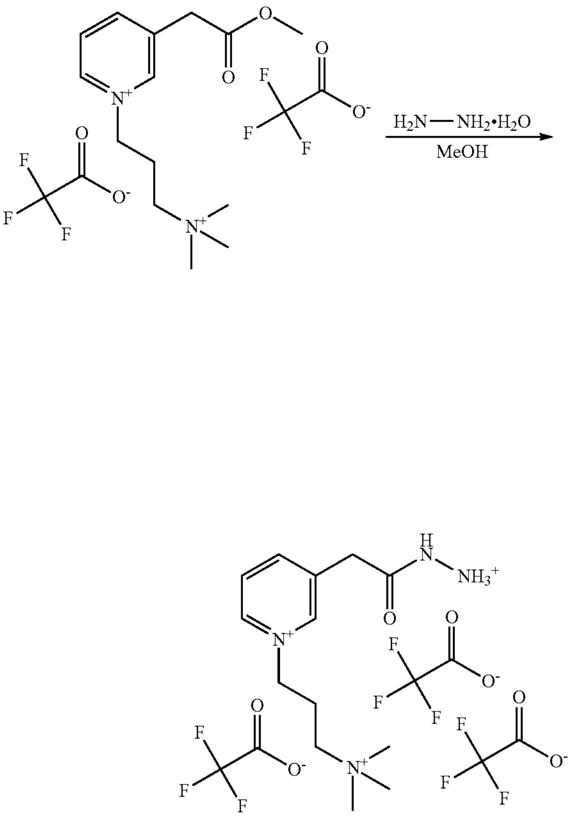

3-[3-[2-(azaniumylamino)-2-oxoethyl]pyridin-l-ium-l-yl]propyltrimethylammonium tristrifluoroacetate 3-[3-(2-methoxy-2-oxoethyl)pyridin-1-ium-1-yl]propyltrimethylammonium bistrifluoroacetate (0.205 mmol) was dissolved in dry MeOH (2 mL) and hydrazine hydrate (2.058 mmol) was added. The solution was stirred at 0° C. for 4 h. The solvents were removed in vacuo and the crude mixture was subjected to purification by preparative HPLC yielding 66.9 mg of the desired product as brownish solid.

HPLC Method C-18 Column:

0 min: 100% $H_2O$ 0.1% TFA, 0% $CH_3CN$ 0.1% TFA;

0-30 min: 90% $H_2O$ 0.1% TFA, 10% $CH_3CN$ 0.1% TFA;

30-34 min: 2% $H_2O$ 0.1% TFA; 98% $CH_3CN$ 0.1% TFA;

34-50 min: 2% $H_2O$ 0.1% TFA; 98% $CH_3CN$ 0.1% TFA;

50-53 min: 60% $H_2O$ 0.1% TFA; 40% $CH_3CN$ 0.1% TFA;

53-59 min: 60% $H_2O$ 0.1% TFA; 40% $CH_3CN$ 0.1% TFA;

59-60 min: 60% $H_2O$ 0.1% TFA; 40% $CH_3CN$ 0.1% TFA.

$^1H$ NMR (400 MHz, METHANOL-$d_4$) δ ppm 2.60-2.69 (m, 2H) 3.21 (s, 3H) 3.58-3.64 (m, 2H) 3.94-3.97 (m, 2H) 4.82 (s; 2H) 8.12 (dd, J=6.20, 7.99 Hz, 1H) 8.58 (d, J=8.28 Hz, 1H) 9.05 (d, J=5.82 Hz, 1H) 9.21 (s, 1H).

Preparation of Label 17-Analyte Derivative (Complex) and its Analysis Via MS

Synthesis of Testosterone Conjugate

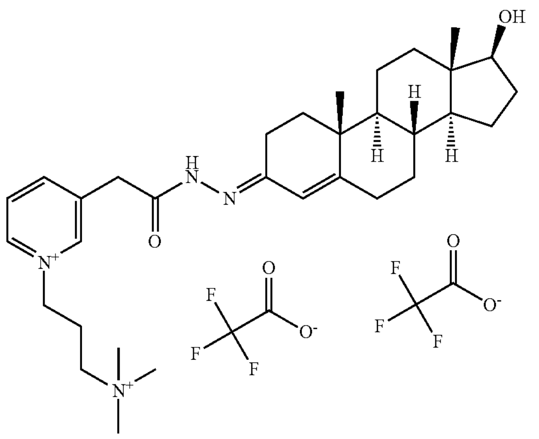

3-[3-[2-(azaniumylamino)-2-oxoethyl]pyridin-1-ium-1-yl]propyltrimethyl-ammonium tristrifluoroacetate (0.113 mmol) and testosterone (0.104 mmol) were dissolved in MeOH (1 mL) and stirred at room temperature for 2.5 d. After removing the solvent in vacuo the crude mixture was purified by preparative HPLC yielding 15.9 mg as colorless solid.

HPLC Method C-18 Column:

0 min: 100% $H_2O$, 0% $CH_3CN$;

0-45 min: 5% $H_2O$, 95% $CH_3CN$;

45-49 min: 5% $H_2O$; 95% $CH_3CN$;

49-50 min: 40% $H_2O$; 60% $CH_3CN$;

50-55 min: 40% $H_2O$; 60% $CH_3CN$;

55-60 min: 40% $H_2O$; 60% $CH_3CN$.

HPLC-MS (m/z) $[M^{2+}+TFA]^+$ calcd 635.38, found 635.56.

The compound can also be obtained as a different type of salt.

Synthesis of 18

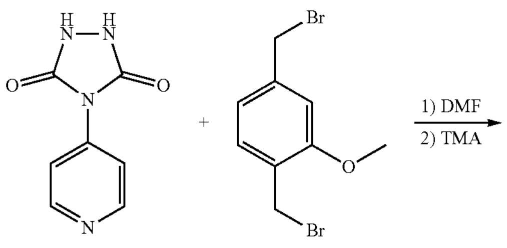

CAS: 1795457-36-1

-continued

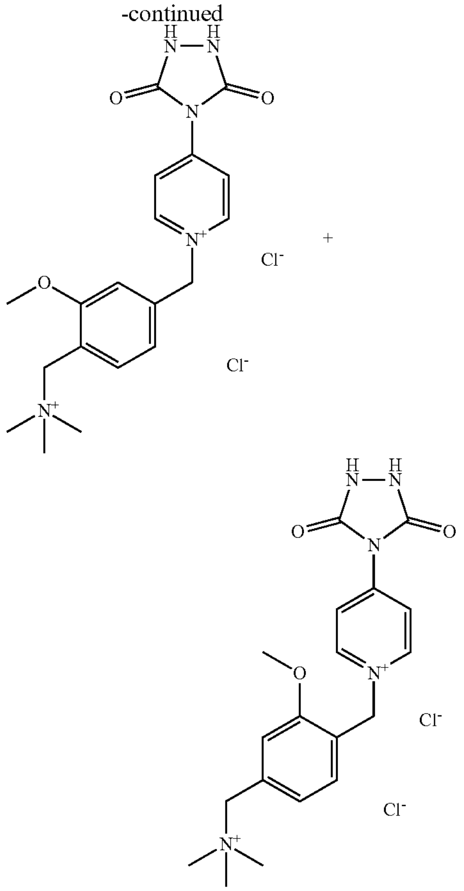

4-(Pyridin-4-yl)-1,2,4-triazolidine-3,5-dione (0.18 mmol) and 1,4-bis(bromomethyl)-2-methoxybenzene [previously reported in *J. Am. Chem. Soc.* 1996, 118, 4271](0.18 mmol) were dissolved in 3 mL of dry DMF. The reaction mixture was stirred during the weekend at room temperature (r.t.). Then TMA solution (0.35 mmol) was added and the mixture was stirred at r.t. for 30 min. The solvent was removed under vacuum and the crude was purified by preparative HPLC. The pure fractions were collected and concentrated under vacuum. The residue was dissolved in diluted HCl(aq) and lyophilised (repeated 2 times). The product was obtained as a mixture of two isomers (ratio −7:3 from NMR) (17% yield) as a white solid.

HPLC Method C-18 Column:

0 min: 100% $H_2O$ 0.1% TFA, 0% $CH_3CN$ 0.1% TFA;

0-10 min: 100% $H_2O$ 0.1% TFA, 0% $CH_3CN$ 0.1% TFA;

10-60 min: 70% $H_2O$ 0.1% TFA, 30% $CH_3CN$ 0.1% TFA;

60-64 min: 2% $H_2O$ 0.1% TFA; 98% $CH_3CN$ 0.1% TFA;

64-74 min: 2% $H_2O$ 0.1% TFA; 98% $CH_3CN$ 0.1% TFA;

74-79 min: 60% $H_2O$ 0.1% TFA; 40% $CH_3CN$ 0.1% TFA;

79-90 min: 60% $H_2O$ 0.1% TFA; 40% $CH_3CN$ 0.1% TFA.

Major isomer: $^1H$ NMR (400 MHz, METHANOL-$d_4$) δ ppm 3.13 (s, 9H) 3.91 (s, 3H) 4.54 (s, 2H) 5.77 (s, 2H) 7.23-7.31 (m, 2H) 7.70 (d, J=8.28 Hz, 1H) 8.76-8.84 (m, 2H) 8.95-9.02 (m, 2H).

Minor isomer: $^1H$ NMR (400 MHz, METHANOL-$d_4$) δ ppm 3.10 (s, 9H) 3.96 (s, 3H) 4.54 (s, 2H) 5.82 (s, 2H) 7.18 (dd, J=7.84, 1.69 Hz, 1H) 7.36 (d, J=1.51 Hz, 1H) 7.56 (d, J=7.78 Hz, 1H) 8.84-8.93 (m, 2H) 9.02-9.09 (m, 2H).

HPLC-MS (m/z) $[M]^{2+}$ calcd 185.60, found 185.78.

Synthesis of Vitamin D Derivatized with Label 18

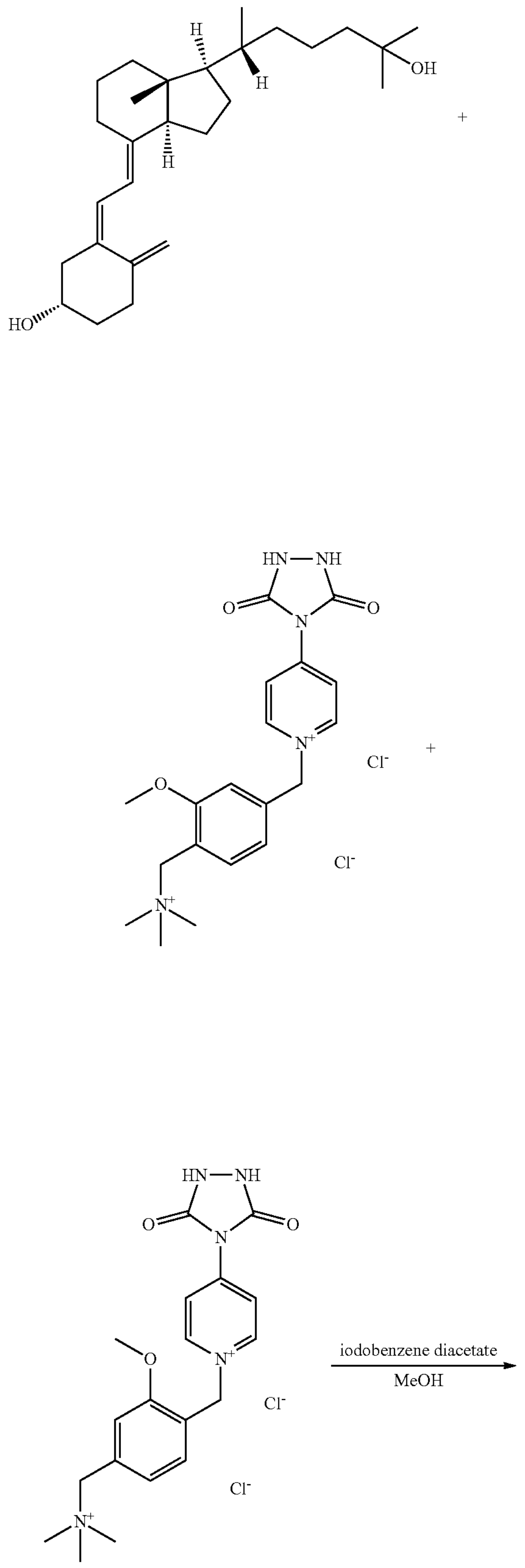

-continued

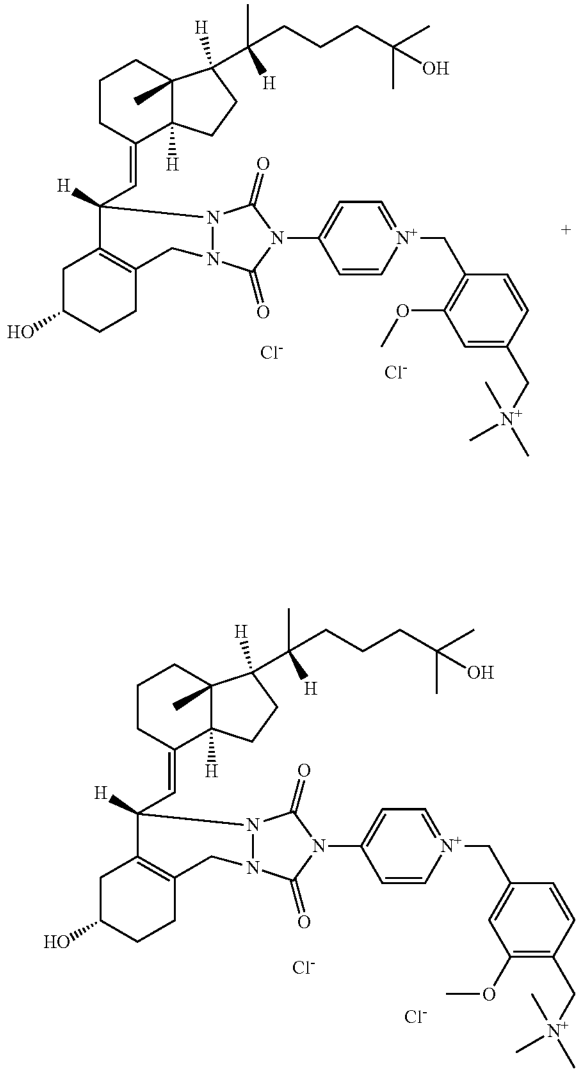

25-Hydroxyvitamin D monohydrate (0.019 mmol) and Label 18 (0.020 mmol) were dissolved in MeOH (500 μL). A solution of iodobenzene diacetate (0.023 mmol) in MeOH was added to the first solution. The reaction mixture was stirred at r.t. for 15 min. Full conversion of vitamin D to the corresponding product was observed. The solvent was removed under vacuum and the crude was purified by preparative HPLC. The pure fractions were collected and concentrated under vacuum. The residue was dissolved in diluted HCl(aq) and lyophilised (repeated 2 times). The product was obtained as a white solid.

HPLC Method C-18 Column:

0 min: 100% $H_2O$ 0.1% TFA, 0% $CH_3CN$ 0.1% TFA;
0-20 min: 5% $H_2O$ 0.1% TFA, 95% $CH_3CN$ 0.1% TFA;
20-40 min: 5% $H_2O$ 0.1% TFA; 95% $CH_3CN$ 0.1% TFA;
40-45 min: 2% $H_2O$ 0.1% TFA; 98% $CH_3CN$ 0.1% TFA;
45-50 min: 2% $H_2O$ 0.1% TFA; 98% $CH_3CN$ 0.1% TFA;
50-55 min: 60% $H_2O$ 0.1% TFA; 40% $CH_3CN$ 0.1% TFA;
55-65 min: 60% $H_2O$ 0.1% TFA; 40% $CH_3CN$ 0.1% TFA.

HPLC-MS (m/z) $[M]^{2+}$ calcd 384.8, found 385.05.

Synthesis of Label 19

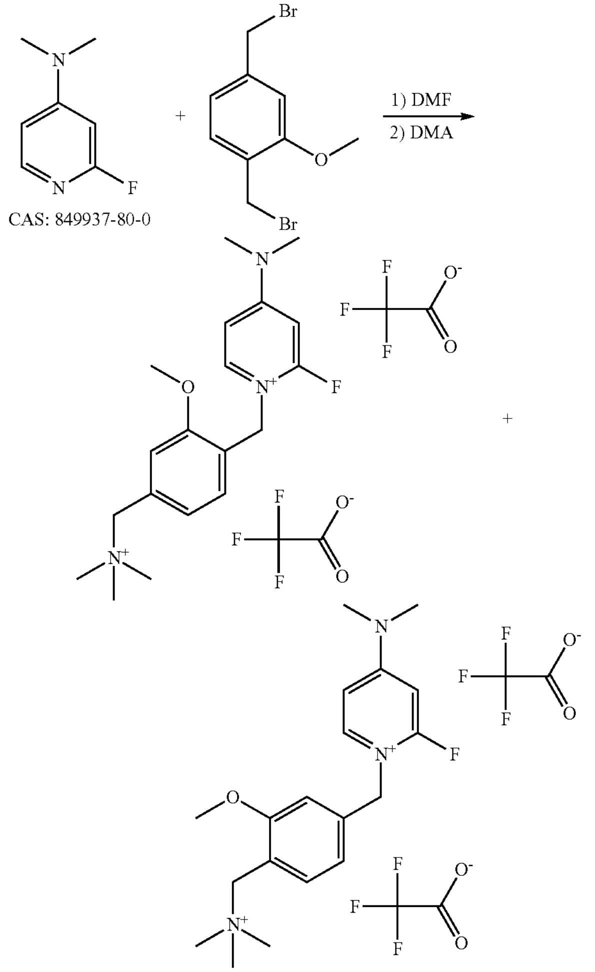

2-Fluoro-N,N-dimethylpyridin-4-amine (0.18 mmol) and 1,4-bis(bromomethyl)-2-methoxybenzene [previously reported in *J. Am. Chem. Soc.* 1996, 118, 4271](0.18 mmol) were dissolved in 3 mL of dry DMF. The reaction mixture was stirred during the weekend at r.t. Then TMA solution (0.36 mmol) was added and the mixture was stirred at r.t. for 2 h. The solvent was removed under vacuum and residue was purified by preparative HPLC. The pure fractions were collected and concentrated under vacuum to give the product as a mixture of two isomers (ratio ~7:3 from NMR) (14% yield) as a colourless oil.

HPLC Method C-18 Column:

0 min: 100% $H_2O$ 0.1% TFA, 0% $CH_3CN$ 0.1% TFA;
0-60 min: 70% $H_2O$ 0.1% TFA, 30% $CH_3CN$ 0.1% TFA;
60-64 min: 2% $H_2O$ 0.1% TFA; 98% $CH_3CN$ 0.1% TFA;
64-74 min: 2% $H_2O$ 0.1% TFA; 98% $CH_3CN$ 0.1% TFA;
74-79 min: 60% $H_2O$ 0.1% TFA; 40% $CH_3CN$ 0.1% TFA;
79-90 min: 60% $H_2O$ 0.1% TFA; 40% $CH_3CN$ 0.1% TFA.

Major isomer: $^1$H NMR (400 MHz, ACETONITRILE-$d_3$) δ ppm 3.05 (s, 9H) 3.16 (s, 3H) 3.21 (s, 3H) 3.87 (s, 3H) 4.46 (s, 2H) 5.29 (d, J=1.63 Hz, 2H) 6.63 (dd, J=9.41, 2.89 Hz, 1H) 6.77 (dd, J=7.78, 2.89 Hz, 1H) 7.16 (dd, J=7.72, 1.44 Hz, 1H) 7.19 (d, J=1.13 Hz, 1H) 7.47 (dd, J=7.78, 1.00 Hz, 1H) 7.92 (dd, J=7.78, 6.15 Hz, 1H).

Minor isomer: $^1$H NMR (400 MHz, ACETONITRILE-$d_3$) δ ppm 3.04 (s, 9H) 3.16 (s, 3H) 3.21 (s, 3H) 3.87 (s, 3H) 4.43 (s, 2H) 5.28 (d, J=1.63 Hz, 2H) 6.62 (br dd, J=9.29, 2.89 Hz, 1H) 6.76 (br dd, J=7.72, 2.82 Hz, 1H) 7.08-7.22 (m, 2H) 7.42-7.50 (m, 1H) 7.91 (br dd, J=7.78, 6.02 Hz, 1H).

$^{19}$F NMR (376 MHz, ACETONITRILE-$d_3$) δ ppm −75.39, −90.11.

HPLC-MS (m/z) $[M+TFA]^+$ calcd 446.21, found 446.39.

Synthesis of Estradiol Conjugated with Label 19

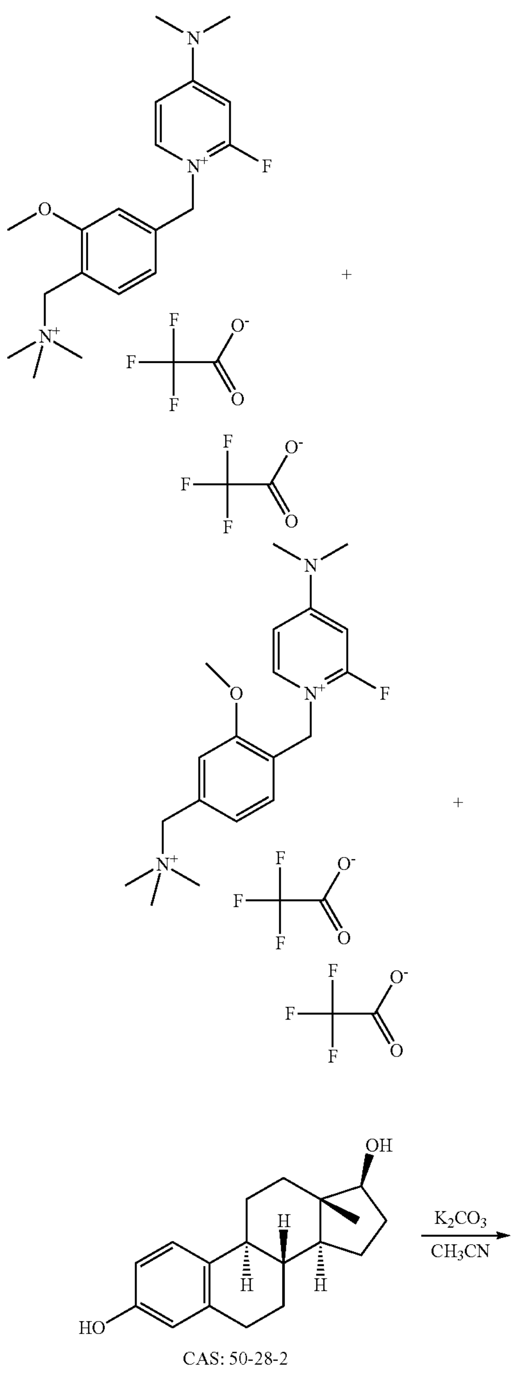

-continued

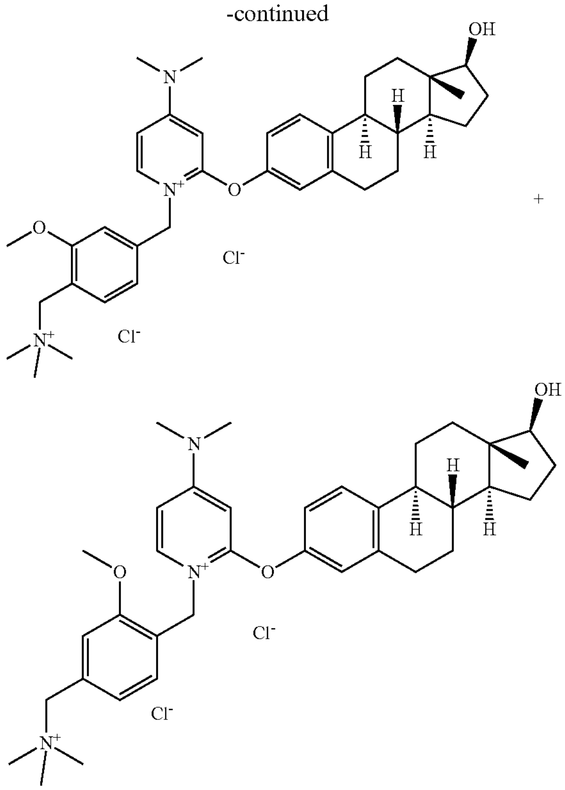

Estradiol (0.022 mmol) and Label 19 (0.026 mmol) were dissolved in $CH_3CN$ (1 mL). Then $K_2CO_3$ (0.066 mmol) was added and the reaction mixture stirred at r.t. for 2 h. The solvent was removed under vacuum and the residue was purified by preparative HPLC. The pure fractions were collected and concentrated under vacuum. The residue was dissolved in diluted HCl(aq) and lyophilised (repeated 2 times). The product was obtained as a mixture of two isomers (ratio −7:3 from NMR) as a white solid.

HPLC Method C-18 Column:

0 min: 100% $H_2O$ 0.1% TFA, 0% $CH_3CN$ 0.1% TFA;

0-60 min: 50% $H_2O$ 0.1% TFA, 50% $CH_3CN$ 0.1% TFA;

60-64 min: 2% $H_2O$ 0.1% TFA; 98% $CH_3CN$ 0.1% TFA;

64-74 min: 2% $H_2O$ 0.1% TFA; 98% $CH_3CN$ 0.1% TFA;

74-79 min: 60% $H_2O$ 0.1% TFA; 40% $CH_3CN$ 0.1% TFA.

Major isomer: $^1H$ NMR (400 MHz, METHANOL-$d_4$) δ ppm 0.78 (s, 3H) 1.16-1.59 (m, 8H) 1.63-1.79 (m, 1H) 1.87-2.10 (m, 3H) 2.19-2.29 (m, 1H) 2.32-2.40 (m, 1H) 2.83-2.85 (m, 2H) 2.94 (br s, 3H) 3.12 (s, 9H) 3.21 (br s, 3H) 3.67 (t, J=8.66 Hz, 1H) 3.94 (s, 3H) 4.52 (s, 2H) 5.46 (s, 2H) 5.82 (d, J=2.76 Hz, 1H) 6.77-6.83 (m, 3H) 7.16 (dd, J=7.65, 1.51 Hz, 1H) 7.24 (d, J=1.25 Hz, 1H) 7.41 (br d, J=8.03 Hz, 1H) 7.44 (d, J=7.78 Hz, 1H) 8.14 (d, J=7.91 Hz, 1H).

Minor isomer: $^1H$ NMR (400 MHz, METHANOL-$d_4$) δ ppm 0.78 (s, 3H) 1.16-1.59 (m, 8H) 1.63-1.79 (m, 1H) 1.87-2.10 (m, 3H) 2.19-2.29 (m, 1H) 2.32-2.40 (m, 1H) 2.83-2.85 (m, 2H) 2.97 (br s, 3H) 3.08 (s, 3H) 3.23 (br s, 1H) 3.67 (t, J=8.66 Hz, 1H) 3.88 (s, 3H) 4.52 (s, 2H) 5.52 (s, 2H) 5.88 (br d, J=2.76 Hz, 1H) 6.83-6.89 (m, 1H) 7.20-7.22 (m, 1H) 7.41 (br d, J=8.03 Hz, 1H) 7.51 (br d, J=7.78 Hz, 1H) 8.21 (br d, J=7.78 Hz, 1H).

HPLC-MS (m/z) $[M]^{2+}$ calcd 292.7, found 293.04.

Synthesis of Label 20

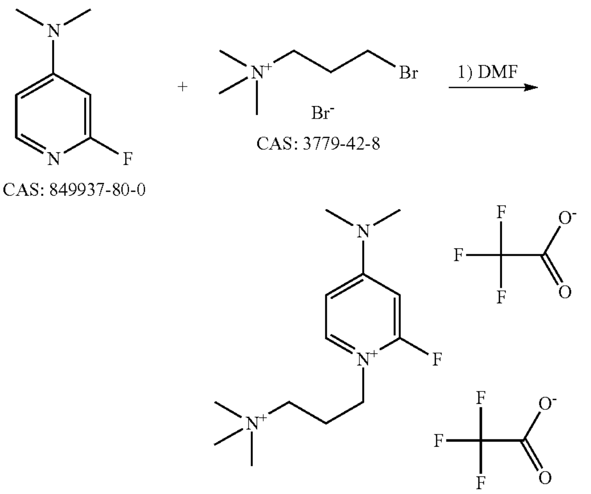

2-Fluoro-N,N-dimethylpyridin-4-amine (0.78 mmol) and (3-bromopropyl)trimethylammonium bromide (0.94 mmol) were dissolved in 1 mL of dry DMF. The reaction mixture was stirred over the weekend at 70° C. The solvent was removed under vacuum and residue was purified by preparative HPLC. The pure fractions were collected and concentrated under vacuum to give the product as a colourless oil (46% yield).

HPLC Method C-18 Column:

0 min: 100% $H_2O$ 0.1% TFA, 0% $CH_3CN$ 0.1% TFA;

0-60 min: 70% $H_2O$ 0.1% TFA, 30% $CH_3CN$ 0.1% TFA;

60-64 min: 2% $H_2O$ 0.1% TFA; 98% $CH_3CN$ 0.1% TFA;

64-74 min: 2% $H_2O$ 0.1% TFA; 98% $CH_3CN$ 0.1% TFA.

$^1H$ NMR (400 MHz, $D_2O$) δ ppm 2.18-2.35 (m, 2H) 3.03 (s, 9H) 3.08 (s, 3H) 3.13 (s, 3H) 3.31-3.39 (m, 2H) 4.10-4.21 (m, 2H) 6.59 (dd, J=9.35, 2.82 Hz, 1H) 6.74 (dd, J=7.78, 2.76 Hz, 1H) 7.77 (dd, J=7.72, 6.09 Hz, 1H).

$^{19}F$ NMR (376 MHz, $D_2O$) δ ppm −91.38−−91.27, −75.63.

$^{13}C$ NMR (101 MHz, DEUTERIUM OXIDE) δ ppm 23.01 (1C) 25.37 (1C) 39.94 (1 C) 47.81 (1C) 53.03 (3C) 62.73 (1C) 91.04 (1C) 91.31 (1C) 106.32 (1C) 139.45 (1 C) 159.87 (1C).

HPLC-MS (m/z) $[M]^{2+}$ calcd 120.60, found 120.59.

Synthesis of Estradiol Conjugated with Label 20

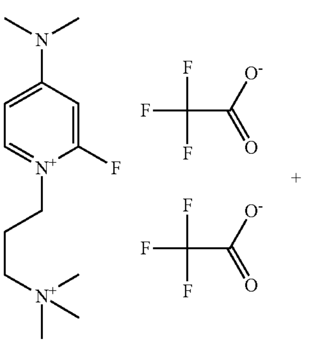

-continued

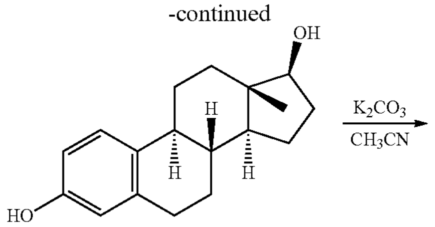

CAS: 50-28-2

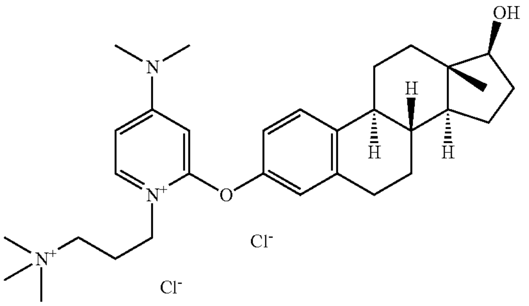

Estradiol (0.073 mmol) and Label 20 (0.11 mmol) were dissolved in $CH_3CN$ (1 mL). Then $K_2CO_3$ (0.22 mmol) was added and the reaction mixture stirred at r.t. for 2 h. The solvent was removed under vacuum and the residue was purified by preparative HPLC. The pure fractions were collected and concentrated under vacuum. The residue was dissolved in diluted HCl(aq) and lyophilised (repeated 2 times). The product was obtained as a white solid.

HPLC Method C-18 Column:

0 min: 100% $H_2O$ 0.1% TFA, 0% $CH_3CN$ 0.1% TFA;
0-60 min: 50% $H_2O$ 0.1% TFA, 50% $CH_3CN$ 0.1% TFA;
60-64 min: 2% $H_2O$ 0.1% TFA; 98% $CH_3CN$ 0.1% TFA;
64-74 min: 2% $H_2O$ 0.1% TFA; 98% $CH_3CN$ 0.1% TFA;
74-79 min: 60% $H_2O$ 0.1% TFA; 40% $CH_3CN$ 0.1% TFA.

$^1H$ NMR (400 MHz, METHANOL-$d_4$) δ ppm 0.79 (s, 3H) 1.22-1.55 (m, 8H) 1.64-1.80 (m, 1H) 1.85-2.12 (m, 3H) 2.20-2.34 (m, 1H) 2.34-2.49 (m, 3H) 2.91 (br dd, J=8.60, 4.08 Hz, 2H) 2.96 (s, 3H) 3.18 (s, 9H) 3.22 (s, 3H) 3.49-3.55 (m, 2H) 3.68 (t, J=8.60 Hz, 1H) 4.37 (t, J=7.28 Hz, 2H) 5.84 (d, J=2.76 Hz, 1H) 6.84 (dd, J=7.65, 2.76 Hz, 1H) 7.06-7.10 (m, 2H) 7.49 (d, J=8.41 Hz, 1H) 8.03 (d, J=7.65 Hz, 1H).

HPLC-MS (m/z) $[M]^{2+}$ calcd 246.68, found 247.00.

This patent application claims the priority of the European patent application 20175802.6, wherein the content of this European patent application is hereby incorporated by references.

The invention claimed is:

1. A compound for quantitative detection of an analyte using mass spectrometric determination,
wherein said compound comprises a permanent charge,
wherein said compound is capable of covalently binding to the analyte,
wherein said compound has a mass m1 and a net charge z1,
wherein the compound is capable of forming at least one daughter ion having a mass m2<m1 and a net charge z2<z1 after fragmentation by mass spectrometric determination,
wherein m1/z1<m2/z2;
wherein the compound is selected from the group consisting of:

(label 13)

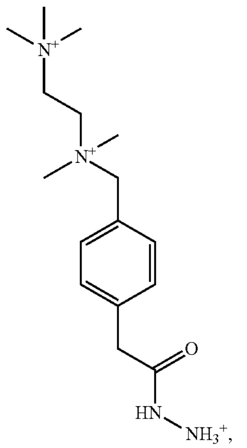

(label 14)

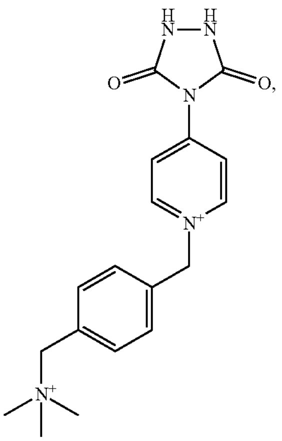

(label 15)

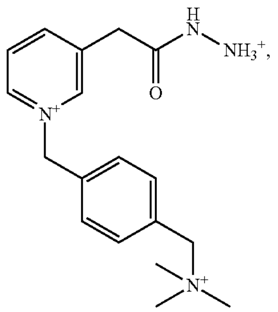

(label 16)

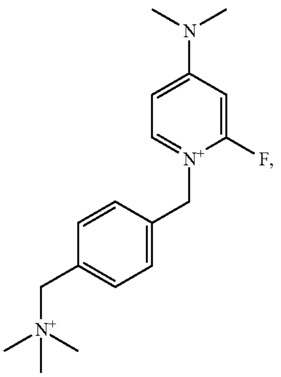

-continued (label 17)

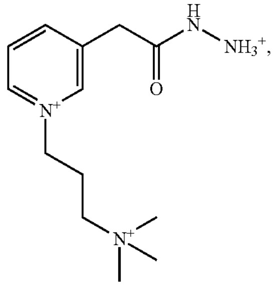

(label 18)

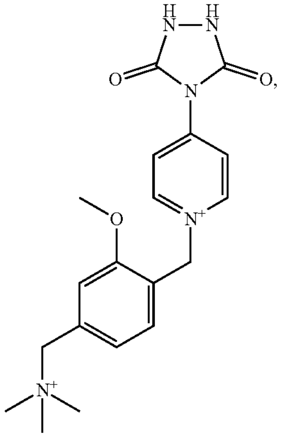

(label 19)

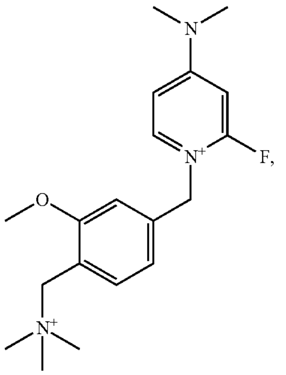

and (label 20)

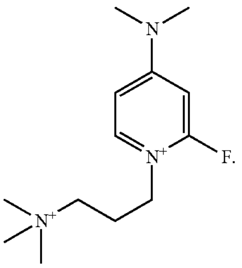

2. The compound of claim 1, wherein the compound is free of trifluoroacetate (TFA).

3. A composition comprising the compound of claim 1.

4. A kit comprising the compound of claim 1.

5. A complex for quantitative detection of an analyte using mass spectrometric determination, wherein the complex is formed by the analyte and the compound of claim 1, which are covalently linked to each other, wherein the complex comprises a permanent charge, wherein said complex has a mass m3 and a net charge z3, wherein the complex is capable of forming at least one daughter ion having a mass $m4<m3$ and a net charge $z4<z3$ after fragmentation by mass spectrometric determination, wherein $m3/z3<m4/z4$.

6. The complex of claim 5, wherein z3=2, wherein after fragmentation the complex is capable of forming the daughter ion with z4=1 and a further daughter ion, wherein the further daughter ion has a net charge z5, wherein z5=1, wherein the daughter ion or the further daughter ion comprises the analyte or fragments thereof.

7. A method for mass spectrometric determination of an analyte comprising the steps of:

(a) reacting the analyte with the compound as defined in claim 1, whereby a complex is formed, (b) subjecting the complex from step (a) to a mass spectrometric analysis, wherein step (b) comprises:

(i) subjecting an ion of the complex to a first stage of mass spectrometric analysis, whereby the ion of the complex is characterized according to its mass/charge (m/z) ratio, (ii) causing fragmentation of the complex ion, whereby a first entity is released and a daughter ion of the complex is generated, wherein the daughter ion of the complex differs in its m/z ratio from the complex ion, and (iii) subjecting the daughter ion of the complex to a second stage of mass spectrometric analysis, whereby the daughter ion of the complex is characterized according to its m/z ratio, and/or wherein (ii) may further comprises alternative fragmentation of the complex ion, whereby a second entity different from the first entity is released and a second daughter ion of the complex is generated, and wherein (iii) may further comprises subjecting the first and second daughter ions of the complex to a second stage of mass spectrometric analysis, whereby the first and second daughter ions of the complex are characterized according to their m/z ratios, wherein the m/z ratio of the first daughter ion and/or the second daughter ion is greater than the m/z ratio of ion of the complex, and wherein a further step (a') before step (a) comprises:

(a') subjecting the ion of the complex or an ion of the compound to an ion exchange of the counter ion, wherein a strongly coordinating anion as the counter ion is exchanged by chloride, bromide or a weekly coordinating counter ion.

8. The method of claim 7, wherein the strongly coordinating anion is trifluoroacetate.

* * * * *